(12) United States Patent
Natrajan et al.

(10) Patent No.: US 8,778,624 B2
(45) Date of Patent: Jul. 15, 2014

(54) ZWITTERION-CONTAINING ACRIDINIUM COMPOUNDS

(75) Inventors: Anand Natrajan, Manchester, NH (US); David Sharpe, Foxborough, MA (US); Qingping Jiang, East Walpole, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 13/510,158

(22) PCT Filed: Nov. 12, 2010

(86) PCT No.: PCT/US2010/056466
§ 371 (c)(1),
(2), (4) Date: May 16, 2012

(87) PCT Pub. No.: WO2011/060228
PCT Pub. Date: May 19, 2011

(65) Prior Publication Data
US 2012/0225497 A1   Sep. 6, 2012

Related U.S. Application Data

(60) Provisional application No. 61/261,465, filed on Nov. 16, 2009.

(51) Int. Cl.
G01N 33/53      (2006.01)
G01N 33/533     (2006.01)
G01N 21/76      (2006.01)

(52) U.S. Cl.
USPC ........... 435/7.92; 435/7.1; 436/532; 436/544; 436/56; 436/172

(58) Field of Classification Search
None
See application file for complete search history.

(56) References Cited

U.S. PATENT DOCUMENTS 6,664,043 B2 * 12/2003 Natrajan et al. ................ 435/5
7,309,615 B2    12/2007 Natrajan et al.
7,582,260 B2 *  9/2009 Dratz et al. ............... 422/82.05

FOREIGN PATENT DOCUMENTS

WO   WO9602839 A1    2/1996
WO   WO 00/09487 A1  2/2000
WO   WO2004/009598 A1  1/2004

* cited by examiner

*Primary Examiner* — Shafiqul Haq
(74) *Attorney, Agent, or Firm* — Kevin Stein

(57) ABSTRACT

Hydrophilic, chemiluminescent acridinium compounds containing zwitterions are disclosed. These acridinium compounds, when used as chemiluminescent labels in immunochemistry assays and the like, exhibit decreased non-specific binding to solid phases and provide increased assay sensitivity.

31 Claims, 6 Drawing Sheets

$R_2, R_3$ = H (NSP-DMAE-Z-NHS, 11f)
$R_2, R_3$ = —O—CH(OMe)(OMe)  p = 1 (NSP-2,7-DMG-DMAE-Z-NHS, 12h)
$R_2, R_3$ = H, p = 0 (NSP-DMAE-Z2-NHS, 13e)

NSP-DMAE-ZCB-NHS, 14d

ZWITTERION-CONTAINING ACRIDINIUM COMPOUNDS

FIELD OF INVENTION

The present invention relates to hydrophilic, chemiluminescent acridinium compounds containing zwitterions. These acridinium compounds, because of their hydrophilic nature, exhibit low non-specific binding to solid phases and are potentially useful for improving assay sensitivity.

BACKGROUND

Chemiluminescent acridinium esters have emerged to be extremely useful labels for both immunoassays as well as nucleic acid assays. Light emission from acridinium esters is triggered by the reaction with alkaline hydrogen peroxide which causes scission of the phenolic ester bond and the formation of excited state acridone, which is the light emitting species. The formation of a dioxetanone intermediate following the departure of the phenol leaving group has been proposed in the reaction mechanism and is presumed to be the precursor to the excited state acridone. The duration of light emission from acridinium esters which, depends upon the reaction conditions, is normally complete within a few seconds and can be quantitatively measured using a luminometer. The application of the acridinium ester 9-carboxyphenyl-N-methylacridinium bromide in an immunoassay was disclosed by Simpson, J. S. A. et al. (*Nature* vol. 279, pp. 646-647 (1979). However, this acridinium ester is quite unstable, thereby limiting its commercial utility. This instability arises from hydrolysis of the labile 9-carboxyphenyl ester linkage between the phenol and the acridinium ring.

In an attempt to stabilize the phenolic ester in acridinium esters, Law et al. (*Journal of Bioluminescence and Chemiluminescence*, vol. 4, pp. 88-89 (1989) introduced two, flanking methyl groups to stabilize this ester bond. The resulting sterically stabilized acridinium ester, abbreviated as DMAE-NHS [2',6'-dimethyl-4'-(N-succinimidyloxycarbonyl)phenyl 10-methylacridinium-9-carboxylate] was found to have the same light output as an acridinium ester lacking the two methyl groups. On the other hand, the stability of the former compound when conjugated to an immunoglobulin was vastly superior and showed no loss of chemiluminescent activity even after one week at 37° C. at pH 7. In contrast, the unsubstituted acridinium ester only retained 10% of its activity when subjected to the same treatment.

To alleviate the hydrophobic nature of DMAE and its derivatives, U.S. Pat. No. 5,656,426 by Law et al. disclosed a hydrophilic version of DMAE termed NSP-DMAE-NHS ester where the N-methyl group had been replaced with an N-sulfopropyl (NSP) group. Both DMAE and NSP-DMAE are now widely used in the commercial, automated immunoassay analyzers ACS:180™ and Centaur™ of Siemens Healthcare Diagnostics.

To further increase the hydrophilicity of NSP-DMAE, Natrajan et al. in U.S. Pat. No. 6,664,043 B2 disclosed NSP-DMAE derivatives with hydrophilic modifiers such as poly (ethylene)glycol and anionic spermine derivatives attached to the phenol. The structure of one such acridinium ester called NSP-DMAE-HEG-Glutarate-NHS, (abbreviated as NSP-DMAE-HEG) and containing a hexa(ethylene)glycol derivative (HEG) is illustrated in the following drawing. In this compound an α,ω-diamino hexa(ethylene) glycol (diamino-HEG) moiety is attached to the phenol to increase the aqueous solubility of the acridinium ester. A glutarate moiety was appended to the end of diamino-HEG and was converted to the NHS ester to enable labeling of various molecules. In addition to HEG, anionic modifiers derived from spermine with sulfonate and carboxylate groups were also disclosed by Natrajan et al. in U.S. Pat. No. 6,664,043 B2.

Recently, Natrajan et al. in U.S. Pat. No. 7,309,615 B2 described hydrophilic, high quantum yield acridinium compounds containing hydrophilic alkoxy groups (OR*) at C2 and/or C7 of the acridinium ring, wherein R* is a group comprising a sulfopropyl moiety or ethylene glycol moieties or a combination thereof. The enhanced light output from such compounds and their hydrophilic nature made them useful for improving the sensitivity of immunoassays. The structure of once such compound called NSP-2,7-(OMHEG)$_2$-DMAE-AC-NHS (abbreviated as HQYAE) is illustrated below. This compound and other compounds described in U.S. Pat. No. 7,309,615 B2 contained poly(ethylene)glycol or anionic sulfonate groups attached to the acridinium ring instead of the phenol.

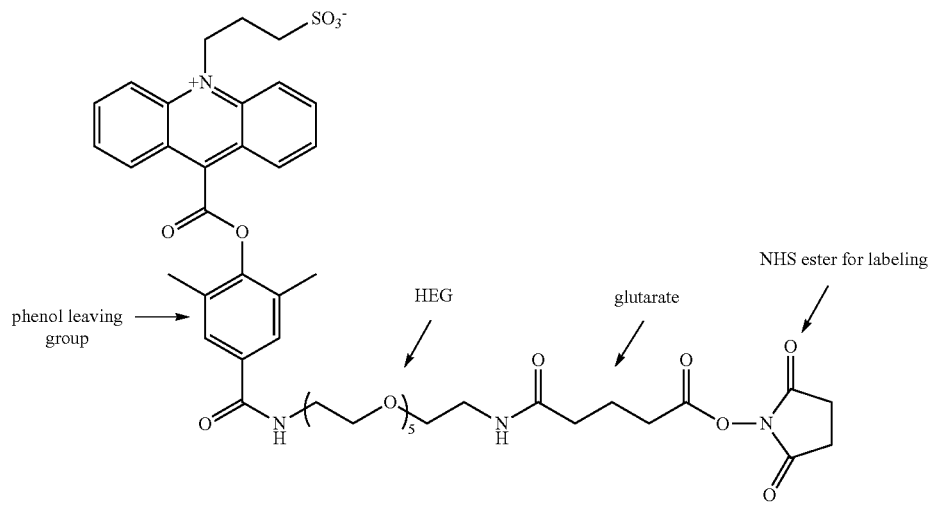

Structure of NSP-DMAE-HEG-Glutarate-NHS

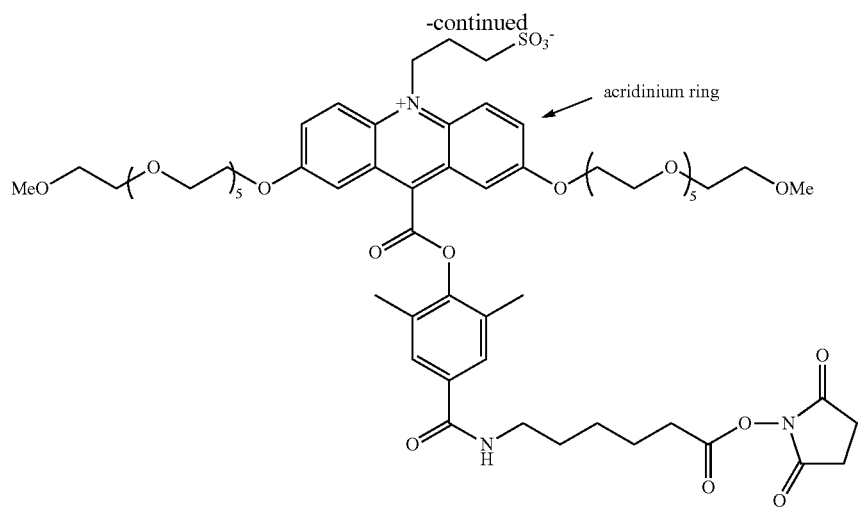

Structure of NSP-2,7-(OMHEG)$_2$-DMAE-AC-NHS

The incorporation of poly(ethylene)glycol (PEG) moieties and anions in the structures of acridinium esters as disclosed in the aforementioned patents were meant to increase the hydrophilic nature of these acridinium esters as well as to lower the non-specific binding of conjugates derived from these compounds. Non-specific binding, in assays using solid phases such as particles or microtiter plates, are undesired binding interactions of these acridinium ester conjugates to these solid phases. These undesired binding interactions typically increase the background of the assay leading to a net lowering of the signal to background ratio in the assay and thereby decreasing assay sensitivity.

The use of poly(ethylene)glycol to devise inert surfaces that resist protein adsorption has been described in the prior art. For example, Ostuni et al. in *J. Am. Chem. Soc.* 2000, 17, 5605-5620, evaluated numerous functional groups attached to self-assembled monolayers for resistance to protein adsorption and observed that poly(ethylene)glycol functional groups conferred the best resistance. More recently, Ladd et al. in *Biomacromolecules* 2008, 9, 1357-1361; and others have reported that zwitterion-modified hydrophilic surfaces are as inert to protein adsorption as PEG and moreover, it has been postulated that zwitterions would be chemically more stable than PEG owing to the latter's propensity for oxidative cleavage. Structures of some common zwitterions such as sulfobetaines, carboxybetaines, phosphobetaines and amine oxides are illustrated in the following drawing. Like PEG, these zwitterions are normally electrically neutral, because of the balance of positive and negative charges within a given structure (R1-R4 are typically alkyl groups).

Examples of Zwitterions

Sulfobetaines

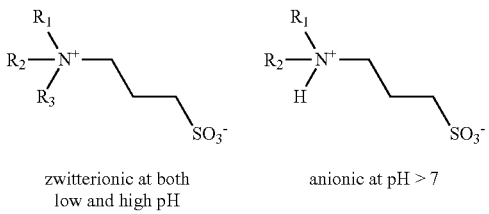

zwitterionic at both low and high pH anionic at pH > 7

Carboxybetaine cationic at low pH

Phosphobetaine

Tertiary Amine Oxide

Sulfobetaines where the nitrogen atom is quarternary maintain their electrical neutrality over a wide pH range. On the other hand sulfobetaines with a trisubstituted nitrogen can acquire a negative charge at higher pH (pH>7) because they can be deprotonated at the nitrogen thereby neutralizing its positive charge. Similarly, carboxybetaines are electrically neutral at higher pH but can be protonated at the carboxylate group and acquire a net positive charge at low pH (pH<5).

Zwitterion-modified fluorescent dyes for applications in proteomics have recently been reported by Dratz and Grieco in U.S. Patent Application No. 0259333 A1 (November 2007). Proteins labeled with zwitterionic dyes were observed to be water soluble and more amenable for electrophoretic analysis and the above authors have claimed methods for protein analysis using zwitterionic dyes.

The incorporation of electrically neutral, zwitterionic functional groups in chemiluminescent acridinium esters to improve their properties such as non-specific binding has not been described the prior art. Such compounds complement the PEG-containing acridinium esters described by Natrajan et al. in U.S. Pat. No. 6,664,043 B2 and U.S. Pat. No. 7,309,615 B2 and, have the potential to improve assay sensitivity.

There is a continuing need in the art for improved chemiluminescent tags for immunoassays and the like. It is therefore an object of the invention to provide chemiluminescent acridinium compounds which exhibit reduced non-specific binding to a solid phase.

SUMMARY OF THE INVENTION

In accordance with the foregoing objectives and others, it has surprisingly been found that the properties of chemiluminescent acridinium compounds are improved by incorporating zwitterionic groups into the molecule to increase its hydrophilicity and consequently reduce non-specific binding with solid phases.

In one aspect of the invention, a chemiluminescent acridinium compound is provided comprising (i) a hydrocarbon group attached to the nitrogen atom of the acridinium nucleus said hydrocarbon group being optionally substituted with up to 20 heteroatoms, and (ii) a carboxyl or sulfonamide group at the $C_9$ position of the acridinium nucleus linked to a substituted hydrocarbon moiety, wherein the acridinium compound comprises at least one zwitterionic functional group attached to the $C_2$ position of the acridinium nucleus, the $C_7$ position of the acridinium nucleus, the hydrocarbon moiety linked to the carboxyl or sulfonamide group, or the hydrocarbon group attached to the nitrogen atom of the acridinium nucleus; wherein said acridinium compound exhibits reduced non-specific binding to a solid phase as compared to an otherwise identical acridinium compound not comprising said zwitterionic functional group.

In one embodiment, the chemiluminescent acridinium compound is an acridinium ester having the following structure shown in Formula I:

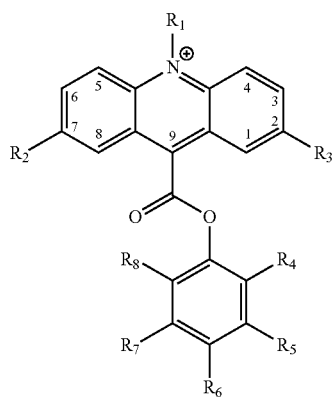

wherein, $R_1$ is a $C_{1-35}$ alkyl, alkenyl, alkynyl or aralkyl group, each of which may contain up to 20 heteroatoms, or a sulfopropyl or sulfobutyl group, or $R_1$ is a group —$R^a$—Z; where $R^a$ is a divalent radical selected from $C_{1-35}$ alkyl, alkenyl, alkynyl, aryl, or aralkyl group, each optionally containing up to 20 heteroatoms;

$R_2$ and $R_3$ are independently selected from (i) hydrogen, (ii) an electron donating group, or (iii) a group —Z;

Z is a zwitterionic group of the form:

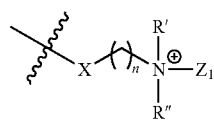

X is independently selected at each occurrence from a bond, —$CH_2$—, oxygen, sulfur, —$NR^N$—, amide (—$NR^N$(CO)—), carbamate (—$NR^N C(O)O$—), or urea (—$NR^N C(O)NR^N$—);

R' and R" are independently selected at each occurrence from $C_{1-35}$ alkyl, alkenyl, alkynyl, aryl, or aralkyl, each optionally containing up to 20 heteroatoms;

$Z_1$ is a group —$R^a$—$Z_2$ where $Z_2$ is selected from carboxylate (—$COO^-$), sulfonate (—$SO_3^-$), sulfate (—$OSO_3^-$), phosphate (—$OP(O)(OR)(O^-)$), or oxide (—$O^-$); or, in the case where $Z_2$ is an oxide (—$O^-$), $R^a$ may be absent;

n is, independently selected at each occurrence, an integer between one and 12; and $R_4$ and $R_8$ are the same or different and are selected from hydrogen, $C_{1-35}$ alkyl, alkenyl, alkynyl, alkoxyl (—OR), alkylthiol (—SR), or substituted amino groups (—$NR_2$);

$R_5$, $R_6$ and $R_7$ are independently selected from hydrogen or a group —(CO)—$R_{15}$ with the proviso that two of $R_5$, $R_6$, and $R_7$ are hydrogen and one of $R_5$, $R_6$, and $R_7$ is said group —(CO)—$R_{15}$;

$R_{15}$ is a group —Z or a group —$X^a R^*$ where $X^a$ is oxygen, sulfur, or —$NR^N$—, and $R^*$ is selected from hydrogen, $C_{1-35}$ alkyl, alkenyl, alkynyl, aryl, or aralkyl, each optionally containing up to 20 heteroatoms, or $R^*$ is a group —$R^a$-L, where L is a leaving group for forming a conjugate with an analyte, analyte analog, or binding partner for an analyte; with the proviso that when $R_{15}$ is a group —Z, then X is independently selected at each occurrence from a bond, —$CH_2$—, oxygen, sulfur, or —$NR^N$—;

R is independently selected at each occurrence from $C_{1-35}$ alkyl, alkenyl, alkynyl, aryl, or aralkyl groups each containing up to 20 heteroatoms; and $R^N$ is independently selected at each occurrence from hydrogen, $C_{1-35}$ alkyl, alkenyl, alkynyl, aryl, or aralkyl groups each containing up to 20 heteroatoms;

with the proviso that at least one of $R_1$, $R_2$, $R_3$, $R_5$, $R_6$, and $R_7$ is a group Z.

In another embodiment, the chemiluminescent acridinium compound is an acridinium sulfonamide having the following structure shown in Formula II:

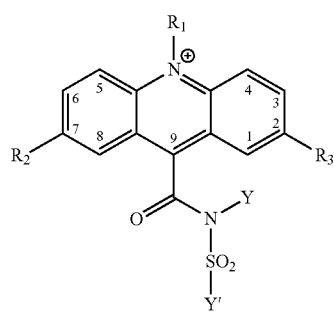

wherein, $R_1$ is a $C_{1-35}$ alkyl, alkenyl, alkynyl or aralkyl group, each of which may contain up to 20 heteroatoms, or a sulfopropyl or sulfobutyl group, or $R_1$ is a group —$R^a$—Z;

$R_2$ and $R_3$ are independently selected from (i) hydrogen, (ii) an electron donating group, or (iii) a group —Z;

Y and Y' are independently selected from R, —$R^a$—Z, or —$R^a$-L; where L is a derivitizable functional group comprising a leaving group, electrophilic group, or nucleophilic group for forming a conjugate with an analyte, analyte analog, or binding partner for an analyte;

Z is a zwitterionic group of the form:

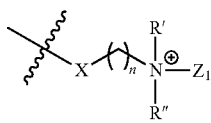

X is independently selected at each occurrence from a bond, —$CH_2$—, oxygen, sulfur, —$NR^N$—, amide (—NH(CO)—), carbamate (—NHC(O)O—), or urea (—NHC(O)NH—);

R' and R" are independently selected at each occurrence from $C_{1-35}$ alkyl, alkenyl, alkynyl, aryl, or aralkyl, each containing up to 20 heteroatoms;

$Z_1$ is a group —$R^a$—$Z_2$ where $Z_2$ is selected from carboxylate (—$COO^-$), sulfonate (—$SO_3^-$), sulfate (—$OSO_3^-$), phosphate (—$OP(O)(OR)(O^-)$), or oxide (—$O^-$); or, in the case where $Z_2$ is an oxide (—$O^-$), $R^a$ may be absent;

n is, independently selected at each occurrence, an integer between one and 12;

R is independently selected at each occurrence from $C_{1-35}$ alkyl, alkenyl, alkynyl, aryl, or aralkyl groups each containing up to 20 heteroatoms;

$R^N$ is independently selected at each occurrence from hydrogen, $C_{1-35}$ alkyl, alkenyl, alkynyl, aryl, or aralkyl groups each containing up to 20 heteroatoms;

and $R^a$ is a divalent radical selected from $C_{1-35}$ alkyl, alkenyl, alkynyl, aryl, or aralkyl group, each optionally containing up to 20 heteroatoms;

with the proviso that at least one of $R_1$, $R_2$, $R_3$, Y and Y' comprises said zwitterionic group Z.

In another aspect of the invention, a reagent is provided for the detection of an analyte comprising a chemiluminescent acridinium compound bound to an analyte, analyte analog, or binding partner for an analyte, the acridinium compound comprising (i) a hydrocarbon group attached to the nitrogen atom of the acridinium nucleus, said hydrocarbon group being optionally substituted with up to 20 heteroatoms, and (ii) a carboxyl or sulfonamide group at the $C_9$ position of the acridinium nucleus linked to a substituted hydrocarbon moiety being optionally substituted with up to 20 heteroatoms, wherein said acridinium compound comprises at least one zwitterionic functional group attached to the $C_2$ position of the acridinium nucleus, the $C_7$ position of the acridinium nucleus, the hydrocarbon moiety linked to the carboxyl or sulfonamide group, or the hydrocarbon group attached to the nitrogen atom of the acridinium nucleus; wherein said acridinium compound exhibits reduced non-specific binding to a solid phase as compared to an otherwise identical acridinium compound not comprising said zwitterionic functional group.

In a further aspect of the invention, an assay is provided for the detection or quantification of a macromolecular analyte comprising: (a) providing a conjugate comprising a chemiluminescent acridinium compound according to the invention bound to a binding molecule specific for an analyte; (b) providing a solid support having immobilized thereon a second binding molecule specific for said analyte; (c) mixing the conjugate, the solid phase and a sample suspected of containing the analyte to form a binding complex; (d) separating the binding complex captured on the solid support; (e) triggering chemiluminescence of the binding complex from step (d) by adding chemiluminescence triggering reagents; (f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In yet another aspect, an assay is provided for the detection or quantification of a small molecule analyte is comprising the steps of: (a) providing a conjugate of an analyte with a chemiluminescent acridinium compound according to the invention; (b) providing a solid support immobilized with a binding molecule specific for the analyte; (c) mixing the conjugate, solid support and a sample suspected of containing the analyte to form a binding complex; (d) separating the binding complex captured on the solid support; (e) triggering the chemiluminescence of the binding complex from step (d) by adding chemiluminescence triggering reagents; (f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

In another aspect still, an assay is provided for the detection of small molecule analyte comprising: (a) providing a solid support immobilized with an analyte or an analyte analog; (b) providing a conjugate of a binding molecule specific for the analyte with a chemiluminescent acridinium compound according to the invention; (c) mixing the solid phase, the conjugate and a sample suspected containing the analyte to form a binding complex; (d) separating the binding complex captured on the solid support; (e) triggering the chemiluminescence of the binding complex of (d) by adding chemiluminescence triggering reagents; (f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

These and other aspect of the invention will be better understood by reference to the following detailed description, including the appended claims.

DETAILED DESCRIPTION

Figure 1:
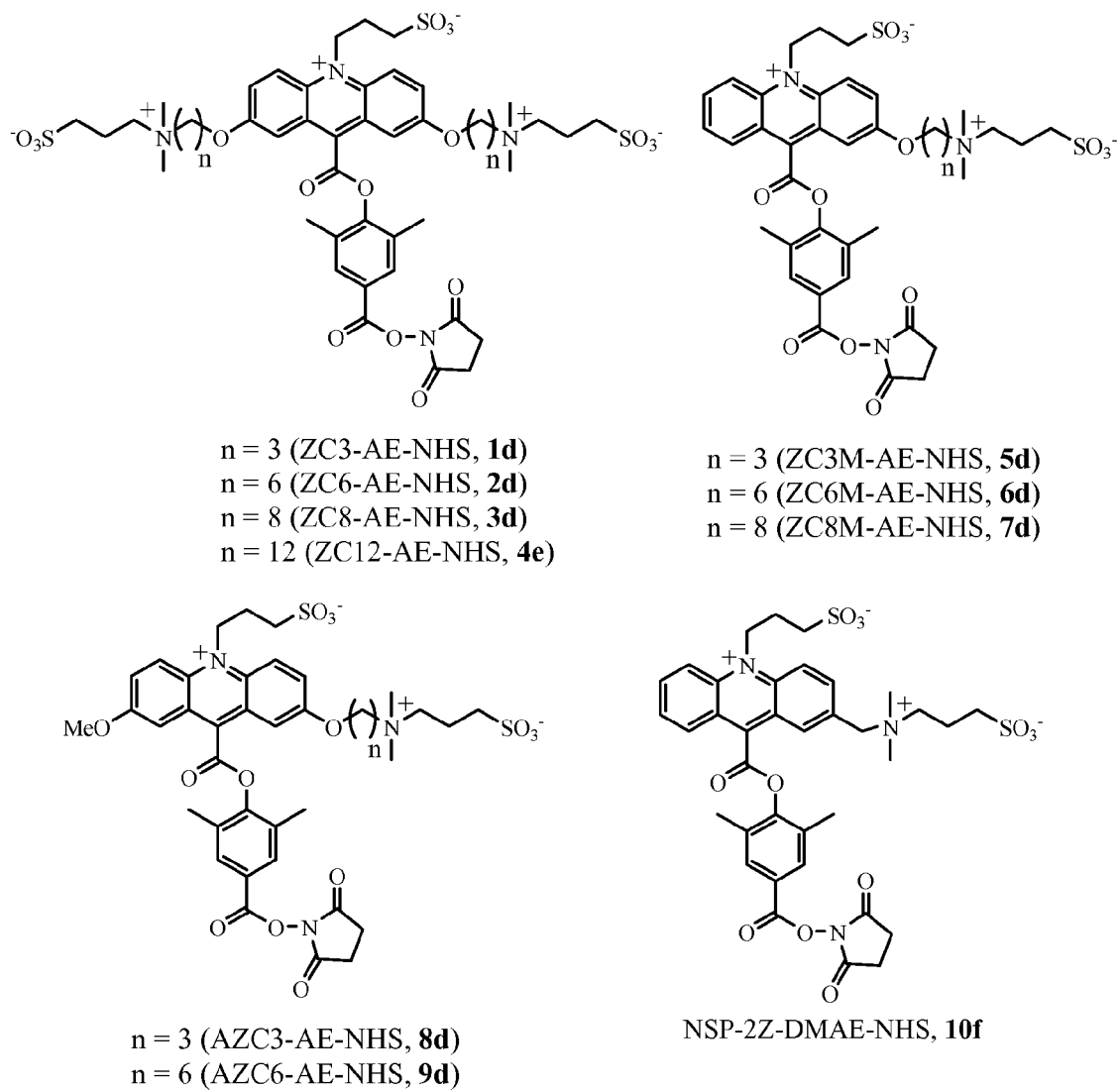
FIG. 1 provides the chemical structures of a plurality of exemplary zwitterion-containing acridinium compounds of the present invention.
Figure 2:
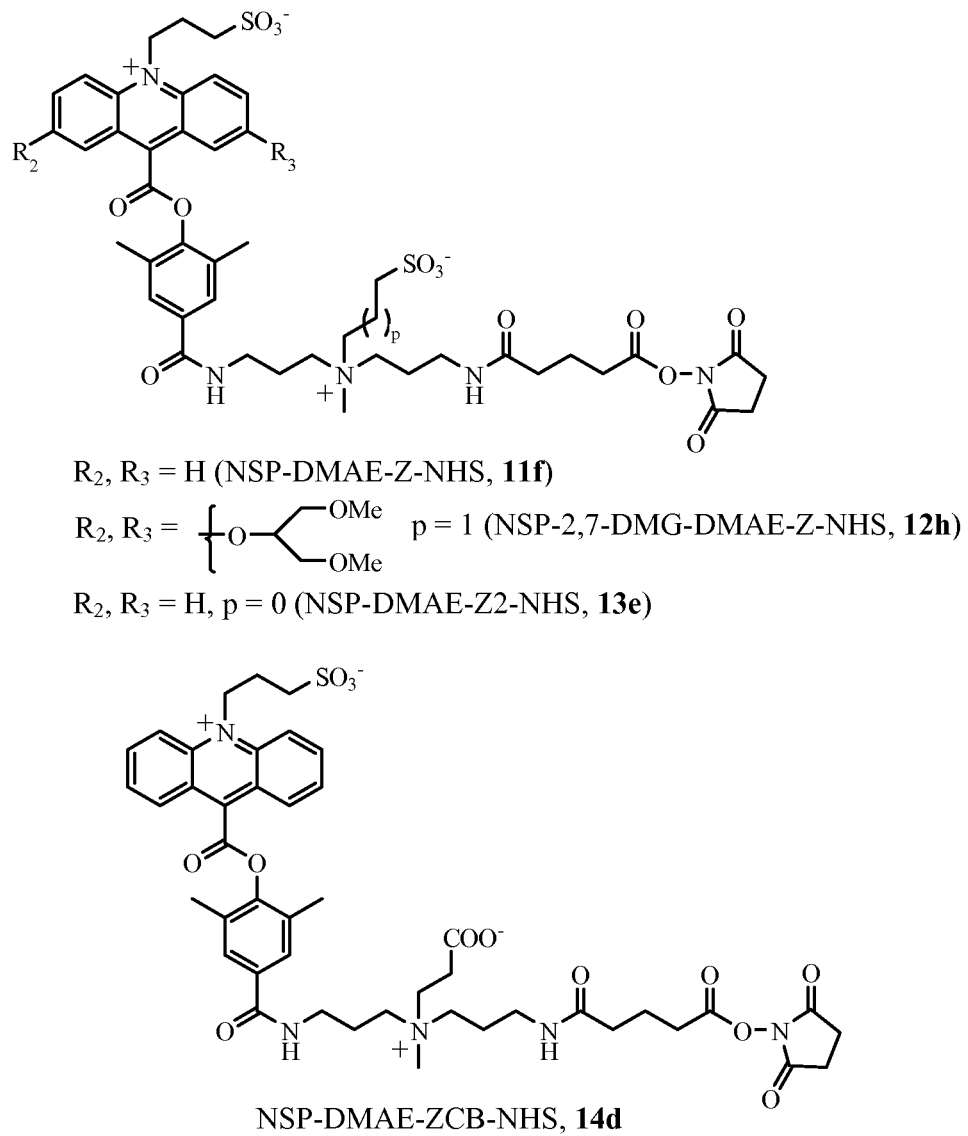
FIG. 2 provides the chemical structures of other exemplary zwitterion-containing acridinium compounds of the present invention.

The main objective of this invention is to disclose structures of zwitterion-containing acridinium compounds that display low non-specific binding to solid phases when compared to acridinium compounds lacking these structural features. Another objective of this invention is to disclose two types of zwitterion modification of acridinium compounds:

(a) acridinium compounds containing zwitterions in the acridinium ring and, (b) acridinium compounds containing zwitterions attached to the phenol leaving group. Another objective of the current invention is to disclose unexpectedly faster light emission from acridinium compounds with zwitterions attached to the phenol when compared to acridinium compounds without this structural modification. Yet another objective of the current invention is to demonstrate that zwitterion-containing acridinium compounds are as stable as acridinium compounds without zwitterions and have comparable quantum yields.

The chemiluminescent acridinium compounds according to the invention may be acridinium esters, acridinium sulfonamides, or the like. In one embodiment, chemiluminescent acridinium compounds comprise (i) a hydrocarbon group attached to the nitrogen atom of the acridinium nucleus, the hydrocarbon group being optionally substituted with up to 20 heteroatoms, and (ii) a carboxyl or sulfonamide group at the $C_9$ position of the acridinium nucleus linked to a substituted hydrocarbon moiety, wherein the acridinium compound comprises at least one zwitterionic functional group attached to the $C_2$ position of the acridinium nucleus, the $C_7$ position of the acridinium nucleus, the hydrocarbon moiety linked to the carboxyl or sulfonamide group, or the hydrocarbon group attached to the nitrogen atom of the acridinium nucleus; wherein said acridinium compound exhibits reduced non-specific binding to a solid phase as compared to an otherwise identical acridinium compound not comprising said zwitterionic functional group.

The hydrocarbon group attached to the nitrogen atom is optionally substituted with up to 20 heteroatoms and therefore may, itself, constitute a zwitterionic group, for example in the case of a sulfopropyl or sulfobutyl group attached the ring nitrogen where there is a positive charge on the quaternary ring nitrogen and a negative charge on the —$SO_3$ group. It will be understood that even if such a zwitterionic group is present, the compounds according to the invention will comprise at least one zwitterionic group in addition. Put another way, the compounds according to the invention will comprise a positive charge on an atom other than, or in addition to, the nitrogen of the acridinium nucleus.

In one embodiment, the chemiluminescent acridinium compound is an acridinium ester having the following structure shown in Formula I:

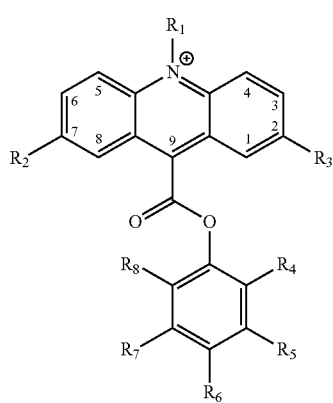

I wherein,
$R_1$ is a $C_{1-35}$ alkyl, alkenyl, alkynyl or aralkyl group, each of which may contain up to 20 heteroatoms, or a sulfopropyl or sulfobutyl group, or $R_1$ is a group —$R^a$—Z; where $R^a$ is a divalent radical selected from $C_{1-35}$ alkyl, alkenyl, alkynyl, aryl, or aralkyl group, each optionally containing up to 20 heteroatoms;

$R_2$ and $R_3$ are independently selected from (i) hydrogen, (ii) an electron donating group, or (iii) a group —Z;
Z is a zwitterionic group of the form:

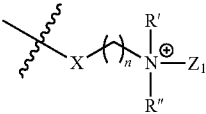

X is independently selected at each occurrence from a bond, —$CH_2$—, oxygen, sulfur, —$NR^N$—, amide (—$NR^N$(CO)—), carbamate (—$NR^N C(O)O$—), or urea (—$NR^N C(O)NR^N$—);

R' and R" are independently selected at each occurrence from $C_{1-35}$ alkyl, alkenyl, alkynyl, aryl, or aralkyl, each optionally containing up to 20 heteroatoms;

$Z_1$ is a group —$R^a$—$Z_2$ where $Z_2$ is selected from carboxylate (—$COO^-$), sulfonate (—$SO_3^-$), sulfate (—$OSO_3^-$), phosphate (—$OP(O)(OR)(O^-)$), or oxide (—$O^-$); or, in the case where $Z_2$ is an oxide (—$O^-$), $R^a$ may be absent;

n is, independently selected at each occurrence, an integer between one and 12; and $R_4$ and $R_8$ are the same or different and are selected from hydrogen, $C_{1-35}$ alkyl, alkenyl, alkynyl, alkoxyl (—OR), alkylthiol (—SR), or substituted amino groups (—$NR_2$);

$R_5$, $R_6$ and $R_7$ are independently selected from hydrogen or a group —(CO)—$R_{15}$ with the proviso that two of $R_5$, $R_6$, and $R_7$ are hydrogen and one of $R_5$, $R_6$, and $R_7$ is said group —(CO)—$R_{15}$;

$R_{15}$ is a group —Z or a group —$X^a R^*$ where $X^a$ is oxygen, sulfur, or —$NR^N$—, and $R^*$ is selected from hydrogen, $C_{1-35}$ alkyl, alkenyl, alkynyl, aryl, or aralkyl, each optionally containing up to 20 heteroatoms, or $R^*$ is a group —$R^a$-L, where L is a leaving group for forming a conjugate with an analyte, analyte analog, or binding partner for an analyte; with the proviso that when $R_{15}$ is a group —Z, then X is independently selected at each occurrence from a bond, —$CH_2$—, oxygen, sulfur, or —$NR^N$—;

R is independently selected at each occurrence from $C_{1-35}$ alkyl, alkenyl, alkynyl, aryl, or aralkyl groups each containing up to 20 heteroatoms; and $R^N$ is independently selected at each occurrence from hydrogen, $C_{1-35}$ alkyl, alkenyl, alkynyl, aryl, or aralkyl groups each containing up to 20 heteroatoms;

with the proviso that at least one of $R_1$, $R_2$, $R_3$, $R_5$, $R_6$, and $R_7$ is a group Z.

In one embodiment, at least one, or exactly one of, $R_1$, $R_2$, $R_3$, and $R_6$ comprises a group -L or —$R^a$-L, where L is a derivitizable functional group comprising a leaving group, electrophilic group, or nucleophilic group for forming a conjugate with an analyte, analyte analog, or binding partner for an analyte. In some embodiments, L will be selected from the group consisting of:

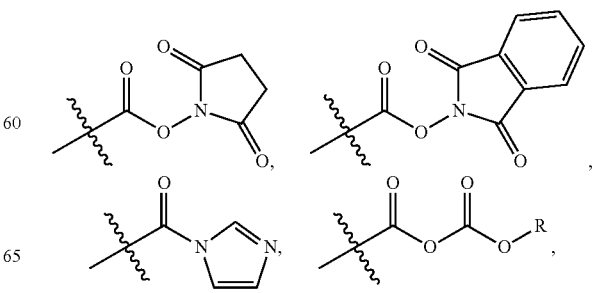

-continued

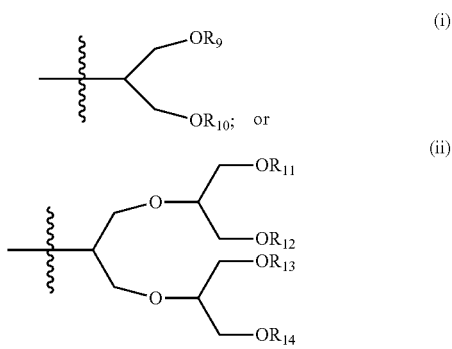

In certain embodiments, $R_{15}$ will be selected from the group consisting of:
(1) —OH;
(2) —O—N-succinimidyl;
(3) —NH—$(CH_2)_5$—C(O)—O—N-succinimidyl;
(4) —NH—$(CH_2)_5$—COOH;
(5) —NH—$(C_2H_4O)_i$—$C_2H_4$NH—C(O)—$(CH_2)_3$—C(O)—O—N-succinimidyl where i=1 to 5;
(6) —NH—$(C_2H_4O)_i$—$C_2H_4$NH—C(O)—$(CH_2)_3$—COOH, wherein i=1 to 5;
(7) —NH—$(C_2H_4O)_i$—$C_2H_4NH_2$, wherein i=1 to 5; and
(8) —NH—R—NHR; and
(9) —Z.

Particular mention may be made of the case where $R_{15}$ is —OH.

In one embodiment, R' or R" comprises a group —$R^a$-L, where L is a derivitizable leaving group, electrophilic group, or nucleophilic group for forming a conjugate with an analyte, analyte analog, or binding partner for an analyte. In some embodiments, L will be selected from the group provided above. In one embodiment, R' or R" is, at one occurrence, a group —$R^a$—C(O)—$CH_2CH_2CH_2$—C(O)—N-succinimidyl, —$R^a$—N-maleimido, —$R^a$—C(O)—$CH_2$—Br, or —$R^a$—C(O)—$CH_2$—I.

In some embodiments, $R_2$ and $R_3$ are both hydrogen. In other embodiment, $R_2$ and/or $R_3$ may be selected, for example, from electron donating groups. Typical electron donating groups include, without limitation, OR, OH, SR, SH, $NH_2$, $NR^NR^N$; wherein R and $R^N$ are independently selected at each occurrence and are selected from the group consisting of hydrogen alkyl, alkenyl, alkynyl, aryl, and aralkyl, each containing up to 20 heteroatoms. A preferred electron donating group is alkoxyl (—OR).

In some embodiments, $R_2$ and/or $R_3$ may be selected from the group consisting of (i) alkoxyl (—OR), (ii) a group —O—$(CH_2CH_2$—O$)_l$—$CH_3$ where l is an integer from 1 to 12, and (iii) a group —O-G, and (vi) a group —Z; where G is a branched group independently selected at each occurrence from:

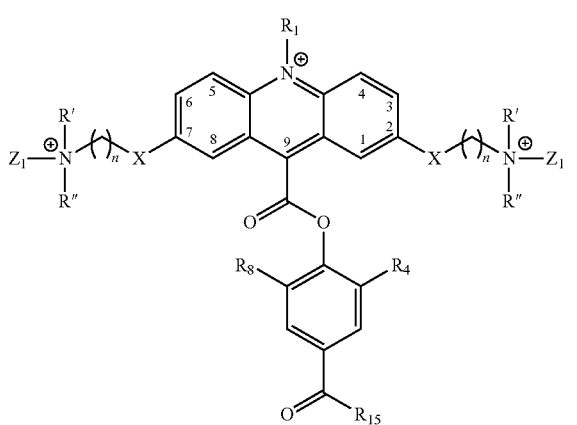

where $R_9$, $R_{10}$, $R_{11}$ $R_{12}$, $R_{13}$ and $R_{14}$ are independently at each occurrence a methyl group or a group —$(CH_2CH_2O)_m$ $CH_3$, where m is an integer from 1 to 5.

In one embodiment, the chemiluminescent acridinium ester compound according to the invention will have the structure shown in Formula Ia:

Ia where $R_1$, $R_4$, $R_8$, $R_{15}$, R', R", X, $Z_1$, and n are as defined in Formula I, and R', R", X, $Z_1$, and n are independently selected at each occurrence.

In particular embodiments, $R_1$ may suitably be an alkyl group, a sulfopropyl group, or a sulfobutyl group, $R_4$ and $R_8$ may be lower alkyl, in particular methyl, X may be oxygen, and/or $Z_1$ may be —$SO_3$. In one embodiment, the acridinium ester according to Formula Ia will have the following structure:

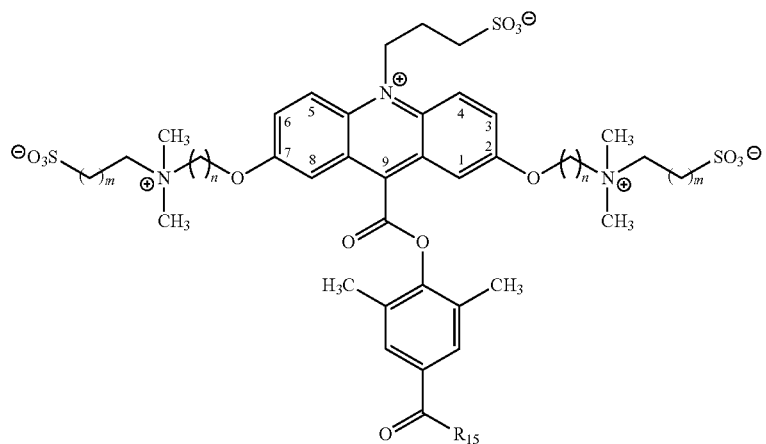

wherein, m is an integer from 0 (zero) to 3 and $R_{15}$ and n are as defined above for Formula I, with m and n being independently selected at each occurrence. In one embodiment, the compound will have the following structure:

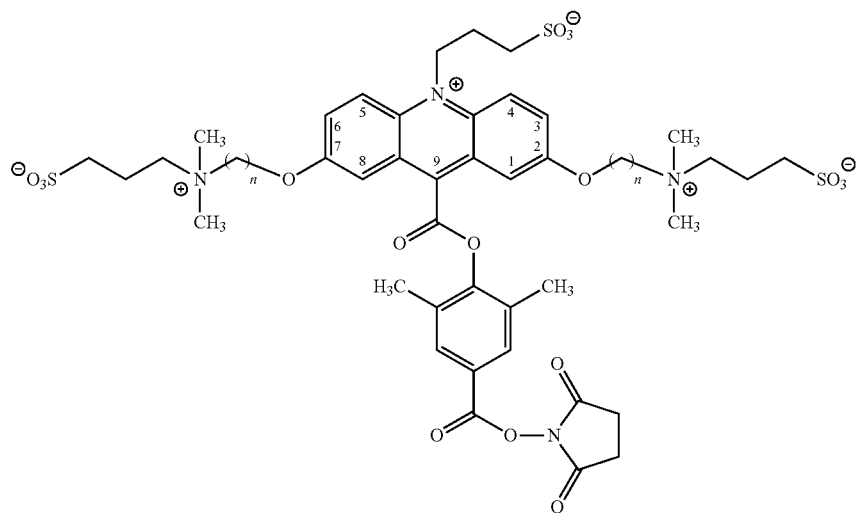

wherein n is an integer from 1 to 12, independently selected at each occurrence.

Another representative acridinium ester compound according to Formula I has the structure shown in Formula Ib:

where $R_1$, $R_2$, $R_4$, $R_8$, $R_{15}$, R', R", X, $Z_1$, and n are as defined above. In one embodiment, the chemiluminescent acridinium ester compound of Formula Ib has the following structure:

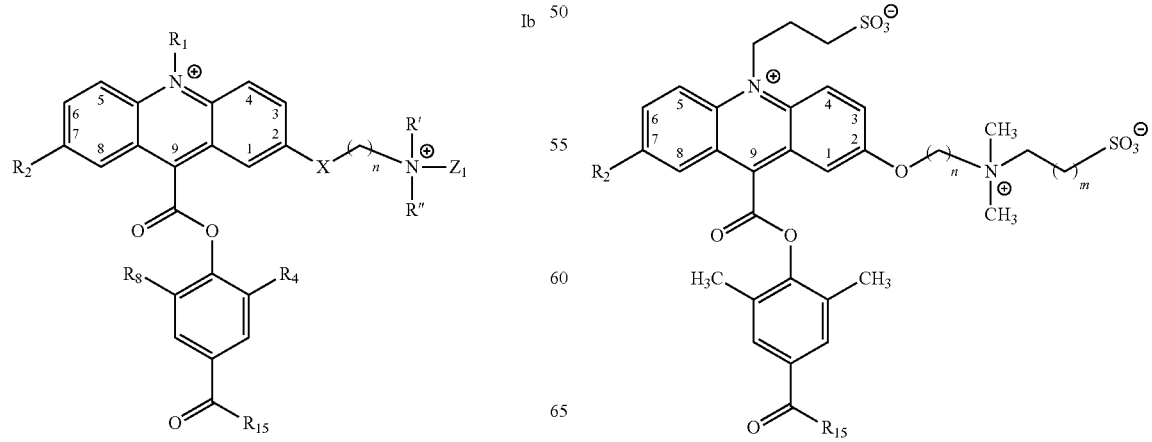

wherein, m is an integer from 0 (zero) to 3 and $R_2$, $R_{15}$ and n are as defined above. In one embodiment, an acridinium ester compound according to the invention has the following structure:

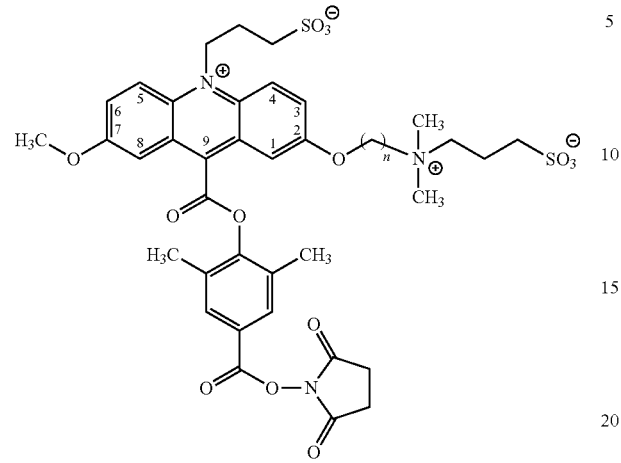

wherein n is an integer from 1 to 12. having the following structure:

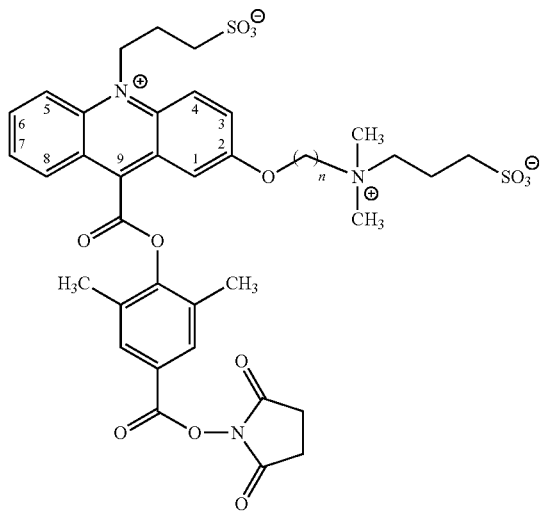

wherein n is an integer from 1 to 12. Yet another compound according to Formula IB has the following structure:

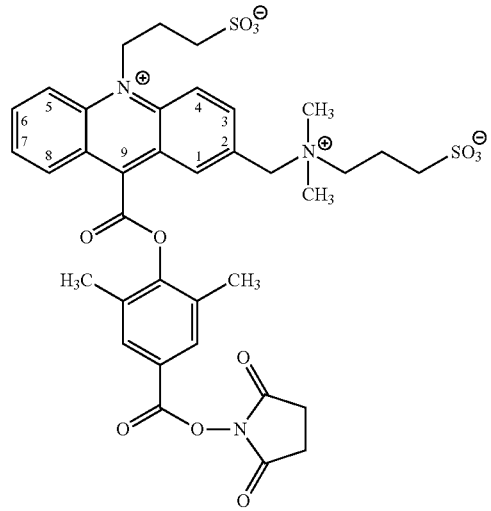

and represents the case where X is a bond (i.e., X is absent altogether) or a methylene unit —$CH_2$—.

Another example of a chemiluminescent acridinium ester compound according to Formula I, has the structure shown in Formula Ic:

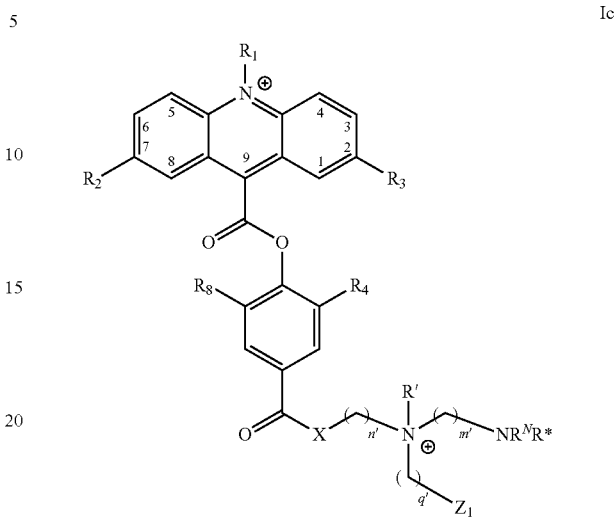

wherein n', m', and q' are independently an integer from 1-4, and $R_1$, $R_2$, $R_3$, $R_4$, $R_8$, $R^N$, $R^*$, $R'$ X, and $Z_1$ are as defined above. In one embodiment, $R^*$ comprises a group —$R^a$-L, where L is a leaving group for forming a conjugate with an analyte, analyte analog, or binding partner for an analyte. A representative compound according to this embodiment has the following structure:

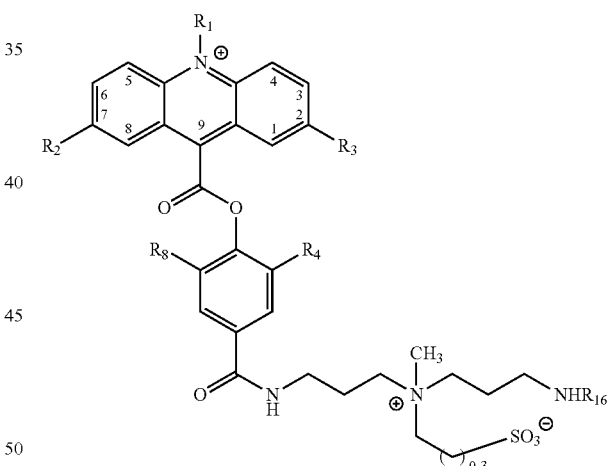

wherein $R_1$, $R_2$, $R_3$, $R_4$, and $R_8$ are as defined above. In some embodiments $R_4$ and $R_4$ are independently lower alkyl groups, and in particular methyl; $R_1$ is alkyl (e.g., methyl), sulfopropyl (—$CH_2CH_2CH_2$—$SO_3^-$)$_5$ or sulfobutyl (—$CH_2CH_2CH_2CH_2$—$SO_3^-$); $R_2$ and $R_3$ are selected independently from hydrogen or a group —O-G, where G is defined as above; and $R_{16}$ is selected from (i) hydrogen, (ii) —C(O)—$CH_2CH_2CH_2$—C(O)—N-succinimidyl, (iii) —R—N-maleimido where R is independently alkyl, alkenyl, alkynyl, or aralkyl, each of which may optionally comprise up to 20 heteroatoms, or (iv) —C(O)—$CH_2$—X where X is bromine (Br) or iodine (I).

In one embodiment, a chemiluminescent acridinium compound according to Formula Ic, has the following structure:

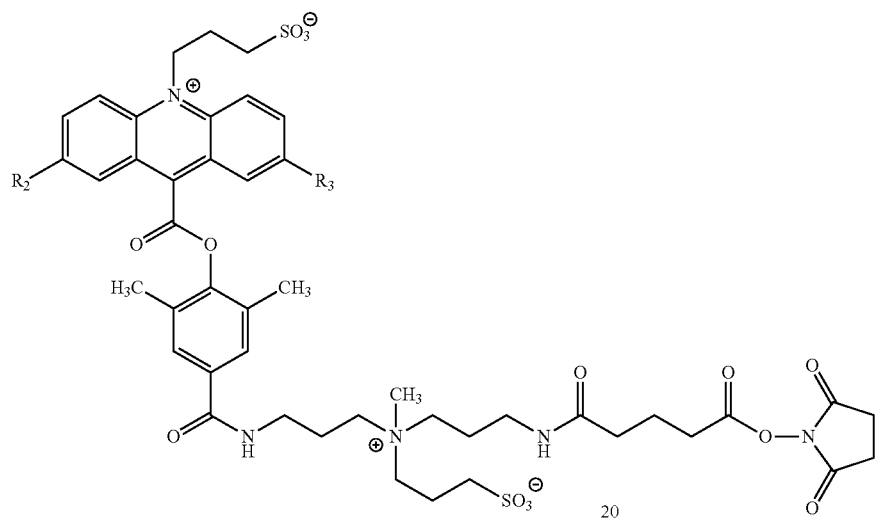

wherein R₂ and R₃ are as defined as above. In one embodiment, R₂ and R₃ are independently selected from hydrogen or a group —O-G, where G is as defined herein.

Id

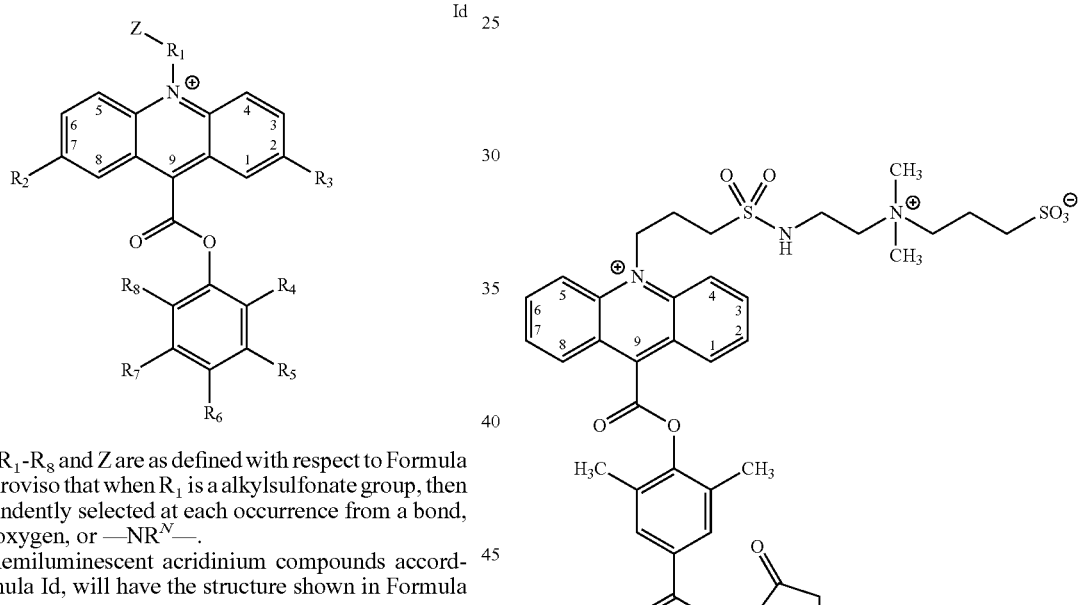

wherein R₁-R₈ and Z are as defined with respect to Formula I; with the proviso that when R₁ is a alkylsulfonate group, then X is independently selected at each occurrence from a bond, —CH₂—, oxygen, or —NR$^N$—.

Some chemiluminescent acridinium compounds according to Formula Id, will have the structure shown in Formula Ie:

Ie wherein R₂, R₃, R₄, R₈, R₁₅, R', R", R$^N$, Z₁ and n are as defined in Formula I. An exemplary compound according to Formula Ie has the following structure:

wherein the compound optionally includes a counterion A to balance the positively charged nitrogen of the acridinium nucleus. While there is essentially no limitation on the selection of counterion, in some embodiments A- is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

An exemplary chemiluminescent acridinium compound according to Formula Ie (also shown in FIG. 3) has two zwitterionic groups, according to the following structure:

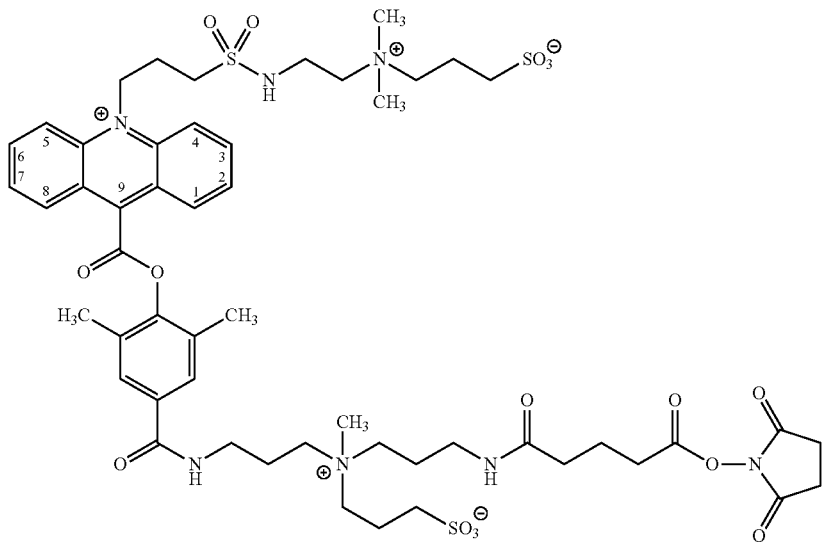

wherein the compound optionally includes a counterion A to balance the positively charged nitrogen of the acridinium nucleus.

In addition to the acridinium esters described above, the invention also embraces other acridinium compounds capable of undergoing chemiluminescence, including, for example, acridinium sulfonamides. In some embodiments, acridinium sulfonamides according to the invention will have the structure of Formula II:

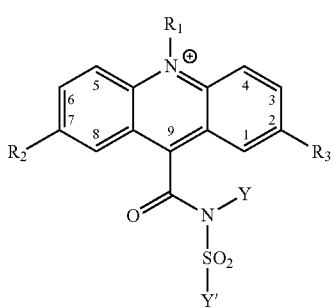

wherein, $R_1$ is a $C_{1-35}$ alkyl, alkenyl, alkynyl or aralkyl group, each of which may contain up to 20 heteroatoms, or a sulfopropyl or sulfobutyl group, or $R_1$ is a group —$R^a$—Z;

$R_2$ and $R_3$ are independently selected from (i) hydrogen, (ii) an electron donating group, or (iii) a group —Z;

Y and Y' are independently selected from R, —$R^a$—Z, or —$R^a$-L; where L is a derivitizable functional group comprising a leaving group, electrophilic group, or nucleophilic group for forming a conjugate with an analyte, analyte analog, or binding partner for an analyte;

Z is a zwitterionic group of the form:

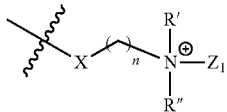

X is independently selected at each occurrence from a bond, —$CH_2$—, oxygen, sulfur, —$NR^N$—, amide (—NH(CO)—), carbamate (—NHC(O)O—), or urea (—NHC(O)NH—);

R' and R" are independently selected at each occurrence from $C_{1-35}$ alkyl, alkenyl, alkynyl, aryl, or aralkyl, each containing up to 20 heteroatoms;

$Z_1$ is a group —$R^a$—$Z_2$ where $Z_2$ is selected from carboxylate (—$COO^-$), sulfonate (—$SO_3^-$), sulfate (—$OSO_3^-$), phosphate (—$OP(O)(OR)(O^-)$), or oxide (—$O^-$); or, in the case where $Z_2$ is an oxide (—$O^-$), $R^a$ may be absent;

n is, independently selected at each occurrence, an integer between one and 12; and R is independently selected at each occurrence from $C_{1-35}$ alkyl, alkenyl, alkynyl, aryl, or aralkyl groups each containing up to 20 heteroatoms;

$R^N$ is independently selected at each occurrence from hydrogen, $C_{1-35}$ alkyl, alkenyl, alkynyl, aryl, or aralkyl groups each containing up to 20 heteroatoms; and $R^a$ is a divalent radical selected from $C_{1-35}$ alkyl, alkenyl, alkynyl, aryl, or aralkyl group, each optionally containing up to 20 heteroatoms;

with the proviso that at least one of $R_1$, $R_2$, $R_3$, Y and Y' comprises said zwitterionic group Z.

In some embodiments of the acridinium sulfonamides according to Formula II, L is a functional group which enables the a compound to form a conjugate with an analyte, analyte analog, binding partner for an analyte, etc., and may be selected from the group consisting of:

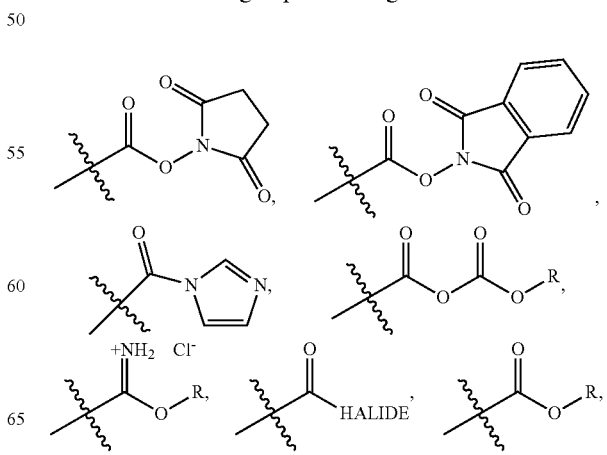

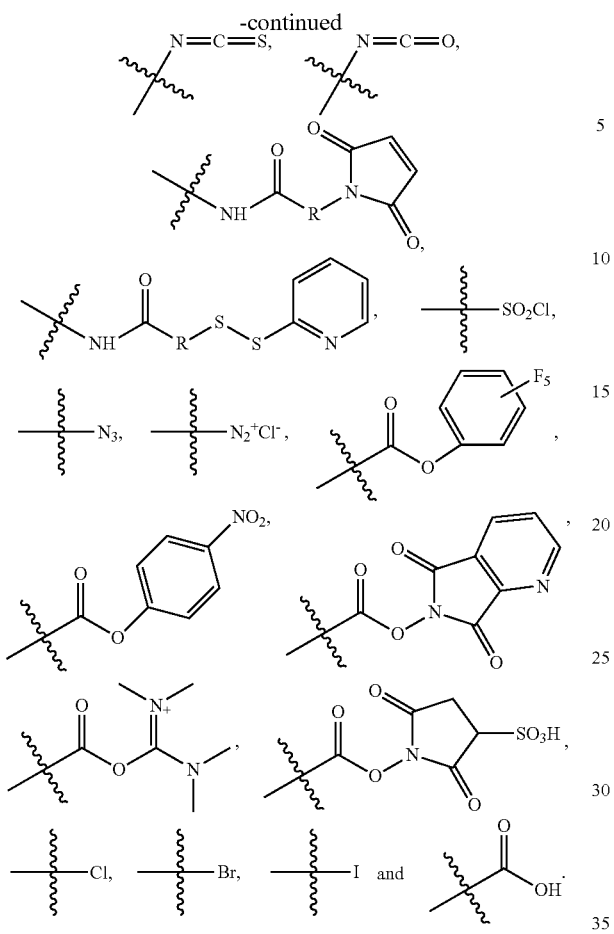

In some embodiments, R' or R" comprises a group —$R^a$-L. In other embodiments, R' or R" is, at one occurrence, a group a group —$R^a$—C(O)—CH$_2$CH$_2$CH$_2$—C(O)—N-succinimidyl, —$R^a$—N-maleimido, —$R^a$—C(O)—CH$_2$—Br, or —$R^a$—C(O)—CH$_2$—I.

In additional embodiments of the chemiluminescent acridinium sulfonamide compounds according to Formula II, $R_1$ will be selected from methyl, sulfopropyl (—CH$_2$CH$_2$CH$_2$—SO$_3^-$), sulfobutyl (—CH$_2$CH$_2$CH$_2$CH$_2$—SO$_3^-$), or a group having the structure:

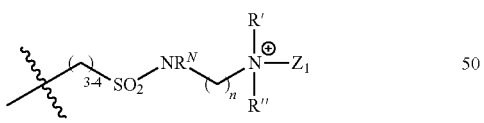

where $R^N$, R', R", $Z_1$, and n are as defined for Formula II.

One or both of $R_2$ and $R_3$ may be, for example, a group Z, and more particularly, one or both of $R_2$ and $R_3$ may be a group:

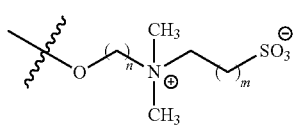

where n is an integer from 1-12 and m is an integer from 0-3.

In preferred chemiluminescent acridinium sulfonamide compounds according to Formula II, Y' will comprise an aryl group, or alkyl-aryl group, or aryl, alky group, each being optionally substituted with up to 20 heteroatom. One such acridinium sulfonamide compound has the structure of Formula IIb:

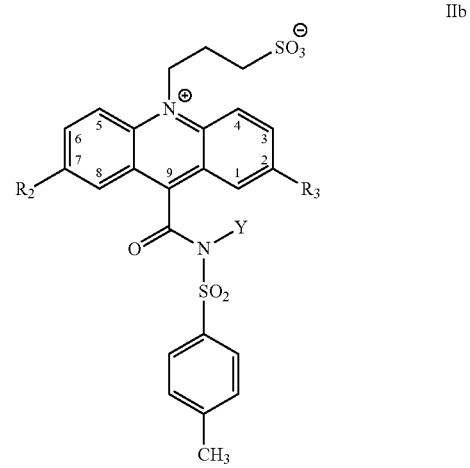

IIb wherein Y comprises a group —$R^a$—Z, where $R^a$, $R_2$, $R_3$, and Z are as defined above.

Other chemiluminescent acridinium sulfonamide compounds according to Formula II, have the structure of Formula IIc:

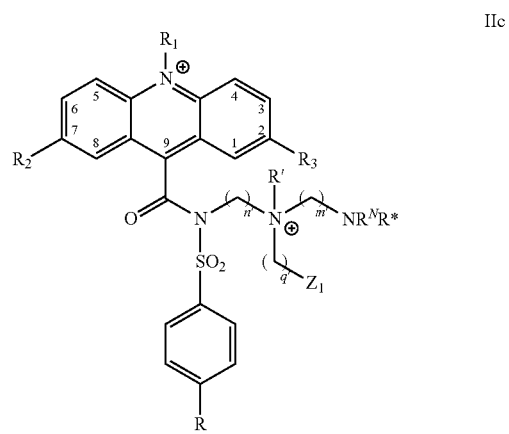

IIc wherein R* is selected from hydrogen, $C_{1-35}$ alkyl, alkenyl, alkynyl, aryl, or aralkyl, each optionally containing up to 20 heteroatoms, or R* is a group —$R^a$-L, where L is a leaving group for forming a conjugate with an analyte, analyte analog, or binding partner for an analyte; n', m', and q' are independently integers from 1-4, and R, $R^N$, $R_1$, $R_2$, $R_3$, R' and $Z_1$ are as defined above.

It will be understood the selection of substituents $R_1$, $R_2$, $R_3$, $R^N$, R*, R', R", Z, X, n, m, etc., including the preferences therefore, defined in connection with Formula I, apply equally to the selection of comparable parameters in accordance with Formula II.

Zwitterion-containing acridinium compounds of the current invention display low non-specific binding when conjugated to proteins such as antibodies. Non-specific binding, as described earlier, in assays using solid phases such as particles or microtiter plates are undesired binding interactions of conjugates to these solid phases. These undesired binding interactions typically increase the background of the assay leading to a net lowering of the signal to background ratio in the assay and thereby decreasing assay sensitivity. To evaluate the non-specific binding of the various zwitterion-containing acridinium compounds of the current invention, we prepared antibody conjugates of these compounds using a murine, monoclonal antibody (anti-TSH Mab) raised against the analyte TSH (Thyroid Stimulating Hormone). The non-specific binding of these conjugates was then compared to the non-specific binding of analogous conjugates prepared using NSP-DMAE-HEG and HQYAE. The latter two hydrophilic acridinium esters, as mentioned earlier and described in U.S. Pat. No. 6,664,043 B2 and U.S. Pat. No. 7,309,615 B2 respectively, contain hexa(ethylene)glycol attached to the phenol and the acridinium ring respectively. The latter compound, HQYAE, also has increased light output (higher quantum yield) because of the two alkoxy, electron-donating groups in the acridinium ring as described in U.S. Pat. No. 7,309,615 B2. Non-specific binding was measured on two different kinds of particles; paramagnetic particles (PMP) and magnetic latex particles (MLP) from a commercial vendor (Dynal™). The two particles differ in their intrinsic composition. PMPs are made mainly of iron oxide particles with a silane coating containing amines. The amines are used to cross-link proteins to the particle surface using reagents such as glutaraldehyde. MLPs on the other hand are made of porous polystyrene with doped-in magnetite to enable magnetic separation. The PMP used in the current evaluation was coated with an anti-TSH antibody on the particle surface using glutaraldehyde coupling chemistry (Solid Phase "PMP"). The MLPs used for the current evaluation (Dynal M280-streptavidin bound biotinylated polyclonal goat anti-PTH antibody (Solid Phase "M280") and Dynal M270-streptavidin bound biotinylated monoclonal mouse anti-cTnI antibody (Solid Phase "M270")) had immobilized streptavidin on the surfaces which were then used to further immobilize biotin-labeled antibodies capable of binding the analytes PTH (parathyroid hormone) or cTNI (cardiac troponin I). The streptavidin-biotin binding interaction is well known and is commonly used in assays. The two types of particles (PMPs and MLPs) were mixed with solutions of the conjugates for a specific period of time and then the particles were magnetically separated, washed once and then the chemiluminescence associated with the particles was measured. (Experimental details can be found in Example 18.) The ratio of this chemiluminescence value in comparison to the total chemiluminescence input is referred to fraction non-specific binding (fNSB). Conjugates with low non-specific binding will thus have low fNSB values and these values of exemplary embodiments of the zwitterion-containing acridinium compounds of the current invention (further described below), along with the control compounds, are tabulated below in Table 1.

TABLE 1

| | Acridinium Compounds | # of Labels in Conjugate | Solid Phase | | |
|---|---|---|---|---|---|
| | | | PMP | M280 | M270 |
| Controls | NSP-DMAE-HEG | 5 | $4.0 \times 10^{-5}$ | $5.2 \times 10^{-4}$ | $4.6 \times 10^{-4}$ |
| | HQYAE | 6 | $1.6 \times 10^{-5}$ | $1.5 \times 10^{-4}$ | $1.3 \times 10^{-4}$ |
| 1d | ZC3-AE | 7 | $2.0 \times 10^{-5}$ | $1.6 \times 10^{-5}$ | $1.5 \times 10^{-5}$ |
| 5d | ZC3M-AE | 7 | $3.4 \times 10^{-5}$ | $2.2 \times 10^{-5}$ | $1.7 \times 10^{-5}$ |
| 2d | ZC6-AE | 5 | $2.8 \times 10^{-5}$ | $1.9 \times 10^{-5}$ | $1.6 \times 10^{-5}$ |
| 6d | ZC6M-AE | 6 | $3.7 \times 10^{-5}$ | $3.4 \times 10^{-5}$ | $3.3 \times 10^{-5}$ |
| 3d | ZC8-AE | | $2.4 \times 10^{-5}$ | $3.2 \times 10^{-5}$ | $2.7 \times 10^{-5}$ |
| 7d | ZC8M-AE | 7 | $3.9 \times 10^{-5}$ | $5.7 \times 10^{-5}$ | $3.9 \times 10^{-5}$ |
| 4e | ZC12-AE | 5 | $3.3 \times 10^{-5}$ | $1.7 \times 10^{-4}$ | $1.8 \times 10^{-4}$ |
| 11f | NSP-DMAE-Z | 5 | $1.3 \times 10^{-5}$ | $1.6 \times 10^{-5}$ | $1.3 \times 10^{-5}$ |
| 10f | NSP-2Z-DMAE | 6 | $1.3 \times 10^{-5}$ | $1.2 \times 10^{-5}$ | $1.1 \times 10^{-5}$ |
| 8d | AZC3-AE | 6 | $6.2 \times 10^{-6}$ | $2.0 \times 10^{-5}$ | $1.6 \times 10^{-5}$ |
| 9d | AZC6-AE | 5 | $1.0 \times 10^{-5}$ | $1.4 \times 10^{-5}$ | $1.5 \times 10^{-5}$ |

PMP = PMP-anti-TSH antibody
M280 = Dynal M280-streptavidin bound biotinylated polyclonal goat anti-PTH antibody
M270 = Dynal M270-streptavidin bound biotinylated monoclonal mouse anti-cTnI antibody The NSP-DMAE-HEG and HQYAE conjugates on PMP have fNSB values of $4 \times 10^{-5}$ and $1.6 \times 10^{-5}$ respectively. All the other conjugates made using the zwitterion-containing acridinium esters of the current invention have fNSB values that are comparable to or lower than these values. For example, the conjugates derived from NSP-DMAE-Z and ZC6M-AE have fNSB values of $1.3 \times 10^{-5}$ and $3.7 \times 10^{-5}$ respectively. The former acridinium ester contains the zwitterion attached to the phenol, whereas the latter compound contains a zwitterion in the acridinium ring. Both types of zwitterion modification are thus effective in reducing fNSB to PMP particles. On the Dynal MLP with the anti-PTH antibody on the particle surface, the NSP-DMAE-HEG and HQYAE conjugates have fNSB values of $5.2 \times 10^{-4}$ and $1.5 \times 10^{-4}$ respectively. All the other conjugates derived from the zwitterion-containing acridinium esters have fNSB values that are substantially lower with the exception of ZC12-AE whose fNSB ($1.7 \times 10^{-4}$) is comparable to that of the HQYAE conjugate. A similar result is observed on the Dynal MLP with the anti-cTNI antibody immobilized on its surface. Zwitterion-containing acridinium ester conjugates thus have significantly lower fNSB values on the MLPs that were currently tested and, offer the potential to improve assay sensitivity by reducing background signal as discussed earlier.

Figure 3:
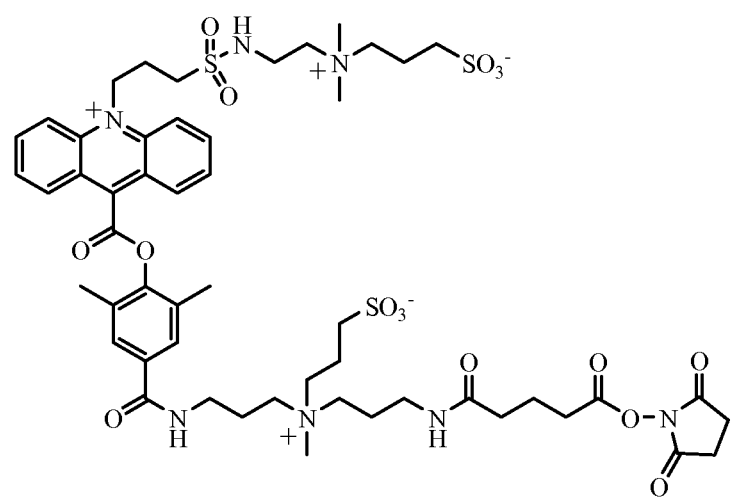
FIG. 3 provides the chemical structures of another exemplary zwitterion-containing acridinium compound of the present invention.
Figure 4:
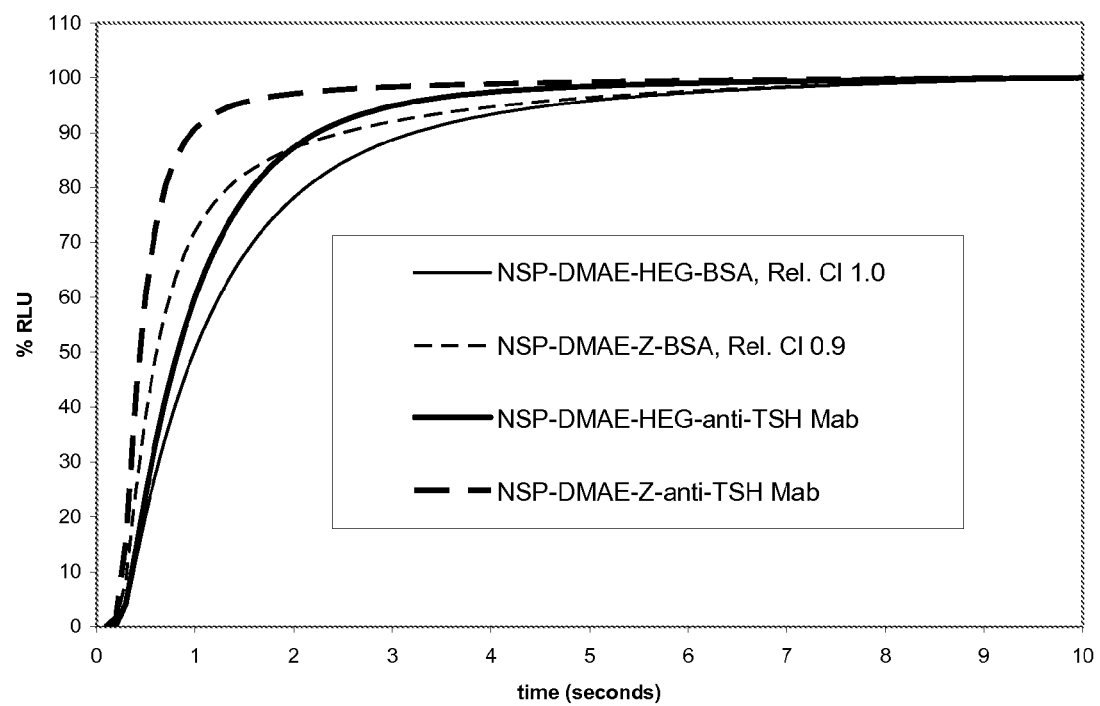
FIG. 4 is a plot of the light emitted from control (NSP-DMAE-HEG) and exemplary zwitterion-containing acridinium (NSP-DMAE-Z-NHS) conjugates in percent Relative Light Units (RLUs), plotted as a function of time.

The acridinium ester conjugates of NSP-DMAE-Z and NSP-2,7-DMG-DMAE-Z (DMG=dimethoxyglyceryloxy) with zwitterions attached to the phenol also unexpectedly exhibit faster light emission when compared to the analogous conjugates derived from NSP-DMAE-HEG and HQYAE respectively as illustrated in the graphs in FIGS. 3 & 4. The acridinium ester, NSP-DMAE-Z-NHS is analogous to NSP-DMAE-HEG-glutarate-NHS in that both acridinium esters contain the same acridinium ring but different functional groups attached to the phenol. The former compound contains a zwitterion attached to the phenol whereas the latter compound contains a hexa(ethylene)glycol derivative. The zwitterion-containing compound NSP-2,7-DMG-DMAE-Z-NHS, in addition to containing the zwitterion attached to the phenol also has electron-donating dimethoxyglyceryloxy (DMG) functional groups in the acridinium ring. The light output from this compound is similar to that of HQYAE because of the two electron-donating groups and, is higher than that of NSP-DMAE-HEG.

Light measurements were made on a luminometer and the light emitted from each conjugate (expressed as RLUs; Relative Light Units) was measured at various time intervals. The total light emitted from each conjugate was then used to calculate the percent light emitted (% RLU) at each time interval. As is evident from FIG. 4, the anti-TSH Mab (Mab=Monoclonal antibody) conjugate of NSP-DMAE-HEG requires >4 seconds for complete light emission whereas for the conjugate of NSP-DMAE-Z, light emission is complete within two seconds. A similar comparison of the BSA conjugates (BSA=bovine serum albumin), of the two acridinium esters indicates significantly faster light emission for the zwitterion-containing acridinium ester.

Figure 5:
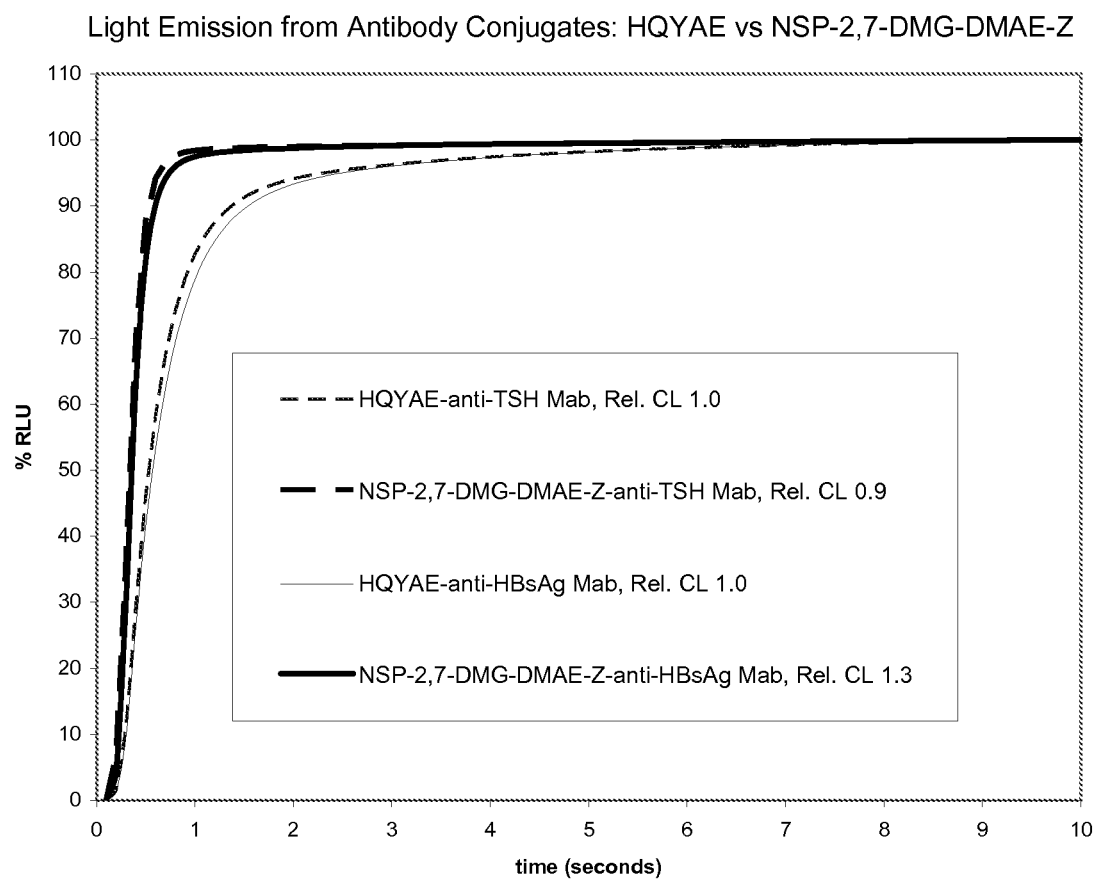
FIG. 5 is a plot of the light emitted from control (HQYAE) and exemplary zwitterion-containing acridinium (NSP-2,7-DMG-DMAE) conjugates to two antibodies in percent Relative Light Units (RLUs), plotted as a function of time.

Light emission from antibody conjugates of the high light output acridinium esters HQYAE and NSP-2,7-DMG-DMAE to two different antibodies, anti-TSH Mab and anti-HBsAg-Mab (HBsAg=Hepatitis B, surface antigen), are compared in FIG. 5. In this case too, the zwitterion-containing compound displays significantly faster light emission with total light emission complete in <2 seconds whereas the conjugates derived from HQYAE take ~4 seconds for complete light emission. In addition, the relative chemiluminescence (Rel. CL) of the two acridinium esters was observed to be the same on the two different antibodies. Thus, zwitterion introduction at the phenol speeds up light emission but does not compromise the overall light output of acridinium ester.

Acridinium compounds are extremely useful chemiluminescent labels especially in automated immunochemistry instruments such as Centaur™ and ACS: 180™ (Siemens Healthcare Diagnostics) which use the acridinium esters NSP-DMAE-HEG and HQYAE. Both these instruments have high throughput which mean they are capable of running performing a large number immunoassay tests, 240 and 180 tests respectively, every hour respectively. The reagents derived from NSP-DMAE typically emit light over a period of five seconds when their chemiluminescence is triggered with the addition of 100 mM nitric acid containing 0.5% hydrogen peroxide followed by a second solution of 0.25 N sodium hydroxide plus surfactant. The zwitterion-containing acridinium compounds of the present invention, where the zwitterion is located on the phenol, by virtue of their fast light emission (≤2 seconds for ≥90% of total light emitted) can be used in automated immunochemistry instruments such as the ADVIA:Centaur™ to increase their throughput, when compared to the otherwise identical tests employing the acridinium esters NSP-DMAE-HEG and HQYAE.

Figure 6:
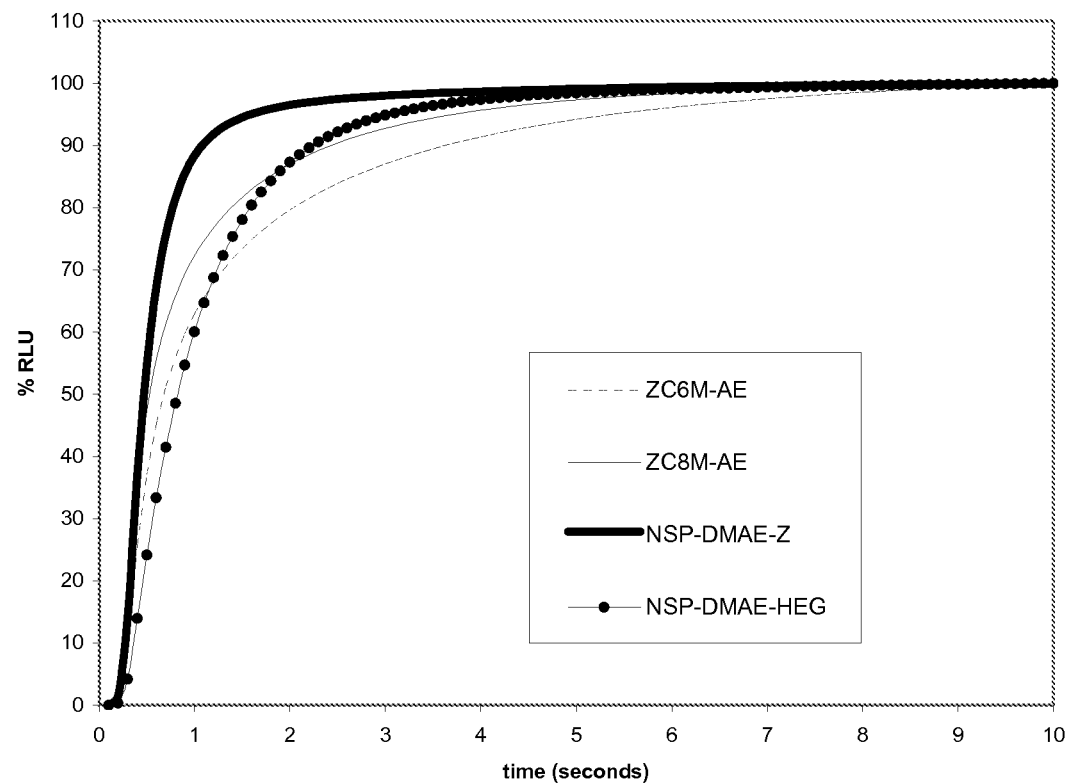
FIG. 6 is a plot of the light emitted from control (NSP-DMAE-Z) and exemplary zwitterion-containing acridinium (ZC6M-AE and ZC8M-AE) conjugates to anti-TSH Mab in percent Relative Light Units (RLUs), plotted as a function of time.

Finally in FIG. 6, the kinetics of light emission from the anti-TSH Mab conjugates of the zwitterion-containing acridinium esters ZC6M-AE, ZC8M-AE (the structures of which are shown in FIG. 1) and NSP-DMAE-Z-NHS are compared with that of NSP-DMAE-HEG. While the NSP-DMAE-Z conjugate, with the zwitterion modification at the phenol, exhibits faster light emission than NSP-DMAE-HEG as noted above, the two acridinium ester conjugates of ZC6M-AE and ZC8M-AE where the zwitterion is located in the acridinium ring, show emission kinetics comparable to NSP-DMAE-HEG. Thus, zwitterion introduction in the acridinium ring is also not detrimental to emission kinetics as observed in these two cases. Total light output from the anti-TSH Mab and anti-HBsAg Mab conjugates of the three zwitterion-containing compounds ZC6M-AE, ZC8M-AE and NSP-DMAE-Z was also observed to be similar and comparable to NSP-DMAE-HEG.

Enhanced stability of acridinium esters as originally described by Law et al. for DMAE, is another important characteristic of these compounds that facilitates their utility in commercial, automated, immunoanalyzers. By "stability," it is meant a minimal loss chemiluminescent activity as measured by the loss of RLUs when the compounds or conjugates are stored in an aqueous solution typically, in the pH range of 6-9, which is within the physiological pH. From a mechanistic viewpoint, hydrolysis of the phenolic ester is the main pathway by which chemiluminescent acridinium esters become non-chemiluminescent. Stable conjugates ensure long shelf life for acridinium ester reagents and also ensure that assay performance does not vary greatly over a given period of time. The stability of various acridinium ester conjugates (further described below) of the anti-TSH antibody of the current invention are listed in Table 2. Aqueous solutions of the conjugates were stored at either 4° C., that are typical for commercial automated instruments such as the Centaur™ or, at 37° C. in an aqueous buffer at pH 7.7. The harsher storage conditions at 37° C. where acridinium ester hydrolysis is expected to be accelerated, permitted a fair comparison of the relative stabilities of the various acridinium esters. Light as RLUs were recorded periodically using a luminometer for all the conjugates. The RLUs that were measured at the initial time point, also referred to as day 1, were assigned a value of 100%. The residual RLUs from each conjugate after four weeks are listed in Table 2. Other details pertaining to these measurements can be found in the Example 19.

TABLE 2

| | Acridinium Compounds | Chemiluminescence Stability (% RLU) for at Four (4) Weeks | |
|---|---|---|---|
| | | 4° C. | 37° C. |
| Controls | NSP-DMAE-HEG | 98 | 75 |
| | HQYAE | 92 | 58 |
| 1d | ZC3-AE | 106 | 64 |
| 5d | ZC3M-AE | 99 | 67 |
| 2d | ZC6-AE | 93 | 52 |
| 6d | ZC6M-AE | 99 | 68 |
| 7d | ZC8M-AE | 98 | 66 |
| 11f | NSP-DMAE-Z | 88 | 73 |
| 10f | NSP-2Z-DMAE | 118 | 94 |
| 8d | AZC3-AE | 100 | 60 |
| 9d | AZC6-AE | 100 | 56 |

From Table 2, the chemiluminescent stabilities of various zwitterion-containing acridinium ester conjugates of the current invention are comparable to those of NSP-DMAE-HEG and HQYAE. At 37° C., after 4 weeks, the conjugates of these two acridinium esters retain 75% and 58% of their chemiluminescent activity respectively. All conjugates of other zwitterion-containing acridinium esters show comparable stability ranging from 52% for the conjugate of ZC6-AE to 94% for the conjugate of NSP-2Z-DMAE. At 4° C., after 4 weeks, all acridinium ester conjugates showed minimal loss of chemiluminescent activity.

The zwitterion-containing acridinium compounds of the current invention are useful as labels in assays for the determination or quantitation of analytes. Analytes that are typically measured in such assays are often substances of some clinical relevance and can span a wide range of molecules from large macromolecules such as proteins, nucleic acids, viruses bacteria, etc. to small molecules such as ethanol, vitamins, steroids, hormones, therapeutic drugs, etc. A 'sandwich' immunoassay typically involves the detection of a large molecule, also referred to as macromolecular analyte, using two binding molecules such as antibodies. One antibody is immobilized or attached to a solid phase such as a particle, bead, membrane, microtiter plate or any other solid surface. Methods for the attachment of binding molecules such as antibodies to solid phases are well known in the art. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and microtiter plate. The second antibody is often covalently attached with a chemiluminescent or fluorescent molecule often referred to as a label. Labeling of binding molecules such as antibodies and other binding proteins are also well known in the art and are commonly called conjugation reactions and the labeled antibody is often called a conjugate. Typically, an amine-reactive moiety on the label reacts with an amine on the antibody to form an amide linkage. Other linkages such as thioether, ester, carbamate, and the like, between the antibody and the label are also well known. In the assay, the two antibodies bind to different regions of the macromolecular analyte. The macromolecular analyte can be, for example, proteins, nucleic acids, oligosaccharides, antibodies, antibody fragments, cells, viruses, receptors, or synthetic polymers. The binding molecules can be antibodies, antibody fragments, nucleic acids, peptides, binding proteins or synthetic binding polymers. For example the folate binding protein ("FBP") binds the analyte folate. Synthetic binding molecules that can bind a variety of analytes have also been disclosed by Mossbach et al. *Biotechnology* vol. 14, pp. 163-170 (1995).

When the solid phase with the immobilized antibody and the labeled antibody is mixed with a sample containing the analyte, a binding complex is formed between the analyte and the two antibodies. This type of assay is often called a heterogenous assay because of the involvement of a solid phase. The chemiluminescent or fluorescent signal associated with the binding complex can then be measured and the presence or absence of the analyte can be inferred. Usually, the binding complex is separated from the rest of the binding reaction components such as excess, labeled antibody prior to signal generation. For example if the binding complex is associated with a magnetic bead, a magnet can be used to separate the binding complex associated with the bead from bulk solution. By using a series of 'standards, that is, known concentrations of the analyte, a 'dose-response' curve can be generated using the two antibodies. Thus, the dose-response curve correlates a certain amount of measured signal with a specific concentration of analyte. In a sandwich assay, as the concentration of the analyte increases, the amount of signal also increases. The concentration of the analyte in an unknown sample can then be calculated by comparing the signal generated by an unknown sample containing the macromolecular analyte, with the dose-response curve.

In a similar vein, the two binding components can also be nucleic acids that bind or hybridize to different regions of a nucleic acid analyte. The concentration of the nucleic acid analyte can then be deduced in a similar manner.

Another class of immunoassays for small molecule analytes such as steroids, vitamins, hormones, therapeutic drugs or small peptides employs an assay format that is commonly referred to as a competitive assay. Typically, in a competitive assay, a conjugate is made of the analyte of interest and a chemiluminescent or fluorescent label by covalently linking the two molecules. The small molecule analyte can be used as such or its structure can be altered prior to conjugation to the label. The analyte with the altered structure is called an analog. It is often necessary to use a structural analog of the analyte to permit the chemistry for linking the label with the analyte. Sometimes a structural analog of an analyte is used to attenuate or enhance its binding to a binding molecule such an antibody. Such techniques are well known in the art. The antibody or a binding protein to the analyte of interest is often immobilized on a solid phase either directly or through a secondary binding interaction such as the biotin-avidin system.

The concentration of the analyte in a sample can be deduced in a competitive assay by allowing the analyte-containing sample and the analyte-label conjugate to compete for a limited amount of solid phase-immobilized binding molecule. As the concentration of analyte in a sample increases, the amount of analyte-label conjugate captured by the binding molecule on the solid phase decreases. By employing a series of 'standards', that is, known concentrations of the analyte, a dose-response curve can be constructed where the signal from the analyte-label conjugate captured by the binding molecule on the solid phase is inversely correlated with the concentration of analyte. Once a dose-response curve has been devised in this manner, the concentration of the same analyte in an unknown sample can be deduced by comparing the signal obtained from the unknown sample with the signal in the dose-response curve.

Another format of the competitive assay for small molecules analytes involves the use of a solid phase that is immobilized with the analyte of interest or an analyte analog and an antibody or a binding protein specific for the analyte that is conjugated with a chemiluminescent or fluorescent label. In this format, the antibody-label conjugate is captured onto the solid phase through the binding interaction with the analyte or the analyte analog on the solid phase. The analyte of interest present in a sample then "competitively" binds to the antibody-label conjugate and thus inhibits or replaces the interaction of the antibody-label conjugate with the solid phase. In this fashion, the amount of signal generated from the antibody-label conjugate captured on the solid phase is correlated to the amount of the analyte in sample.

Reagents for use in connection with these methods are also provided by the invention and typically comprise a chemiluminescent acridinium compound bound to an analyte, analyte analog, or binding partner for an analyte, the acridinium compound comprising (i) a hydrocarbon group attached to the nitrogen atom of the acridinium nucleus, said hydrocarbon group being optionally substituted with up to 20 heteroatoms, and (ii) a carboxyl or sulfonamide group at the $C_9$ position of the acridinium nucleus linked to a substituted hydrocarbon moiety being optionally substituted with up to 20 heteroatoms, wherein said acridinium compound comprises at least one zwitterionic functional group attached to the $C_2$ position of the acridinium nucleus, the $C_7$ position of the acridinium nucleus, the hydrocarbon moiety linked to the carboxyl or sulfonamide group, or the hydrocarbon group attached to the nitrogen atom of the acridinium nucleus; wherein said acridinium compound exhibits reduced non-specific binding to a solid phase as compared to an otherwise identical acridinium compound not comprising said zwitterionic functional group.

In accordance with the foregoing, an assay for the detection or quantification of a macromolecular analyte comprises, according to one embodiment of the invention, the following steps:

(a) providing a conjugate comprising: (i) a binding molecule specific for an analyte; and (ii) any of the inventive, zwitterion-containing acridinium ester or sulfonamide compounds;

(b) providing a solid support having immobilized thereon a second binding molecule specific for said analyte;

(c) mixing the conjugate, the solid phase and a sample suspected of containing the analyte to form a binding complex;

(d) separating the binding complex captured on the solid support;

(e) triggering chemiluminescence of the binding complex from step (d) by adding chemiluminescence triggering reagents;

(f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In another embodiment, an assay for the detection or quantification of a small molecule analyte is provided comprising the steps of:

(a) providing a conjugate of an analyte with any of the any of the inventive, zwitterion-containing acridinium ester or sulfonamide compounds;

(b) providing a solid support immobilized with a binding molecule specific for the analyte;

(c) mixing the conjugate, solid support and a sample suspected of containing the analyte to form a binding complex;

(d) separating the binding complex captured on the solid support;

(e) triggering the chemiluminescence of the binding complex from step (d) by adding chemiluminescence triggering reagents;

(f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

In an alternate assay format, the zwitterion-containing acridinium compounds of the present invention are also useful for the detection of small molecule analytes in assays comprising the following steps;

a) providing a solid support immobilized with an analyte or an analyte analog;

b) providing a conjugate of a binding molecule specific for the analyte with a zwitterion-containing, acridinium ester or sulfonamide compounds of the current invention;

c) mixing the solid phase, the conjugate and a sample suspected containing the analyte to form a binding complex;

d) separating the binding complex captured on the solid support;

e) triggering the chemiluminescence of the binding complex of (d) by adding chemiluminescence triggering reagents;

f) measuring the amount of light with an luminometer; and g) detecting the presence or calculating the concentration of the analyte by comparing the amount of light emitted from the reaction mixture with a standard dose response curve which relates the amount of light emitted to a known concentration of the analyte.

The chemiluminescence triggering reagents can be either hydrogen peroxide or peroxide salts.

Macromolecular analytes can be proteins, nucleic acids, oligosaccharides, antibodies, antibody fragments, cells, viruses, synthetic polymers, and the like.

Small molecule analytes can be steroids, vitamins, hormones, therapeutic drugs, small peptides, and the like.

The binding molecules in the assays can be an antibody, an antibody fragment, a binding protein, a nucleic acid, a peptide, a receptor or a synthetic binding molecule.

Example 1

Synthesis of ZC3-AE-NHS, Compound 1d a) Compound 1a

A solution of 2,7-dihydroxy acridine methyl ester, (0.1 g, 0.24 mmol), (U.S. Pat. No. 7,309,615), 3-dimethylaminopropanol (0.112 mL, 4 equivalents) and triphenylphosphine (0.252 g, 4 equivalents) in anhydrous tetrahydrofuran (10 mL) was treated with diisopropyl azodicarboxylate (0.188 mL, 4 equivalents) under a nitrogen atmosphere. The reaction was stirred at room temperature for 16 hours. TLC analysis on silica using ethyl acetate as eluent showed no starting material and using 75% ethyl acetate, 24% methanol and 1% triethylamine, a polar product (Rf ~0.15) was observed. The solvent was then removed under reduced pressure and the residue was partitioned between 1N HCl (25 mL) and ethyl acetate (25 mL). The aqueous layer containing product was extracted two more times with ethyl acetate (2×25 mL). The acidic aqueous layer was then treated with 2.5% aqueous sodium hydroxide drop wise until a bright yellow suspension was formed. This suspension was extracted with ethyl acetate (3×25 mL). A small portion of this solution was then analyzed by HPLC using a Phenomenex, $C_{18}$ 4.6 mm×25 cm column and a 40 minute gradient of 10→60% B (A=water with 0.05% TFA, B=MeCN with 0.05% TFA) at a flow rate of 1.0 mL/minute and UV detection at 260 nm. Product was observed eluting at Rt=25 minutes and was the major component. The ethyl acetate solution was dried over anhydrous magnesium sulfate, filtered and concentrated under reduced pressure to yield a sticky yellow solid. Yield=126 mg (89%); MALDI-TOF MS 588.3 observed.

b) Compound 1c

A mixture of compound 1a (0.126 g, 0.215 mmol), distilled 1,3-propane sultone (0.785 g, 30 equivalents) and 2,6-di-tert-butylpyridine (0.470 mL, 10 equivalents) in the ionic liquid [BMIM][PF6] (1-2 mL) was heated at 150° C. under a nitrogen atmosphere for 24 hours. The reaction was then cooled to room temperature. A small portion (1-2 uL) of the reaction mixture was withdrawn, diluted with methanol (0.1 mL) and analyzed by analytical HPLC using the gradient described above in section (a). A major product was observed eluting at Rt=18 minutes which by MALDI-TOF MS analysis (953.5 observed) corresponded to the tri-alkylkated, acridinium ester product 1b. The crude reaction mixture was partitioned between ethyl acetate (30 mL) and water (30 mL). The aqueous layer containing product was extracted three more times with ethyl acetate (3×30 mL). The aqueous layer was concentrated under reduced pressure to afford crude acridinium ester 1b. This material was dissolved in 1N HCl (15 mL) and refluxed under nitrogen for 1.5 hours and then cooled to room temperature. HPLC analysis of the reaction mixture indicated clean hydrolysis of the methyl ester with the product 1c eluting at Rt=16 minutes. The reaction mixture was concentrated to ~10 mL and the product was purified by preparative HPLC using an YMC, $C_{18}$ 30×300 mm column and the same gradient at described in section (a) at a solvent flow rate of 20 mL/minute and UV detection at 260 nm. The HPLC fractions containing product were combined and concentrated under reduced pressure. Yield=116 mg (57% overall); MALDI-TOF MS 941.2 observed.

c) Compound 1d

A partial solution of acridinium carboxylic acid 1c (30 mg, 32 umoles) in DMF (3 mL) and water (0.3 mL) was treated with diisopropylethylamine (7 uL, 1.5 equivalents) and TSTU (19 mg, 2 equivalents). The reaction was stirred vigorously at room temperature. After 24 hours, HPLC analysis of the reaction mixture using the gradient described in section (a) showed product (~20% conversion) eluting at Rt=17.5 minutes. The reaction was then diluted with water (2.7 mL) which gave a clear solution and was then treated with additional diisopropylethylamine (10 uL, 2 equivalents) and TSTU (50 mg, 5 equivalents). The reaction was stirred at room temperature for 0.5 hour and then analyzed by HPLC which indicated ~40% conversion. The product was then purified by preparative HPLC using the gradient and column described in section (b). HPLC fractions containing product were frozen at −80° C. and lyophilized to dryness to afford a bright yellow powder. Yield=11 mg (33%); MALDI-TOF MS 1037.4 observed.

The following reactions describe the synthesis of ZC3-AE-NHS, compound 1d.

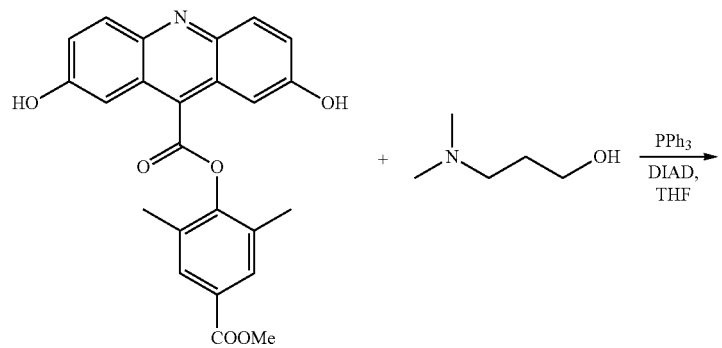

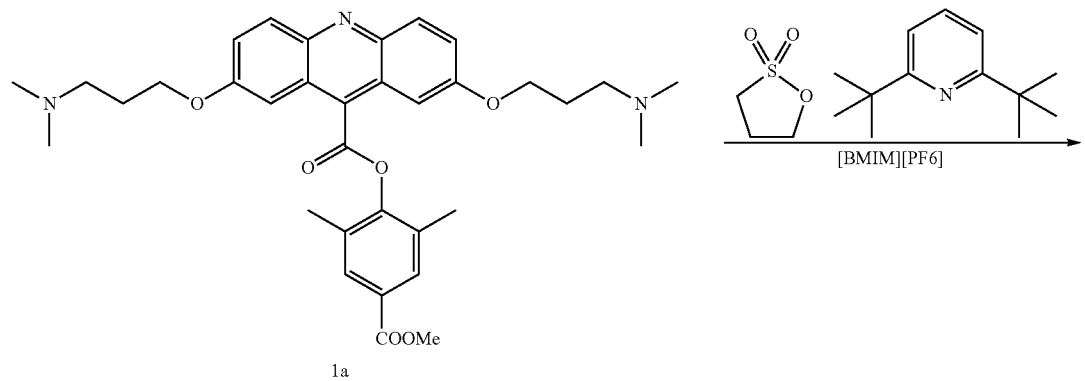

1a

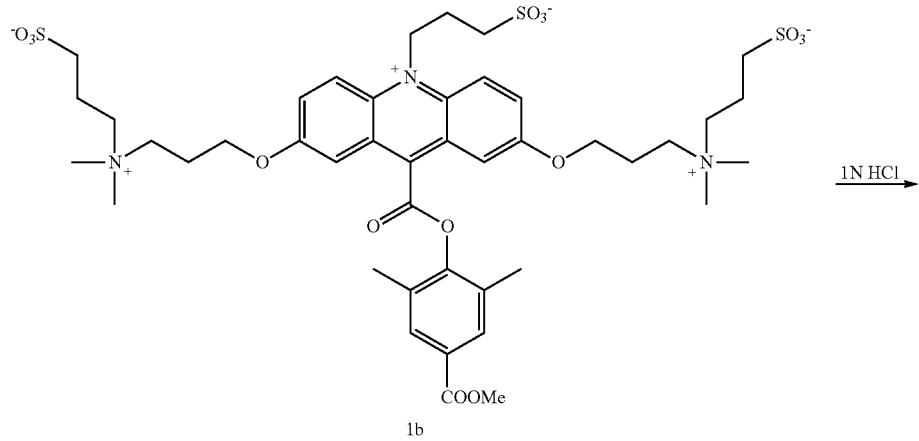

1b

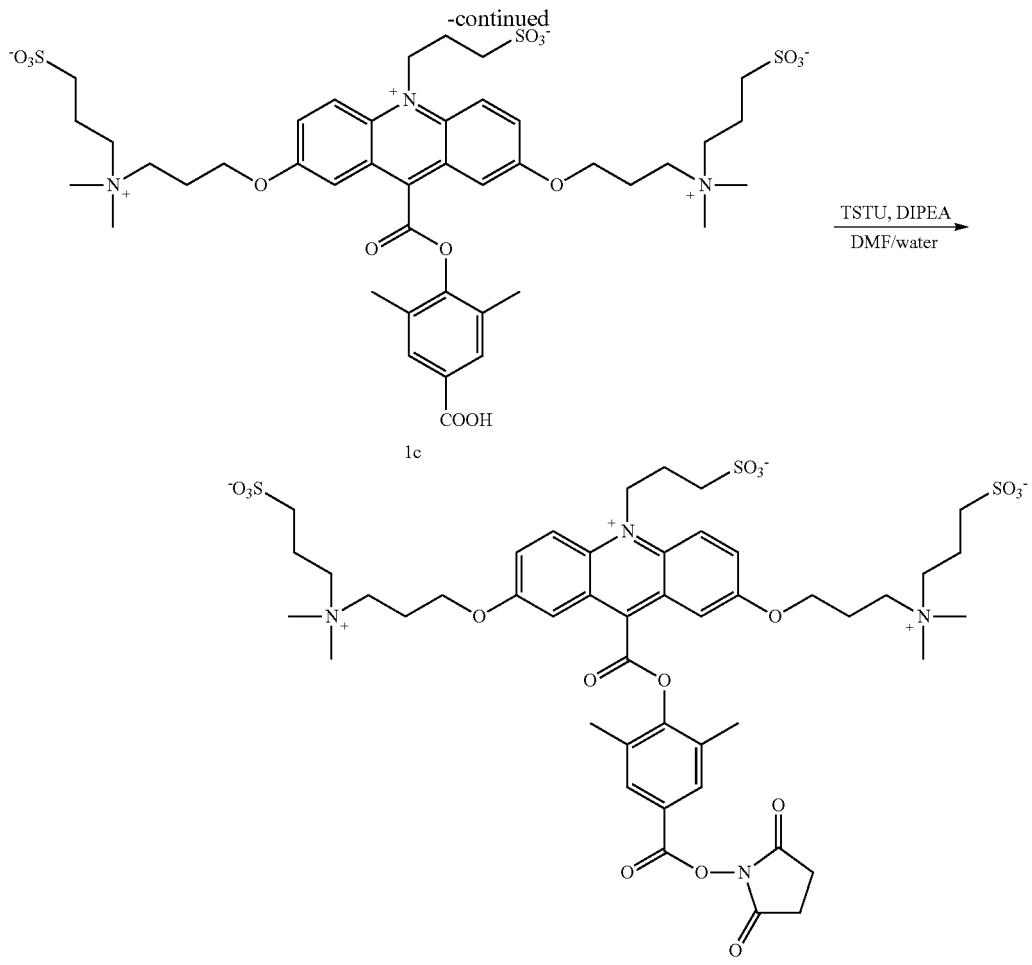

Example 2

Synthesis of ZC6-AE-NHS, Compound 2d a) Compound 2a

A solution of 2,7-dihydroxy acridine methyl ester, (30 mg, 72 umoles), 6-dimethylamino-1-hexanol (42 mg, 4 equivalents) and triphenylphosphine (75 mg, 4 equivalents) in anhydrous tetrahydrofuran (5 mL) was treated with diisopropyl azodicarboxylate (0.06 mL, 5 equivalents). The reaction was stirred at room temperature under a nitrogen atmosphere for 16 hours. TLC analysis on silica using 70% ethyl acetate, 28% methanol, 2% triethylamine showed clean conversion to a polar product. HPLC analysis of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=25 minutes and was the major component. The product was isolated as described in Example 1, section (a). Yield=36 mg (75%).

b) Compound 2c

A mixture of compound 2a (36 mg, 54 umoles), distilled 1,3-propane sultone (0.2 g, 30 equivalents) and 2,6-di-tert-butylpyridine (0.120 mL, 10 equivalents) in the ionic liquid [BMIM][PF6] (1 g) was heated at 150° C. under a nitrogen atmosphere for 24 hours. The reaction was then cooled to room temperature and partitioned between ethyl acetate (30 mL) and water (50 mL). The aqueous layer containing product was separated and washed twice with ethyl acetate (2×30 mL). HPLC analysis of the aqueous solution using the gradient described in section (a) indicated >80% conversion to the tri-alkylated product eluting at Rt=19 minutes with ~20% di-alkylated product eluting at Rt=24 minutes. The aqueous layer containing crude acridinium ester product 2b was concentrated under reduced pressure. The residue was dissolved in 1N HCl (10 mL) and refluxed under a nitrogen atmosphere for 2 hours. The reaction mixture was then cooled to room temperature and analyzed by HPLC which indicated clean conversion to the acridinium carboxylic acid eluting at Rt=17 minutes. The product was purified by preparative HPLC using an YMC, $C_{18}$ 30×300 mm column and the same gradient at described in section (a) at a solvent flow rate of 20 mL/minute and UV detection at 260 nm. The HPLC fractions containing product were combined and concentrated under reduced pressure to give compound 2c. Yield=39.4 mg (71% overall); MALDI-TOF MS 1025.1 observed.

c) Compound 2d

A solution of compound 2c (39 mg, 38 umoles) in 15% water/DMF (4 mL) was treated with diisopropylethylamine (0.033 mL, 5 equivalents) and TSTU (57 mg, 5 equivalents). The reaction was stirred at room temperature for 15 minutes and analyzed by HPLC as described in section (a). Complete conversion to the NHS ester product 2d was observed eluting at Rt=18.4 minutes. The product was purified by preparative HPLC using an YMC, $C_{18}$ 30×300 mm column and the same gradient at described in section (a) at a solvent flow rate of 20 mL/minute and UV detection at 260 nm. The HPLC fractions containing product were combined, frozen at −80° C. and lyophilized to dryness to give compound 2d. Yield=28 mg (66%); MALDI-TOF MS 1120.8 observed.
The following reactions describe the synthesis of ZC6-AE-NHS, compound 2d.
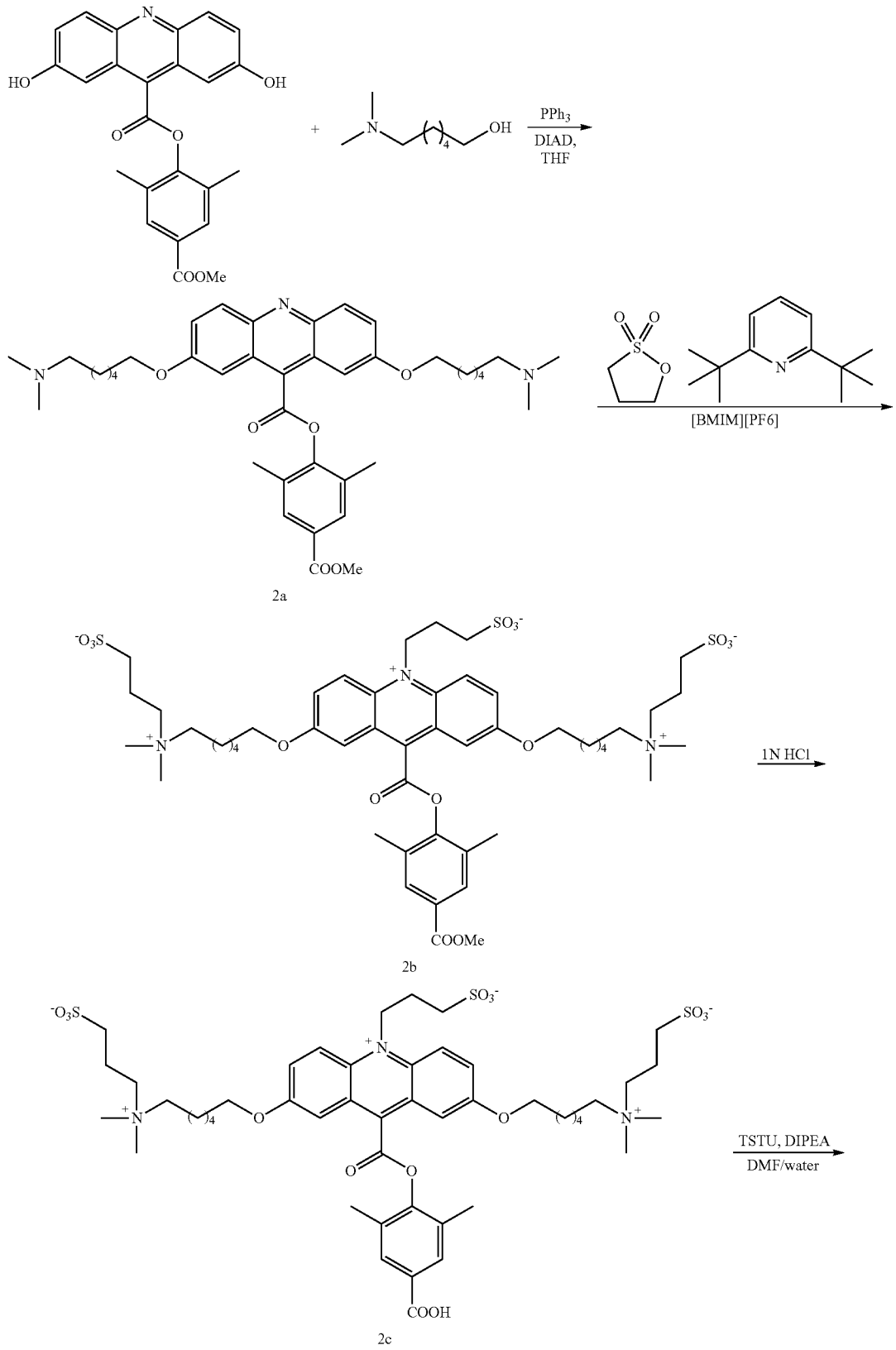

-continued

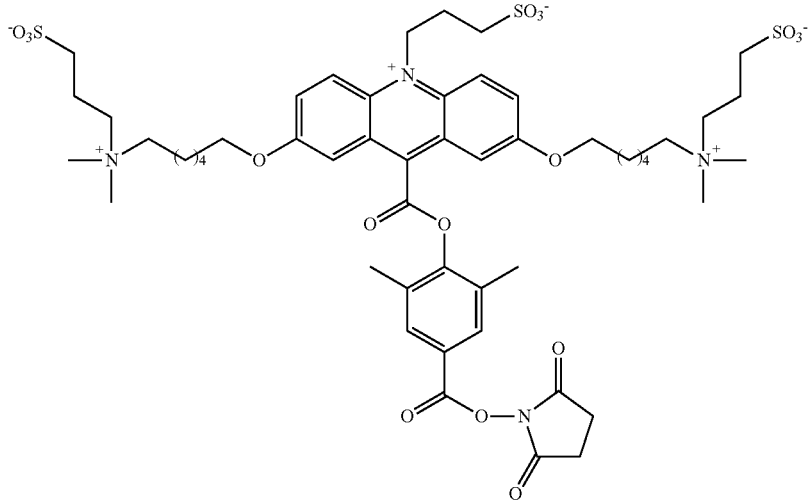

2d

Example 3

Synthesis of ZC8-AE-NHS, Compound 3d a) Compound 3a

A solution of 2,7-dihydroxy acridine methyl ester, (30 mg, 72 umoles), 8-dimethylamino-1-octanol (50 mg, 4 equivalents) and triphenylphosphine (75 mg, 4 equivalents) in anhydrous tetrahydrofuran (5 mL) was treated with disopropyl azodicarboxylate (0.06 mL, 5 equivalents). The reaction was stirred under a nitrogen atmosphere for 16 hours. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=22.5 minutes and was the major component. The product 3a was isolated as described in Example 1, section (a). Yield=58 mg (quantitative), MALDI-TOF MS 728.6 observed.

b) Compound 3c

A mixture of compound 3a (58 mg, 80 umoles), distilled 1,3-propane sultone (0.291 g, 30 equivalents) and 2,6-di-tert-butylpyridine (0.175 mL, 10 equivalents) in the ionic liquid [BMIM][PF6] (1 g) was heated at 150° C. under a nitrogen atmosphere for 24 hours. The reaction was then cooled to room temperature and partitioned between ethyl acetate (30 mL) and water (30 mL). The aqueous layer containing product was separated and washed twice with ethyl acetate (2×30 mL). HPLC analysis of the aqueous solution using the gradient described in section (a) indicated the acridinium ester product 3b eluting at Rt=1.5 min (MALDI-TOF MS 1094 observed). The aqueous layer was concentrated under reduced pressure and the recovered brown oil was refluxed in 1N HCl (10 mL) under nitrogen. After 2 hours, the reaction was cooled to room temperature and analyzed by HPLC which indicated product eluting at Rt=16 minutes. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 3c. Yield=30 mg (39% overall); MALDI-TOF MS 1082.4 observed.

c) Compound 3d

A solution of compound 3c (23 mg, 21.3 umoles) in 15% water/DMF (2 mL) was treated with diisopropylethylamine (18.6 uL, 5 equivalents) and TSTU (32 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 40 minute gradient of 10→60% B (A=water with 0.05% TFA, B=MeCN with 0.05% TFA) at a flow rate of 1.0 mL/minute and UV detection at 260 nm. Product was observed eluting at Rt=29 minutes and was the major component. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product were combined, frozen at −80° C. and lyophilized to dryness to give product 3d. Yield=15 mg (60%); MALDI-TOF MS 1178.8 observed.

The following reactions describe the synthesis of ZC8-AE-NHS, compound 3d.

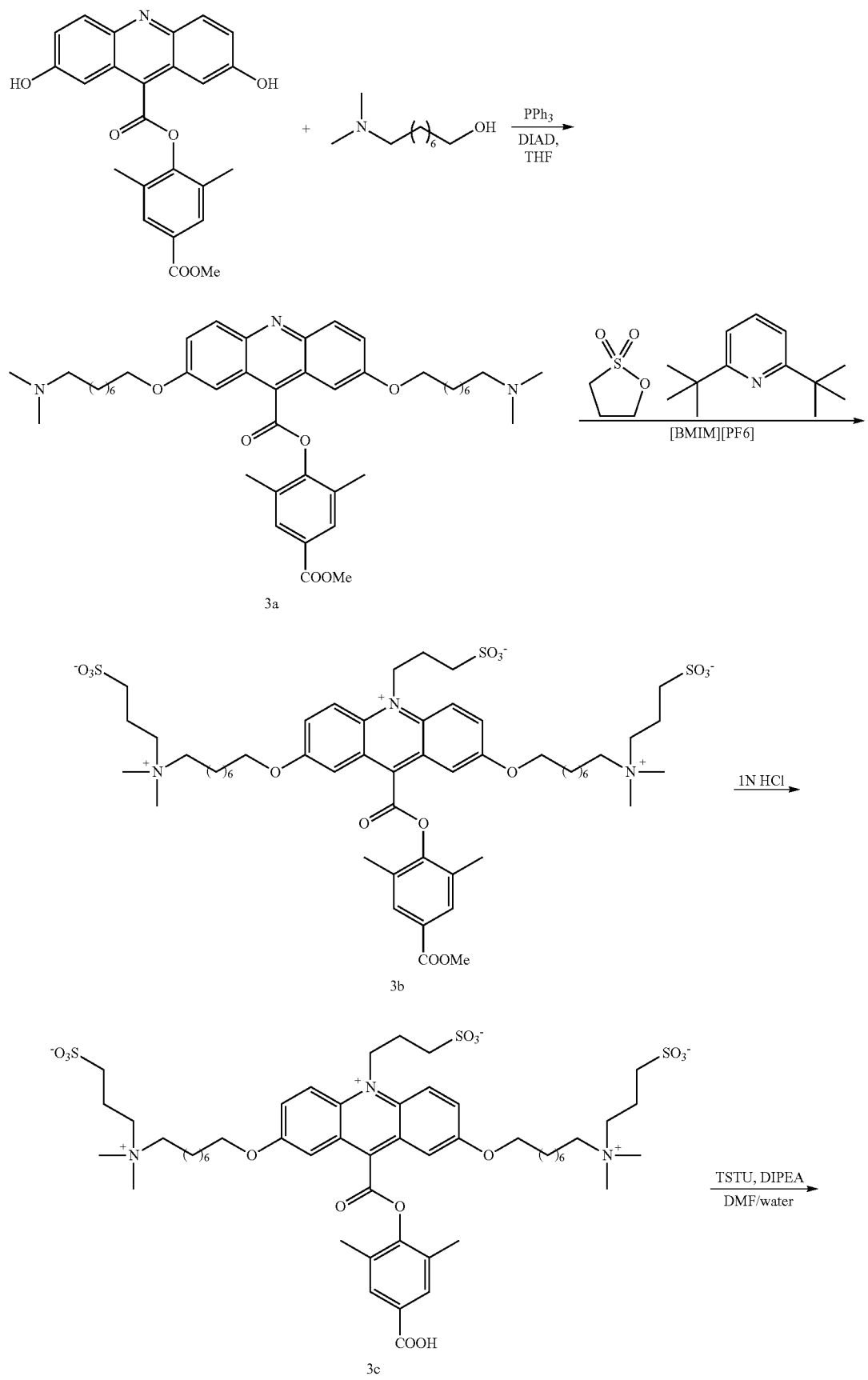

-continued

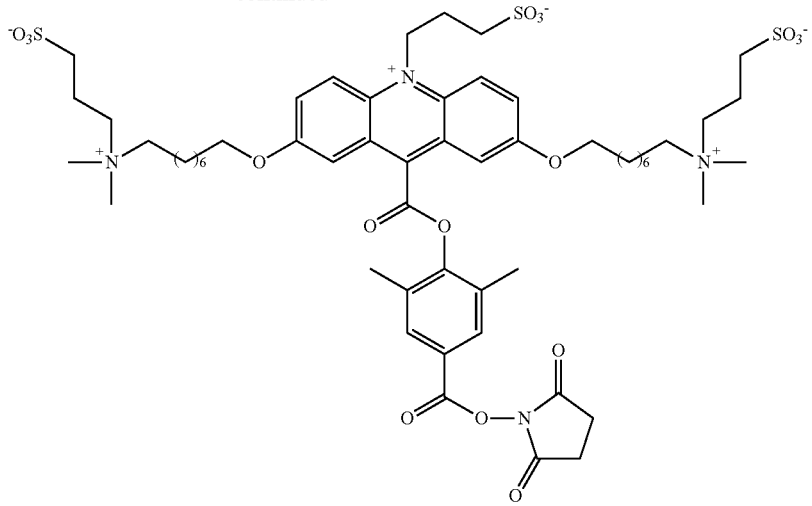

3d

Example 4

Synthesis of ZC12-AE-NHS, Compound 4e a) 12-dimethylamino-1-dodecanol, 4a

A solution of 12-bromo-1-dodecanol (1 g, 3.8 mmoles) in anhydrous tetrahydrofuran (10 mL) was treated with a 2.0 M solution of dimethylamine in tetrahydrofuran (10 mL). The reaction was stirred at room temperature for 3 days. TLC analysis on silica using 25% ethyl acetate, 75% hexanes as eluent showed the formation of a polar product with little starting material. The reaction was diluted with ethyl acetate (75 mL) and washed twice with aqueous sodium bicarbonate and water. The ethyl acetate solution was then dried over anhydrous magnesium sulfate, filtered and concentrated under reduced pressure. Yield=1.2 g (wax). TLC analysis on silica (25% methanol, 75% ethyl acetate) showed a streaking product with Rf ~0.1. This product 4a, was used without purification.

b) Compound 4b

A solution of 2,7-dihydroxy acridine methyl ester, (30 mg, 72 umoles), 12-dimethylamino-1-dodecanol (66 mg, 4 equivalents) and triphenylphosphine (75 mg, 4 equivalents) in anhydrous tetrahydrofuran (5 mL) was treated with diisopropyl azodicarboxylate (0.06 mL, 5 equivalents). After 2 hours, the reaction was treated with additional 4 equivalents of triphenylphosphine and 5 equivalents of diisopropyl azodicarboxylate. After 30 minutes, a small portion was analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=30 minutes and was the major component. The product 4b was isolated as described in Example 1, section (a). Yield=57 mg (95%), MALDI-TOF MS 840.3 observed.

c) Compound 4d

A mixture of compound 4b (57 mg, 68 umoles), 1,3-propane sultone (0.250 g, 30 equivalents) and 2,6-di-tert-butylpyridine (0.15 mL, 10 equivalents) in the ionic liquid [BMIM][PF6] (1 mL) was heated at 150° C. under nitrogen for 24 hours. The reaction was then cooled to room temperature and processed as described in Example 2, section (b). HPLC analysis of the crude reaction mixture using the gradient described in section (a) indicated the acridinium ester product 4c eluting at Rt=24 minutes (MALDI-TOF MS 1206.2 observed). The crude product 4c was refluxed in 1N HCl (10 mL) for 4 hours. The reaction was then cooled to room temperature and analyzed by HPLC which indicated ~70% conversion to the product 4d eluting at Rt=21 minutes. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 4d. Yield=22 mg (27% overall); MALDI-TOF MS 1193.4 observed.

d) Compound 4e

A solution of compound 4d (22 mg, 18.4 umoles) in DMF (3.4 mL) and water (0.6 mL) was treated with diisopropylethylamine (16 uL, 5 equivalents) and TSTU (28 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=22 minutes and was the major component. The product was purified by preparative HPLC using an YMC, $C_{18}$ 30×300 mm column and 30 minute gradient of 10→1000% B (A=water with 0.05% TFA, B=MeCN with 0.05% TFA) at a solvent flow rate of 20 mL/minute and UV detection at 260 nm. The HPLC fractions containing product were combined, frozen at −80° C. and lyophilized to dryness to give product 4e. Yield=15.4 mg (64%); MALDI-TOF MS 1290.6 observed.

The following reactions describe the synthesis of ZC12-AE-NHS, compound 4e.

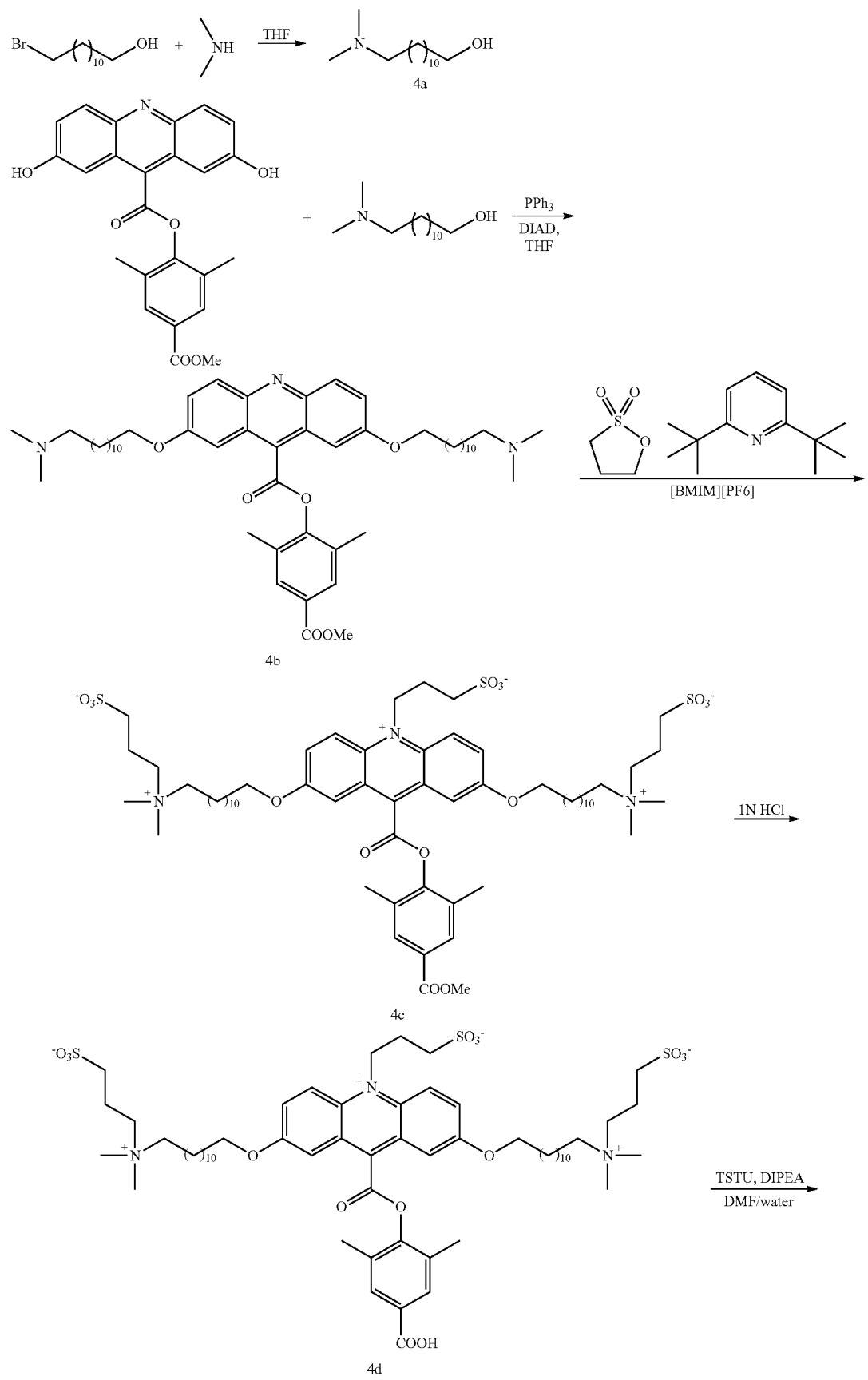

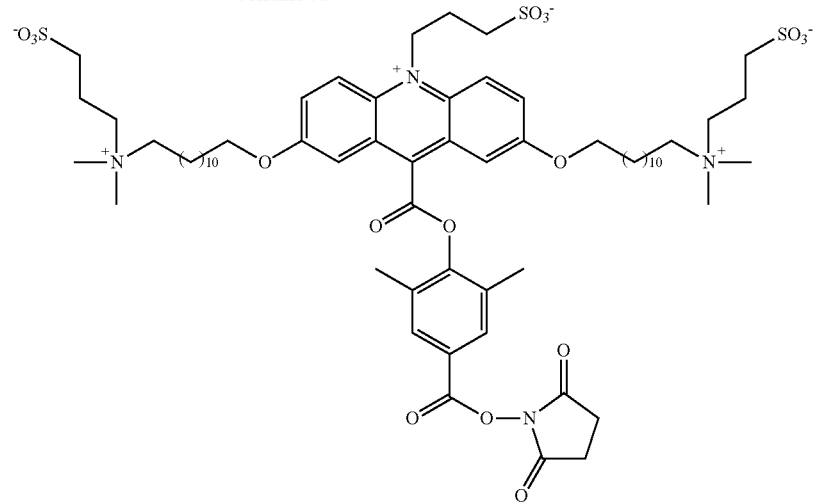

4e

Example 5

Synthesis of ZC3M-AE-NHS, Compound 5d a) Compound 5a

A solution of 2-hydroxy acridine methyl ester (25 mg, 62.3 umoles) (synthesized in a similar manner as the dihydroxy derivative in U.S. Pat. No. 7,309,615), 3-dimethylamino-1-propanol (15 uL, 2 equivalents) and triphenylphosphine (33 mg, 2 equivalents) in anhydrous tetrahydrofuran (3 mL) was treated with diisopropyl azodicarboxylate (25 uL, 2 equivalents). The reaction was stirred at room temperature under nitrogen. After 1 hour, TLC analysis on silica using 1:1, ethyl acetate/methanol was eluent showed the clean formation of a polar product of Rf~0.2. HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=25.2 minutes and was the major component. The reaction was diluted with ethyl acetate (25 mL) and 1N HCl (25 mL). The HCl layer with product was separated and washed twice with ethyl acetate (2×25 mL). The HCl layer was then cooled in ice and treated with 5% aqueous KOH until a suspension was formed. This suspension was extracted with ethyl acetate (2×25 mL). The combined ethyl acetate extracts was washed with water (25 mL). It was then dried over anhydrous magnesium sulfate, filtered and concentrated under reduced pressure to afford compound 5a. Yield 24.5 mg (82%); MALDI-TOF MS 487.5 observed.

b) Compound 5c

A mixture of compound 5a (24.5 mg, 51.3 umoles), 1,3-propane sultone (125 mg, 20 equivalents) and 2,6-di-tert-butylpyridine (79 uL, 7 equivalents) in the ionic liquid [BMIM][PF6] (0.5 mL) was heated at 150° C. for 24 hours. The reaction was then cooled to room temperature and a small portion (1-2 uL) was withdrawn, diluted with methanol and analyzed by HPLC as described in section (a). Acridinium ester product 5b was observed eluting at Rt=18 minutes (>80% conversion; MALDI-TOF MS 731.04 observed). The reaction was partitioned between ethyl acetate (25 mL) and water (25 mL). The aqueous layer containing product was separated and washed once with ethyl acetate (50 mL). It was then concentrated under reduced pressure. The residue was refluxed in 10 mL of 1N HCl for 2 hours under nitrogen and cooled to room temperature. HPLC analysis of the reaction mixture indicated clean formation of the product 5c eluting at Rt=15 minutes. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 5c. Yield=32 mg (89% overall); MALDI-TOF MS 717.1 observed.

c) Compound 5d

A solution of compound 5c (32 mg, 44.6 umoles) in DMF (3.4 mL) and water (0.6 mL) was treated with diisopropylethylamine (39 uL, 5 equivalents) and TSTU (67 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=17 minutes and was the major component. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product 5d were combined, frozen at −80° C. and lyophilized to dryness. Yield=25 mg (69%); MALDI-TOF MS 814.1 observed.

The following reactions describe the synthesis of ZC3M-AE-NHS, compound 5d.

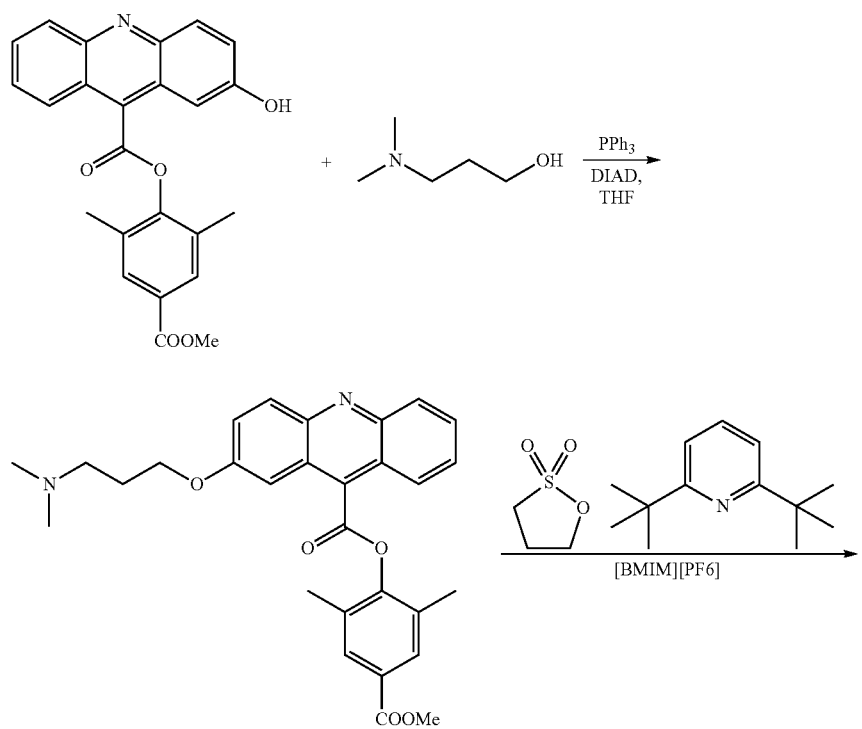
5a
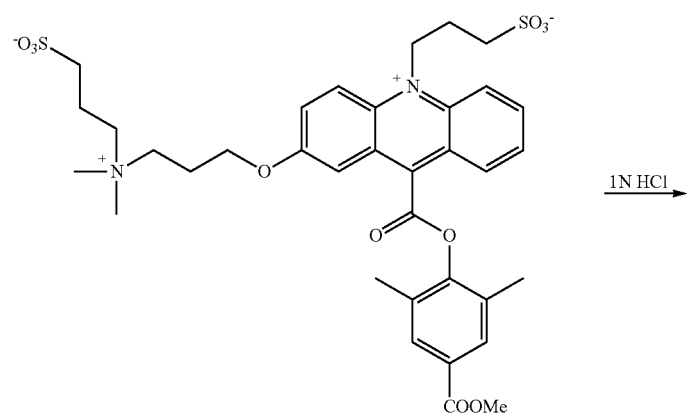
5b
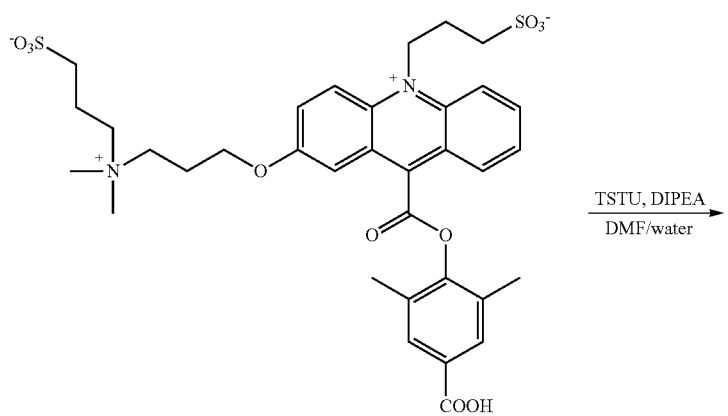
5c

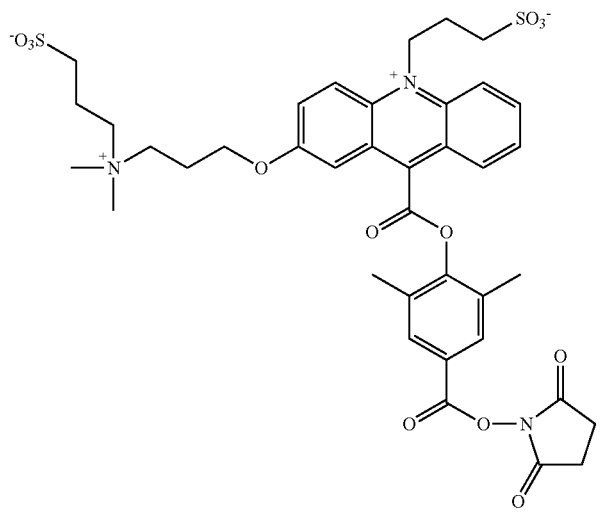

5d

Example 6

Synthesis of ZC6M-AE-NHS, Compound 6d a) Compound 6a

A solution of 2-hydroxy acridine methyl ester (25 mg, 62.3 umoles), 6-dimethylamino-1-hexanol (18 mg, 2 equivalents) and triphenylphosphine (33 mg, 2 equivalents) in anhydrous tetrahydrofuran (3 mL) was treated with diisopropyl azodicarboxylate (25 uL, 2 equivalents). The reaction was stirred at room temperature under nitrogen for 1 hour and then worked up as described in section (a), Example 5. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=22 minutes and was the major component. Yield 33.5 mg (quantitative); MALDI-TOF MS 529.5 observed.

b) Compound 6c

A mixture of compound 6a (33.5 mg, 63.3 umoles), 1,3-propane sultone (155 mg, 20 equivalents) and 2,6-di-tert-butylpyridine (97 uL, 7 equivalents) in the ionic liquid [BMIM][PF6] (0.5 mL) was heated at 150° C. for 24 hours. The reaction was then cooled to room temperature and a small portion (1-2 uL) was withdrawn, diluted with methanol and analyzed by HPLC as described in section (a). Acridinium ester product 6b was observed eluting at Rt=16 minutes (>80% conversion; MALDI-TOF MS 773.5 observed). The reaction mixture was worked up as described in section (b), Example 5. The acridinium ester 6b was refluxed in 10 mL of 1N HCl for 2 hours under nitrogen and cooled to room temperature. HPLC analysis of the reaction mixture indicated clean formation of the product 6c eluting at Rt=14 minutes. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 6c. Yield=26.8 mg (56% overall).

c) Compound 6d

A solution of compound 6c (26.9 mg, 35.3 umoles) in DMF (3.4 mL) and water (0.6 mL) was treated with diisopropylethylamine (31 uL, 5 equivalents) and TSTU (53 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=15.4 minutes and was the major component. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product 6d were combined, frozen at −80° C. and lyophilized to dryness. Yield=19.3 mg (63%); MALDI-TOF MS 856.2 observed.

The following reactions describe the synthesis of ZC6M-AE-NHS, compound 6d.

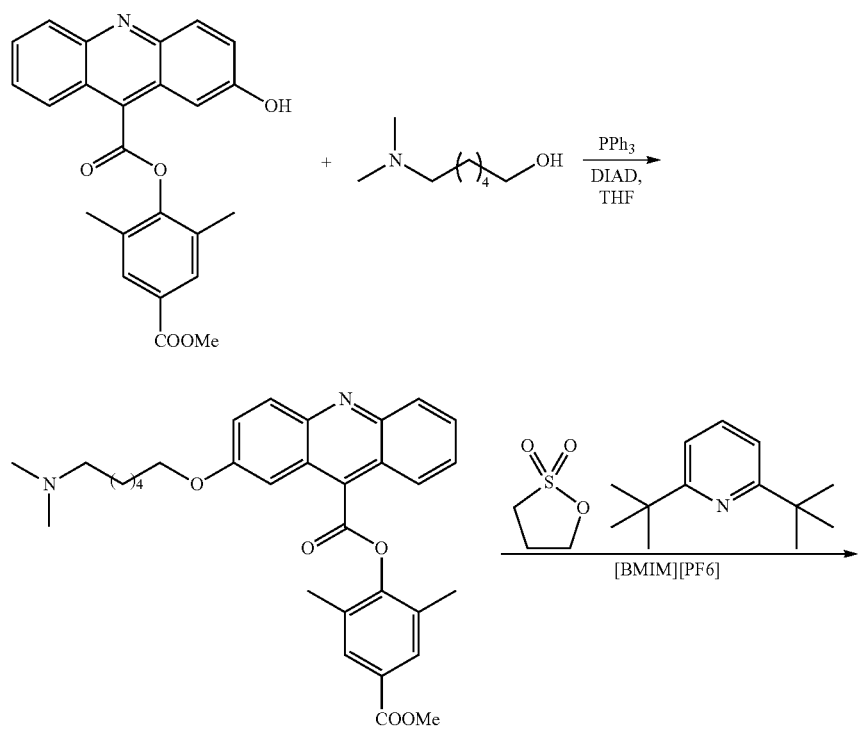
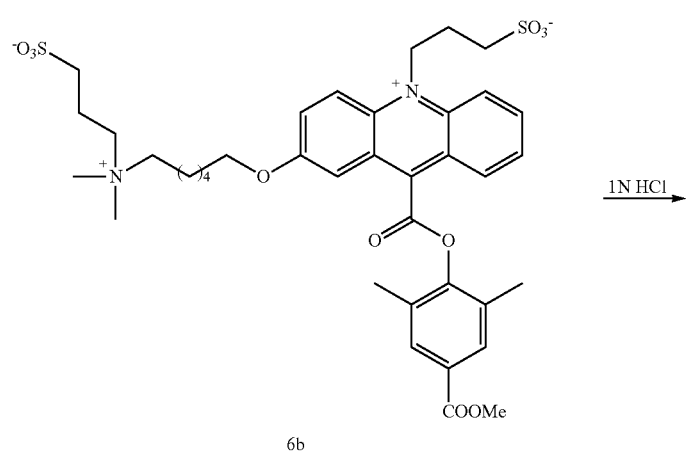
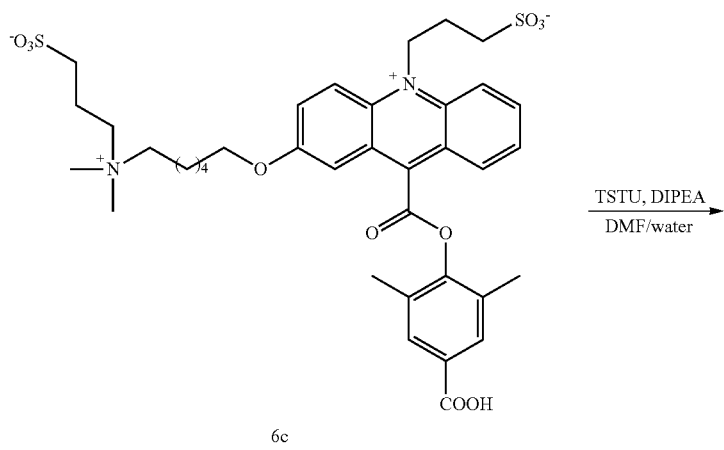

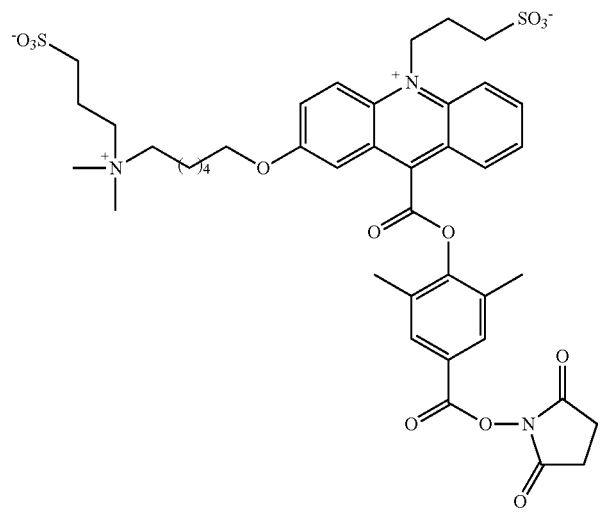

6d

Example 7

Synthesis of ZC8M-AE-NHS, Compound 7d a) Compound 7a

A solution of 2-hydroxy acridine methyl ester (30 mg, 75 umoles), 8-dimethylamino-1-octanol (26 mg, 2 equivalents) and triphenylphosphine (40 mg, 2 equivalents) in anhydrous tetrahydrofuran (5 mL) was treated with diisopropyl azodicarboxylate (30 uL, 2 equivalents). The reaction was stirred at room temperature under nitrogen for 1 hour and then worked up as described in section (a), Example 5. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=24 minutes and was the major component. Yield 13 mg (31%); MALDI-TOF MS 557.1 observed.

b) Compound 7c

A mixture of compound 7a (13 mg, 23.3 umoles), 1,3-propane sultone (57 mg, 20 equivalents) and 2,6-di-tert-butylpyridine (36 uL, 7 equivalents) in the ionic liquid [BMIM][PF6] (0.2 mL) was heated at 150° C. for 24 hours. The reaction was then cooled to room temperature and a small portion (1-2 uL) was withdrawn, diluted with methanol and analyzed by HPLC as described in section (a). Acridinium ester product 7b was observed eluting at Rt=17.4 minutes (>80% conversion; MALDI-TOF MS 800.8 observed). The reaction mixture was worked up as described in section (b), Example 5. The acridinium ester 7b was refluxed in 5 mL of 1N HCl for 2 hours under nitrogen and cooled to room temperature. HPLC analysis of the reaction mixture indicated clean formation of the product 7c eluting at Rt=15.3 minutes. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 7c. Yield=6.8 mg (37% overall); MALDI-TOF MS 787.8 observed.

c) Compound 7d

A solution of compound 7c (6.8 mg, 8.6 umoles) in DMF (1.7 mL) and water (0.3 mL) was treated with diisopropylethylamine (7.5 uL, 5 equivalents) and TSTU (13 mg, 5 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=16.5 minutes and was the major component. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product 7d were combined, frozen at −80° C. and lyophilized to dryness. Yield=5 mg (66%); MALDI-TOF MS 885.0 observed.

The following reactions describe the synthesis of ZC8M-AE-NHS, compound 7d.

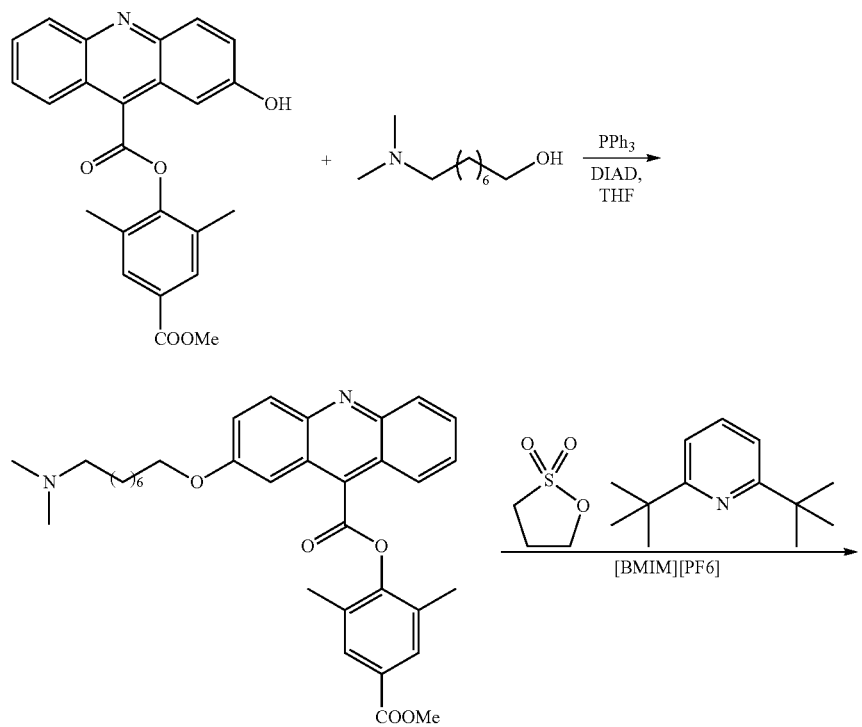
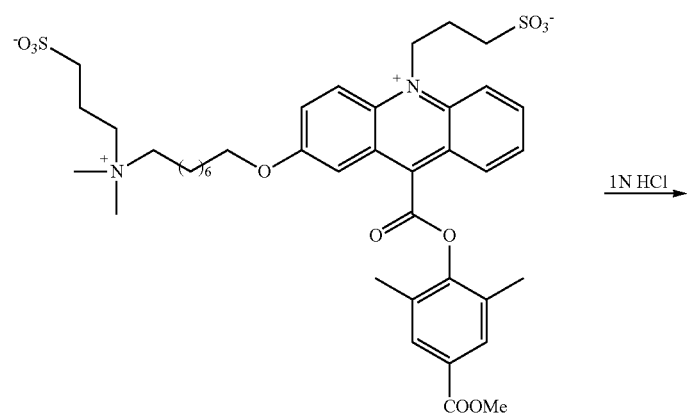
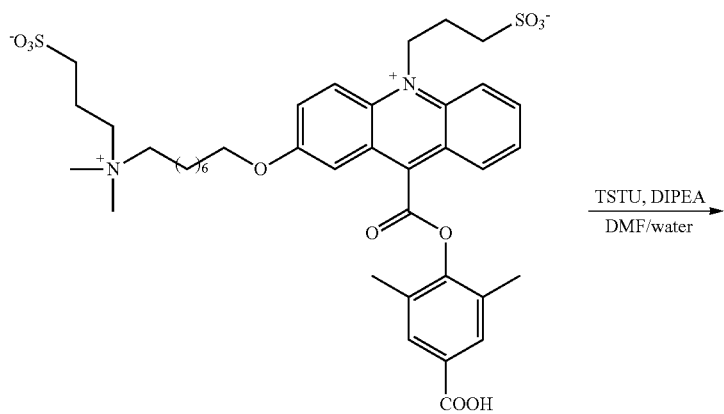

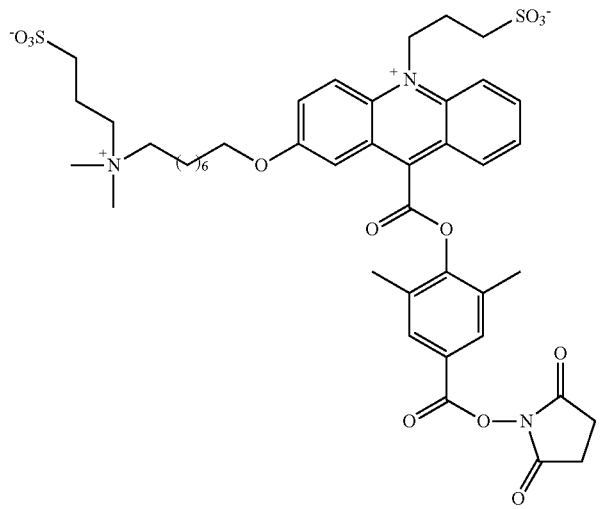

7d

Example 8

Synthesis of AZC3-AE-NHS, Compound 8d a) Compound 8a

The compound 2-hydroxy-7-methoxyacridine methyl ester was synthesized from 2-benzyloxy-7-methoxy acridine-9-carboxylic acid and methyl 2,6-dimethyl-4-hydroxybenzoate using the reactions described in U.S. Pat. No. 7,319,041 B2. A solution of 2-hydroxy-7-methoxyacridine methyl ester (25 mg, 0.058 mmol), 3-dimethylamino-1-propanol (13.6 uL, 2 equivalents) and triphenylphosphine (30 mg, 2 equivalents) in anhydrous tetrahydrofuran (5 mL) was treated with diisopropyl azodicarboxylate (23 uL, 2 equivalents). The reaction was stirred at room temperature under nitrogen. After 1 hour, it was worked up as described in section (a), Example 5. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=20 minutes and was the major component. Yield 27 mg (90%); MALDI-TOF MS 517.9 observed.

b) Compound 8c

A mixture of compound 8a (27 mg, 52.2 umoles), 1,3-propane sultone (128 mg, 20 equivalents) and 2,6-di-tert-butylpyridine (80 uL, 7 equivalents) in the ionic liquid [BMIM][PF6] (0.5 mL) was heated at 150° C. for 24 hours. The reaction was then cooled to room temperature and a small portion (1-2 uL) was withdrawn, diluted with methanol and analyzed by HPLC as described in section (a). Acridinium ester product 8b was observed eluting at Rt=15.2 minutes. The reaction mixture was worked up as described in section (b), Example 5. The acridinium ester 8b was refluxed in 10 mL of 1N HCl for 2 hours under nitrogen and cooled to room temperature. HPLC analysis of the reaction mixture indicated clean formation of the product 8c eluting at Rt=13.5 minutes. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 8c. Yield=22 mg (56% overall); MALDI-TOF MS 747.4 observed.

c) Compound 8d

A solution of compound 8c (22 mg, 29.5 umoles) in DMF (3.6 mL) and water (0.4 mL) was treated with diisopropylethylamine (26 uL, 5 equivalents) and TSTU (44 mg, 5 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=14.6 minutes and was the major component. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product 8d were combined, frozen at −80° C. and lyophilized to dryness. Yield=17.6 mg (70%); MALDI-TOF MS 843.9.0 observed.

The following reactions describe the synthesis of AZC3M-AE-NHS, compound 8d.

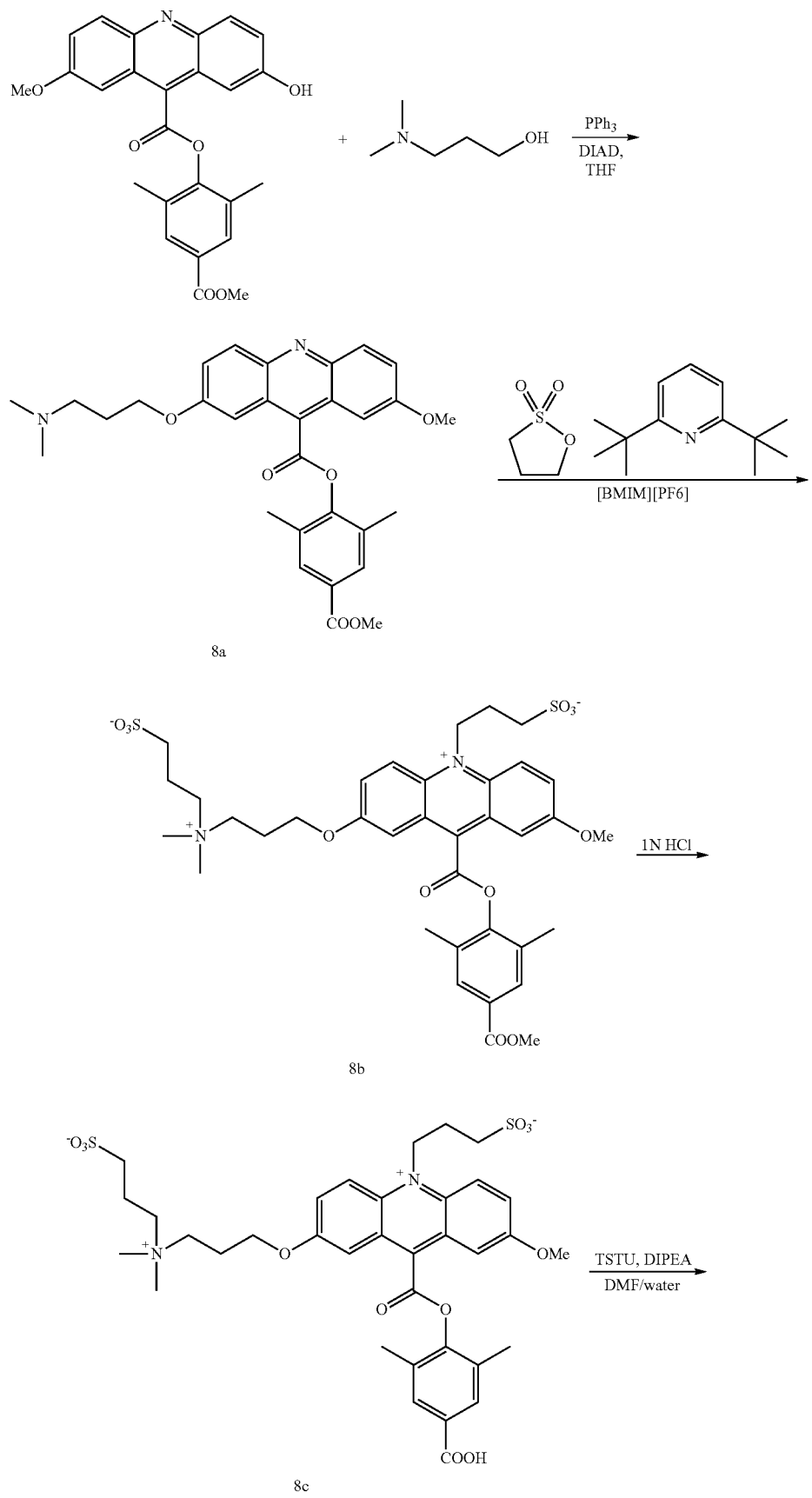

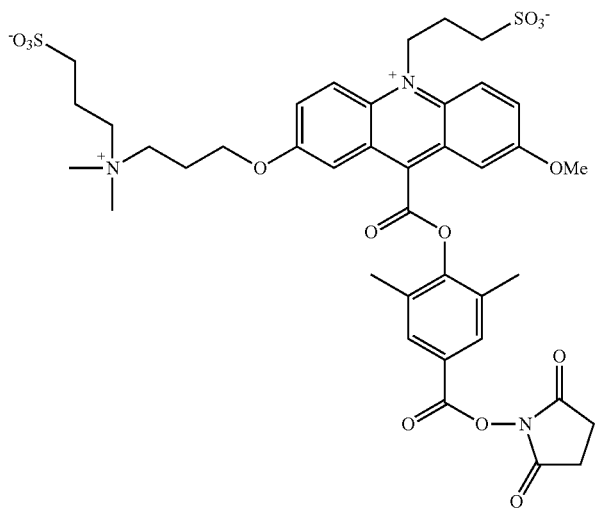

8d

Example 9

Synthesis of AZC6-AE-NHS, Compound 9d a) Compound 9a

A solution of 2-hydroxy-7-methoxyacridine methyl ester (25 mg, 0.058 mmol), 6-dimethylamino-1-hexanol (17 mg, 2 equivalents) and triphenylphosphine (30 mg, 2 equivalents) in anhydrous tetrahydrofuran (3 mL) was treated with diisopropyl azodicarboxylate (23 uL, 2 equivalents). The reaction was stirred at room temperature under nitrogen. After 2 hours, it was worked up as described in section (a), Example 5. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=22.5 minutes and was the major component. Yield 20 mg (63%); MALDI-TOF MS 559.8 observed.

b) Compound 9c

A mixture of compound 9a (20 mg, 35.9 umoles), 1,3-propane sultone (87 mg, 20 equivalents) and 2,6-di-tert-butylpyridine (59 uL, 7 equivalents) in the ionic liquid [BMIM][PF6] (0.5 mL) was heated at 150° C. for 24 hours. The reaction was then cooled to room temperature and a small portion (1-2 uL) was withdrawn, diluted with methanol and analyzed by HPLC as described in section (a). Acridinium ester product 9b was observed eluting at Rt=15.7 minutes (MALDI-TOF MS 803.9 observed). The reaction mixture was worked up as described in section (b), Example 5. The acridinium ester 9b was refluxed in 10 mL of 1N HCl for 2 hours under nitrogen and cooled to room temperature. HPLC analysis of the reaction mixture indicated clean formation of the product 9c eluting at Rt=14.9 minutes. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 9c. Yield=18.3 mg (65% overall); MALDI-TOF MS 790.4 observed.

c) Compound 9d

A solution of compound 9c (18.3 mg, 23.2 umoles) in DMF (3.6 mL) and water (0.4 mL) was treated with diisopropylethylamine (20 uL, 5 equivalents) and TSTU (35 mg, 5 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=16 minutes and was the major component. The product was purified by preparative HPLC using an YMC, $C_{18}$ 30×300 mm column and 30 minute gradient of 10→100% B (A=water with 0.05% TFA, B=MeCN with 0.05% TFA) at a solvent flow rate of 20 mL/minute and UV detection at 260 nm. The HPLC fractions containing product 9d were combined, frozen at −80° C. and lyophilized to dryness. Yield=14 mg (68%); MALDI-TOF MS 887.6 observed.

The following reactions describe the synthesis of AZC6M-AE-NHS, compound 9d.

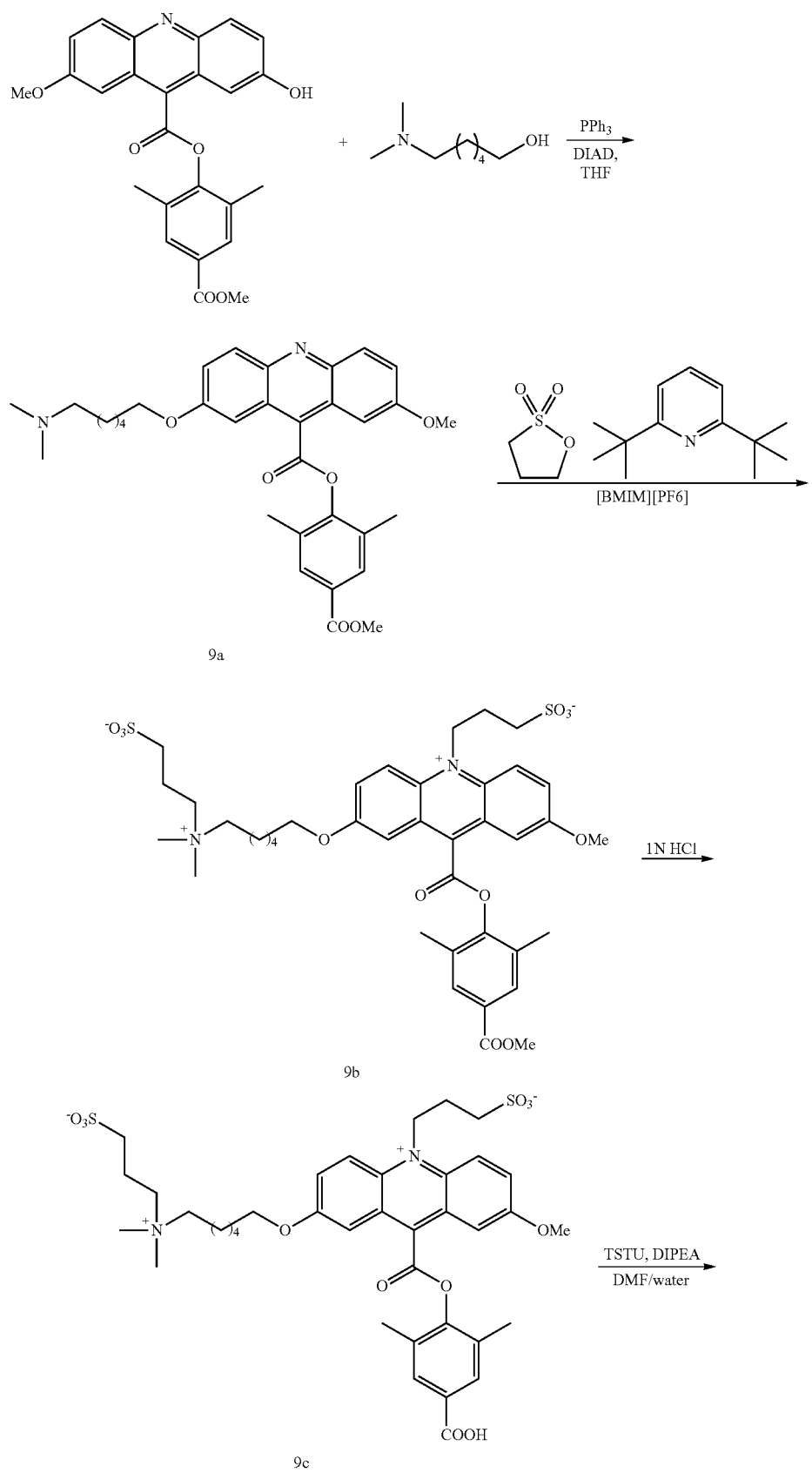

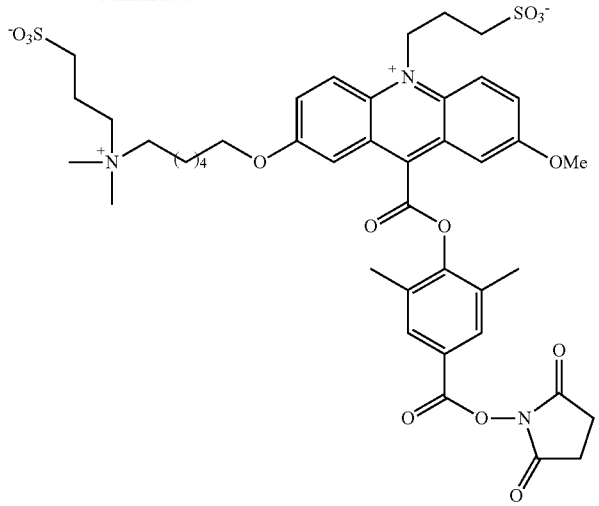

9d

Example 10

Synthesis of NSP-2Z-DMAE-NHS, Compound 10f a) Compound 10a

A solution of 4-bromobenzylbromide (2 g, 8 mmoles) in anhydrous tetrahydrofuran (10 mL) was treated with a 2.0 M solution of dimethylamine (20 mL) mL) in tetrahydrofuran. The reaction was stirred at room temperature for 3 days. The reaction mixture was then diluted with ethyl acetate (75 mL) and washed with 100 mL of saturated aqueous sodium bicarbonate solution. The ethyl acetate layer was separated and dried over anhydrous magnesium sulfate. TLC analysis on silica using 15% ethyl acetate in hexanes showed no starting material and the formation of a polar product of Rf=0.1. The ethyl acetate solution was concentrated under reduced pressure to afford a light yellow oil. Yield=1.63 g.

b) Compound 10b

A solution of isatin (1.12 g, 7.6 mmoles) in anhydrous DMF (20 mL) was cooled in an ice-bath under nitrogen and treated with sodium hydride (0.366 g, 1.2 equivalents, 60% dispersion in mineral oil). The reaction was stirred in the ice-bath for 30 minutes and then compound 10a (1.63 g, 7.6 mmoles) was added as a solution in DMF (5 mL) long with copper iodide (2.9 g, 2 equivalents). The reaction was heated at 140° C. under nitrogen for 24 hours. It was then cooled to room temperature, diluted with ethyl acetate (30 mL) and filtered. TLC on silica of the filtrate using 10% methanol in ethyl acetate as eluent showed a polar product of Rf ~0.1. The filtrate was concentrated under reduced pressure. The residue was suspended in 100 mL of 10% aqueous KOH and refluxed under nitrogen for 4 hours. The reaction mixture was then cooled to room temperature and acidified with 2 N HCl until pH 5. A yellow precipitate appeared which was collected by filtration and dried under vacuum. Yield=0.6 g. This compound was used as such for the next reaction.

c) Compound 10c

A suspension of compound 10b (0.2 g, 0.714 mmol) in anhydrous pyridine (15 mL) was treated with p-toluenesulfonyl chloride (272 mg, 2 equivalents) under nitrogen. After stirring briefly for 5 minutes, methyl 2,6-dimethyl-4-hydroxybenzoate (128 mg, 0.714 mmol) was added. The resulting reaction was stirred at room temperature for 3 days. The solvent was then removed under reduced pressure and the residue was partitioned between ethyl acetate (40 mL) and 1N HCl (50 mL). The HCl layer containing product was separated and washed twice with ethyl acetate (2×40 mL). The HCl solution was then cooled in an ice bath and treated dropwise with 5% aqueous KOH until a yellow precipitate separated out (pH ~8). This suspension was extracted with ethyl acetate (2×50 mL). The combined ethyl acetate extracts were washed once with water and dried over anhydrous magnesium sulfate. The solvent was then removed under reduced pressure and the crude product was purified by flash chromatography on silica using ethyl acetate as eluent. Yield=95 mg (30%); MALDI-TOF MS 443.7 observed.

d) Compound 10e

A mixture of compound 10c (22 mg, 49.5 umoles), 1,3-propane sultone (120 mg, 20 equivalents) and 2,6-di-tert-butylpyridine (81.5 uL, 7.5 equivalents) in the ionic liquid [BMIM][PF6] (0.5 mL) was heated at 150° C. for 24 hours. The reaction was then cooled to room temperature and a small portion (1-2 uL) was withdrawn, diluted with methanol and analyzed by HPLC using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product 10d was observed eluting at $R_t$=17.2 minutes (~40% conversion). The reaction mixture was worked up as described in section (b), Example 5. The acridinium ester 10d was refluxed in 10 mL of 1N HCl for 2 hours under nitrogen and cooled to room temperature. HPLC analysis of the reaction mixture indicated clean formation of the product 10e eluting at Rt=14.0 minutes. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product were combined and concentrated under reduced pressure to give compound 10e. Yield=14.5 mg (44% overall); MALDI-TOF MS 673.3 observed.

c) Compound 10f

A solution of compound 10e (14.5 mg, 21.5 umoles) in DMF (1.8 mL) and water (0.2 mL) was treated with diisopropylethylamine (18.8 uL, 5 equivalents) and TSTU (32 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=16.5 minutes and was the major component. The product was purified by preparative HPLC using an YMC, $C_{18}$ 30×300 mm column and 30 minute gradient of 10→70% B (A=water with 0.05% TFA, B=MeCN with 0.05% TFA) at a solvent flow rate of 20 mL/minute and UV detection at 260 nm. The HPLC fractions containing product 10f were combined, frozen at −80° C. and lyophilized to dryness. Yield=14 mg (85%); MALDI-TOF MS 769.5 observed.

The following reactions describe the synthesis of NSP-2Z-DMAE-NHS, compound 10f.

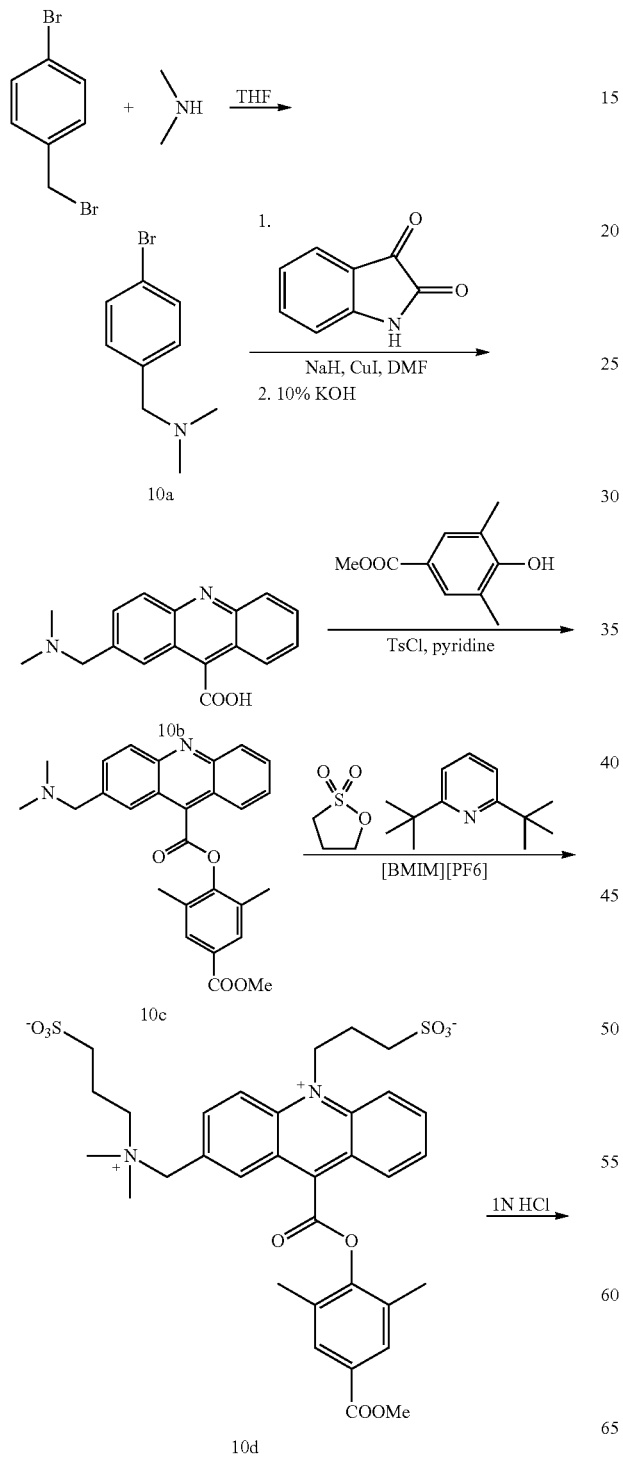

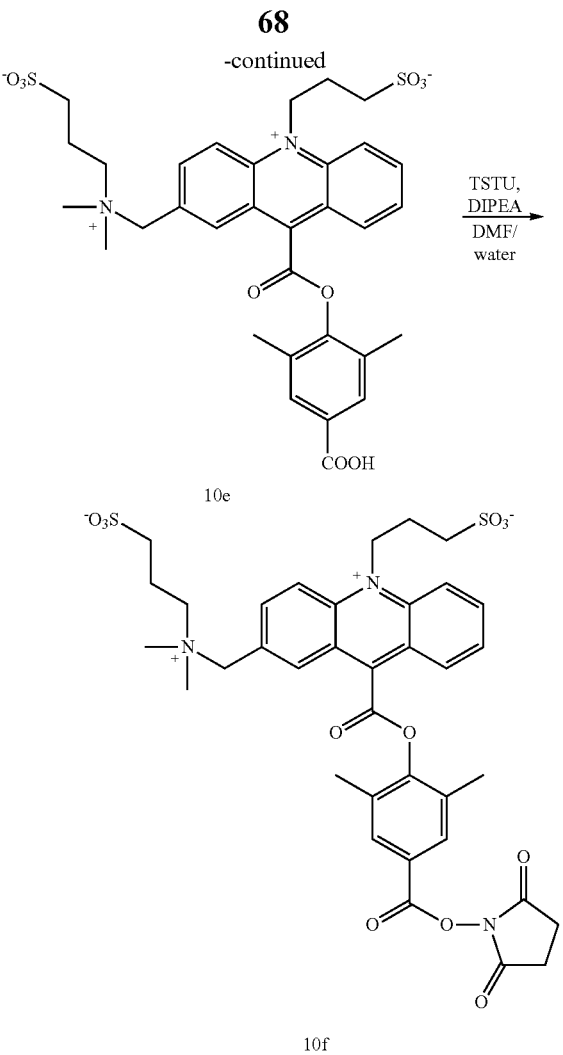

Example 11

Synthesis of NSP-DMAE-Z-NHS, Compound 11f a) Compound 11a

A solution of N,N-bis(3-aminopropyl)methyl amine (1 g, 6.9 mmoles) in chloroform (40 mL) was treated with benzyloxycarbonylsuccinimide (3.78 g, 2.2 equivalents). The reaction was stirred at room temperature for 16 hours. TLC analysis on silica of the reaction mixture using 15% methanol in ethyl acetate showed the formation of a polar product in a clean reaction. The reaction mixture was diluted with chloroform (40 mL) and washed with saturated aqueous sodium bicarbonate solution. It was then dried over anhydrous magnesium sulfate, filtered and concentrated under reduced pressure to afford a viscous oil that solidified upon storage to a waxy solid. Yield=3.2 g; MALDI-TOF MS 414.4 observed.

b) Compound 11b

A solution of compound 11a (1.2 g, 2.9 mmoles) in anhydrous DMF (15 mL) was treated with 1,3-propane sultone (0.71 g, 2 equivalents). The reaction was heated at 145° C. under nitrogen for 1 hour. HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=19.6 minutes (~80% conversion) with starting material eluting at Rt=21.6 minutes. The reaction mixture was concentrated under reduced pressure and the recovered oil was dissolved in methanol (20 mL). TLC analysis on silica using 40% methanol, 60% ethyl acetate indicated clean separation of product (Rf ~0.2) from starting material (Rf ~0.3). The above reaction was repeated on the same scale and the combined reaction mixture was purified by flash chromatography on silica using 40% methanol, 60% ethyl acetate as eluent. Yield=1.55 g (60%); white foam; MALDI-TOF MS 536.4 observed.

c) Compound 11c

Compound 11b (0.8 g, 1.49 mmoles) was stirred in 15 mL of 33% HBr/AcOH at room temperature for 24 hours. Ether (100 mL) was then added and a white, granular solid separated out. The product was allowed to settle and the ether was decanted. This process was repeated twice with ether (2×50 mL). Finally, the product was dried under vacuum. The recovered viscous oil was dissolved in 5-6 mL water, frozen at −80° C. and lyophilized to dryness to afford a glassy solid. Yield=0.766 g (quantitative); MALDI-TOF MS 268.2 observed. TLC analysis on silica using 25% ammonia, 75% methanol and ninhydrin for visualization showed a single spot of Rf ~0.2.

d) Compound 11d

A solution of NSP-DMAE (30 mg, 61 umoles, U.S. Pat. No. 6,664,043 B2) in DMF (3 mL) was treated with diisopropylethylamine (16 uL, 1.5 equivalents) and TSTU (22 mg, 1.2 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=20 minutes and was the major component. Half of this DMF solution (1.5 mL) of the NHS ester was added drop wise to a solution of compound 11e (50 mg, 0.187 mmol, free amine form) dissolved in DMF (1 mL) and 0.15 M sodium bicarbonate (1 mL). The reaction was stirred at room temperature. After 3 hours, HPLC analysis showed clean conversion to the product 11d, eluting at 12.4 minutes. Using a 40 minute gradient of 10→40% B (A=water with 0.05% TFA, B=MeCN with 0.05% TFA), the product eluted at Rt=19.2 minutes.

The product was purified by preparative HPLC using an YMC, $C_{18}$ 30×300 mm column and 40 minute gradient of 10→40% B (A=water with 0.05% TFA, B=MeCN with 0.05% TFA) at a solvent flow rate of 20 mL/minute and UV detection at 260 nm. The HPLC fractions containing product 11d were combined and concentrated under reduced pressure. Yield=19 mg (83%); MALDI-TOF MS 743.2 observed.

e) Compound 11f

A solution of compound 11d (45 mg, 60.6 umoles) in methanol (3.6 mL) and water (0.4 mL) was treated with diisopropylethylamine (53 uL, 5 equivalents) and glutaric anhydride (35 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product 11e was observed eluting at Rt=14 minutes and was the major component. The solvent was then removed under reduced pressure. The residue was dissolved in DMF (3.6 mL) and water (0.4 mL). This solution was treated with diisopropylethylamine (106 uL, 10 equivalents) and TSTU (182 mg, 10 equivalents). The reaction was stirred at room temperature. After 10 minutes, HPLC analysis showed complete conversion to the product 11f eluting at Rt=15.3 minutes. The product was purified by preparative HPLC using an YMC, $C_{18}$ 30×300 mm column and 40 minute gradient of 10→40% B (A=water with 0.05% TFA, B=MeCN with 0.05% TFA) at a solvent flow rate of 20 mL/minute and UV detection at 260 nm. The HPLC fractions containing product 11f were combined, frozen at −80° C. and lyophilized to dryness. Yield=28.7 mg (50%); MALDI-TOF MS 955.2 observed.

The following reactions describe the synthesis of NSP-DMAE-Z-NHS, compound 11f.

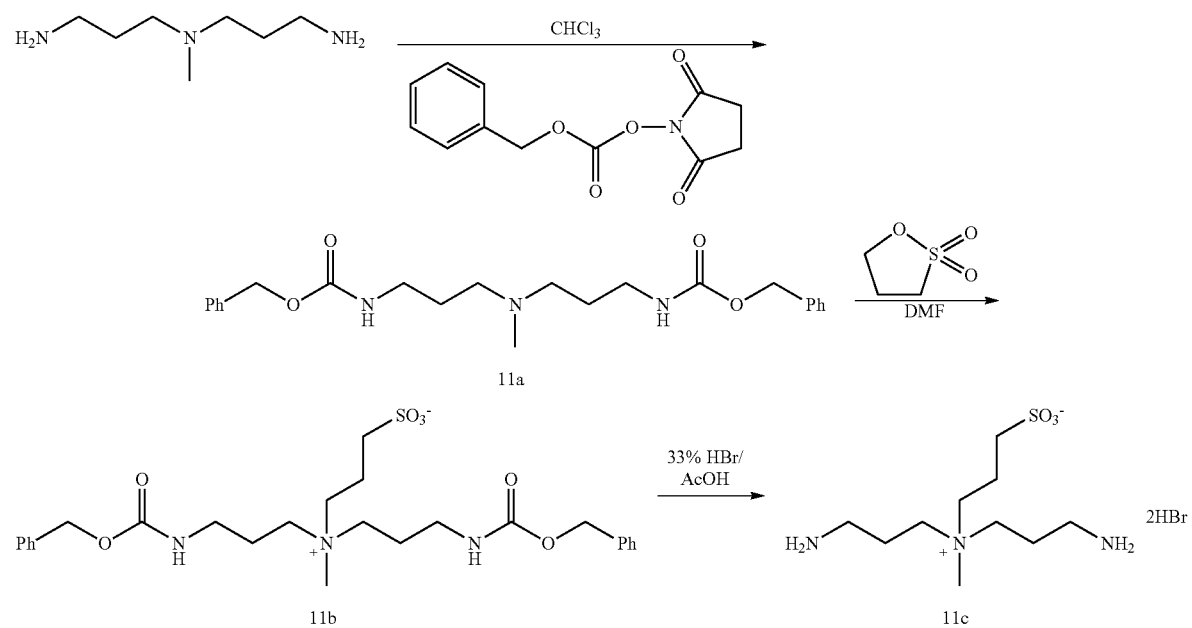

-continued
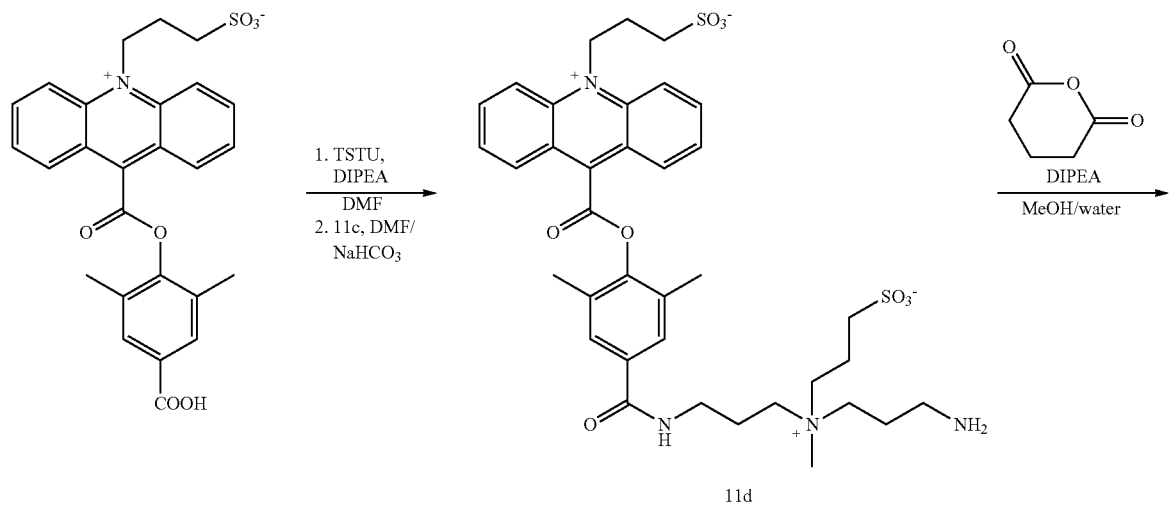
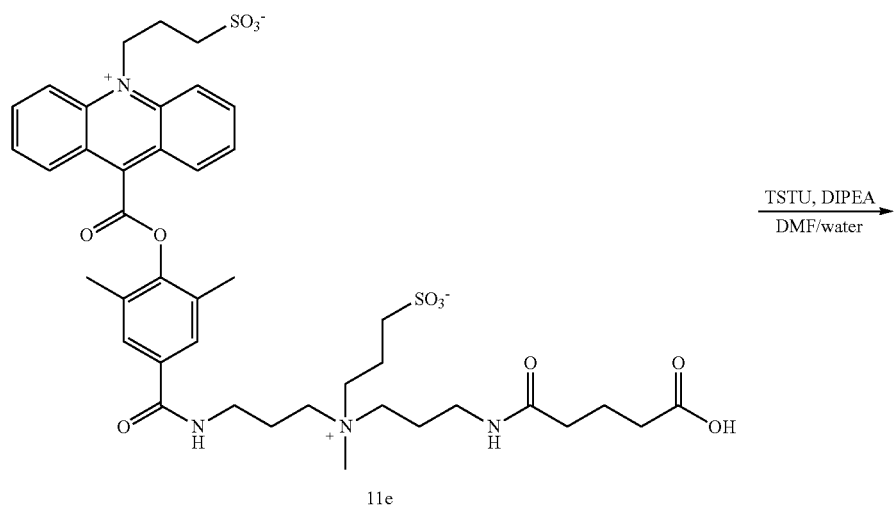
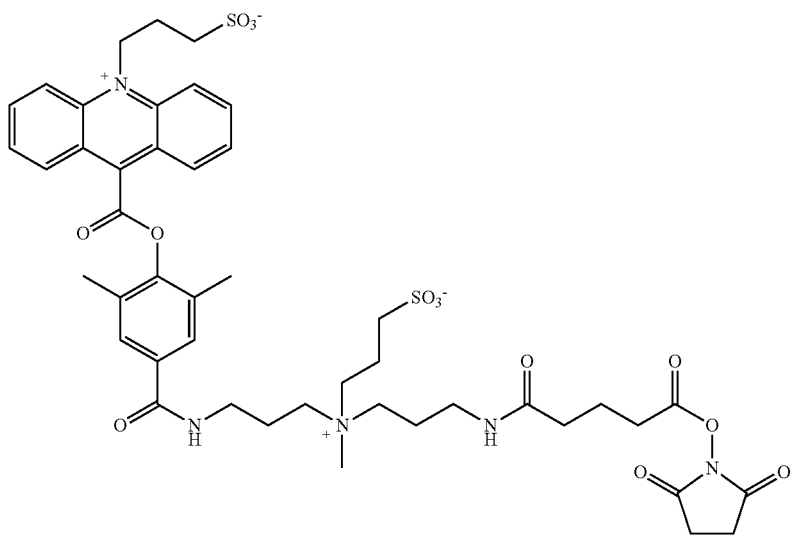

Example 12

Synthesis of NSP-2,7-DMG-DMAE-Z-NHS, Compound 12h a) 1,3-Dimethoxyglycerol, Compound 12a

Anhydrous methanol (100 mL) was treated with potassium hydroxide pellets (25 g, 0.446 mol) and the suspension was stirred at room temperature until all the base had dissolved. This solution was then cooled in an ice-bath and epichlorohydrin (0.223 mol, 20.6 g) was added drop wise. After completion of the addition, the reaction was warmed to room temperature and heated in an oil bath at 75-80° C. under nitrogen for 16 hours. The reaction was then cooled to room temperature and filtered. The filtrate was concentrated under reduced pressure. The recovered oil was dissolved in ethyl acetate (150 mL) and filtered again and then concentrated under reduced pressure. A colorless oil (21.5 g) was recovered that was purified by vacuum distillation to afford 12.9 g (50%) of 1,3-dimethoxyglycerol, compound 12a.

b) Compound 12b

A solution of 1,3-dimethoxyglycerol, compound 12a (1 g, 8.3 mmoles) in anhydrous pyridine (20 mL) was treated with p-toluenesulfonyl chloride (2.38 g, 1.5 equivalents) and 4-dimethylaminopyridine (0.253 g, 0.25 equivalent). The reaction was stirred at room temperature under nitrogen for 3 days. The solvent was then removed under reduced pressure and the residue was partitioned between ethyl acetate (100 mL) and 1N HCl (50 mL). The ethyl acetate layer was separated and washed once with 1 n HCl (50 mL), followed by aqueous sodium bicarbonate (3×50 mL). It was then dried over anhydrous magnesium sulfate, filtered and concentrated under reduced pressure. The crude product (2.5 g) was purified by flash chromatography on silica using 20% ethyl acetate in hexanes as eluent. Yield=1.79 g (65%).

c) Compound 12c

A solution of 2,7-dihydroxyacridine methyl ester (0.1 g, 0.24 mmol), compound 12b (0.4 g, 1.45 mmoles) and cesium carbonate (0.2 g, 2.5 equivalents) in anhydrous DMF (6 mL) was heated in an oil bath at 90-100° C. under nitrogen. After 5 hours, the reaction was cooled to room temperature. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=26.5 minutes and was the major component. The solvent was then removed under reduced pressure and the residue was partitioned between ethyl acetate (50 mL) and water (50 mL). The ethyl acetate layer was separated and washed twice with water (2×50 mL). It was then dried over anhydrous magnesium sulfate, filtered and concentrated under reduced pressure. The crude product (0.37 g) was purified by preparative TLC on silica using 1:1, ethyl acetate/hexanes. Purified Yield=58 mg (40%); MALDI-TOF MS 623.1 observed.

d) Compound 12e

A mixture of compound 12c (58 mg, 93.25 umoles), distilled 1,3-propane sultone (1.14 g, 100 equivalents) and sodium bicarbonate (78 mg, 10 equivalents) was heated at 140-150° C. After 2 h, the reaction was cooled to room temperature. HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product 12d was observed eluting at Rt=20 minutes and was the major component. The reaction mixture was treated with 20 mL of 1:1, ethyl acetate/hexanes and the mixture was sonicated briefly to disperse the gum. The product was allowed to settle, and the solvent was removed by decantation. The crude product was dried under vacuum and then suspended in 10 mL of 1N HCl and refluxed under nitrogen for 3 hours. It was then cooled to room temperature and analyzed by HPLC which indicated complete hydrolysis of the methyl ester with the product 12e, eluting at Rt=17.0 minutes. The product was purified by preparative HPLC using an YMC, $C_{18}$ 30×300 mm column and 40 minute gradient of 10→100% B (A=water with 0.05% TFA, B=MeCN with 0.05% TFA) at a solvent flow rate of 20 mL/minute and UV detection at 260 nm. The HPLC fractions containing product 12e were combined and concentrated under reduced pressure. Yield=56 mg (82%); MALDI-TOF MS 730.9 observed.

e) Compound 12f

A solution of compound 12e (55 mg, 75.3 umoles) in DMF (3 mL) was treated with diisopropylethylamine (20 uL, 1.5 equivalents) and TSTU (27 mg, 1.2 equivalents). The reaction was stirred at room temperature. After 10 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. The NHS ester was observed eluting at Rt=18 minutes and was the major component. The DMF solution of the NHS ester was then added drop wise to a solution of compound 11e (168 mg, 0.376 mmol, 2HBr salt) dissolved in water (1.68 mL) and 0.5 M sodium bicarbonate (1.68 mL). The reaction was stirred at room temperature. After 30 minutes, HPLC analysis showed clean conversion to the product 12e, eluting at 12.4 minutes.

The product was purified by preparative HPLC using an YMC, $C_{18}$ 30×300 mm column and 40 minute gradient of 10→100% B (A=water with 0.05% TFA, B=MeCN with 0.05% TFA) at a solvent flow rate of 20 mL/minute and UV detection at 260 nm. The HPLC fractions containing product 12f were combined and concentrated under reduced pressure. Yield=63.8 mg (86%); MALDI-TOF 979.1MS observed.

f) Compound 12h

A solution of compound 12f (63.8 mg, 65.2 umoles) in methanol (4.0 mL) was treated with diisopropylethylamine (57 uL, 5 equivalents) and glutaric anhydride (74 mg, 5 equivalents). The reaction was stirred at room temperature. After 15 minutes, HPLC analysis of a small portion of the reaction mixture was performed using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product 12g was observed eluting at Rt=13.5 minutes and was the major component. The solvent was then removed under reduced pressure. The residue was dissolved in DMF (5.4 mL) and water (0.6 mL). This solution was treated with diisopropylethylamine (114 uL, 10 equivalents) and TSTU (200 mg, 10 equivalents). The reaction was stirred at room temperature. After 15 minutes, HPLC analysis showed complete conversion to the product 12h eluting at Rt=14.3 minutes. The product was purified by preparative HPLC using an YMC, $C_{18}$ 30×300 mm column and 40 minute gradient of 10→70% B (A=water with 0.05% TFA, B=MeCN with 0.05% TFA) at a solvent flow rate of 20 mL/minute and UV detection at 260 nm. The HPLC fractions containing product 12h were combined, frozen at −80° C. and lyophilized to dryness. Yield=49.3 mg (63%); MALDI-TOF MS 1188.9 observed.
The following reactions describe the synthesis of NSP-2, 7-DMG-DMAE-Z-NHS, compound 12h.
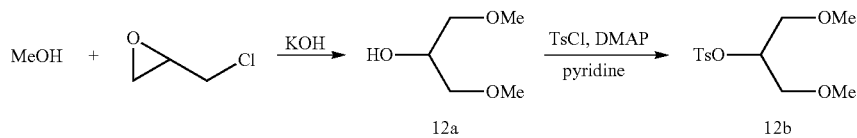
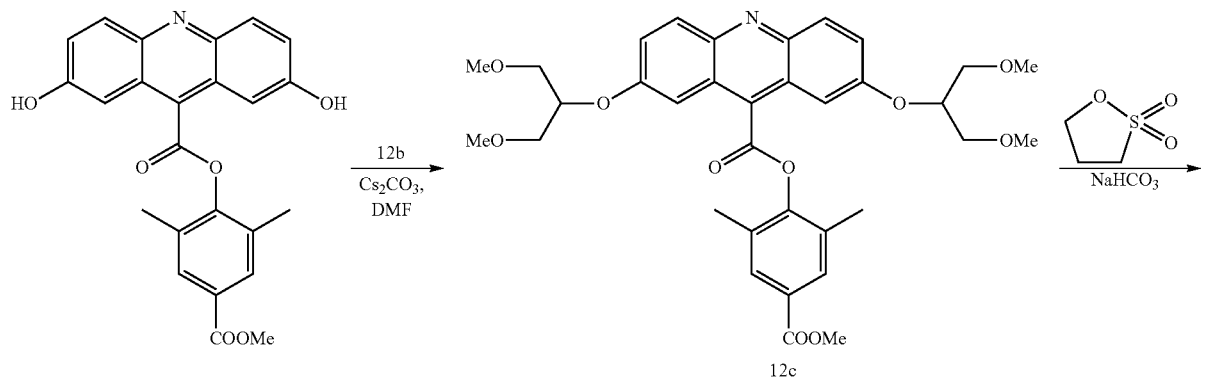
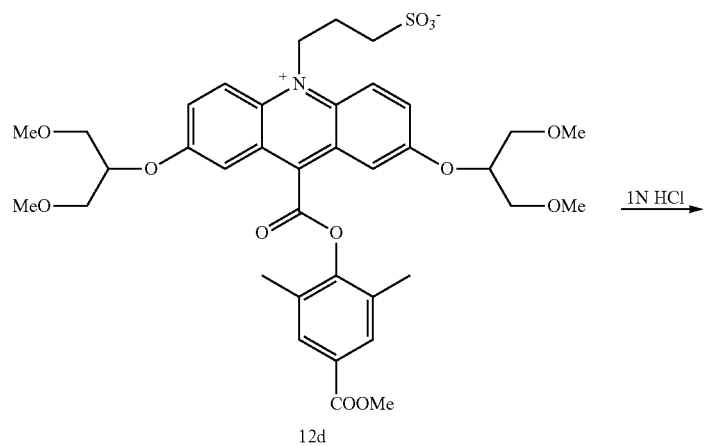
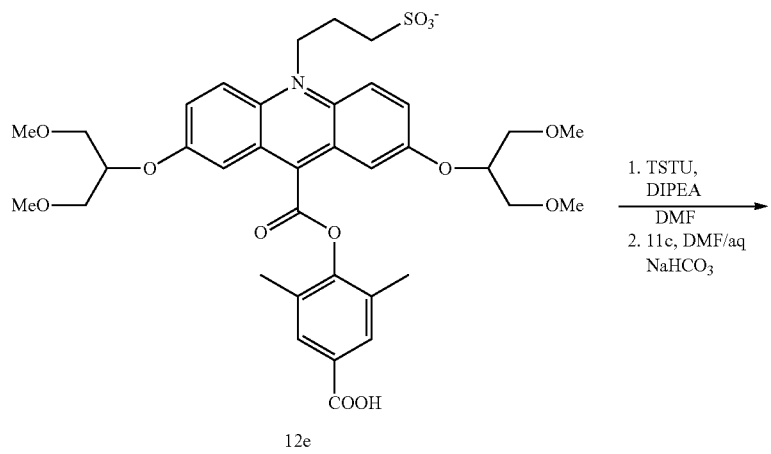

77 78
-continued
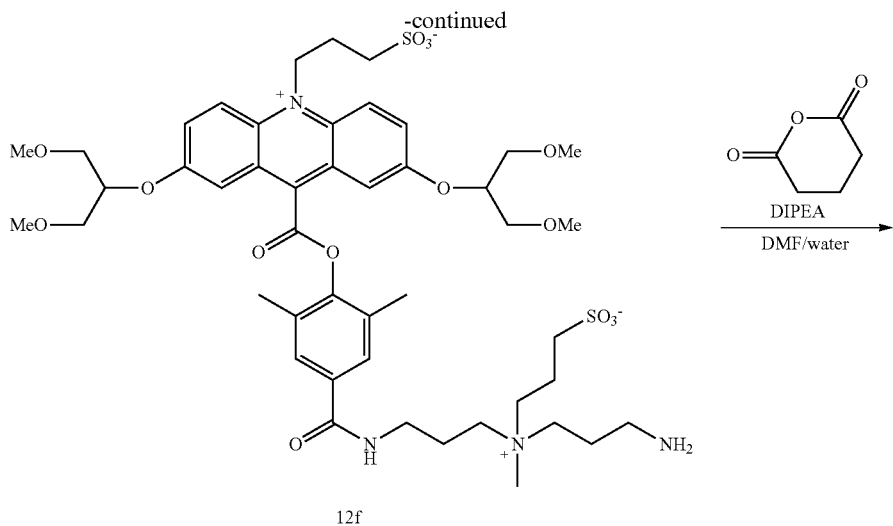
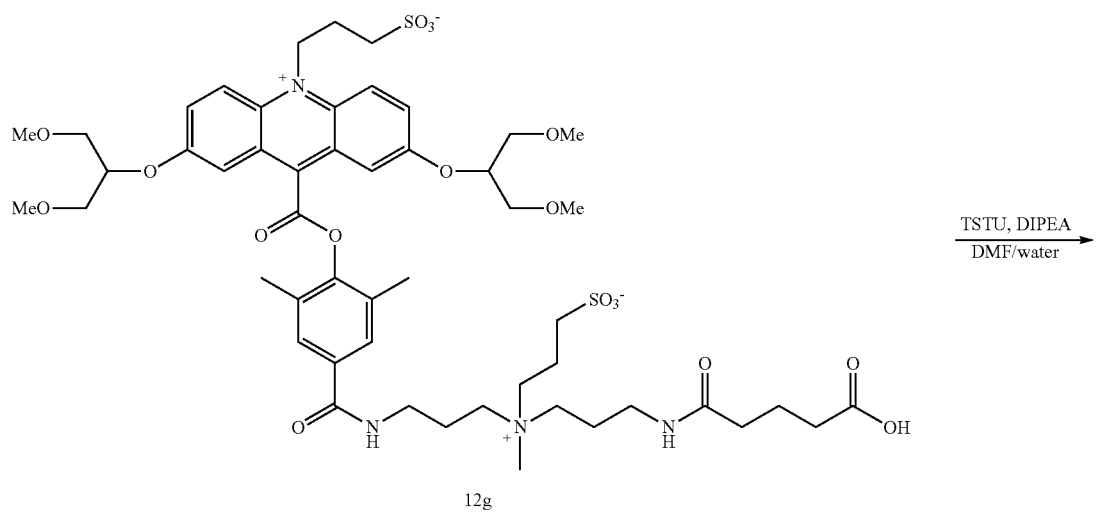
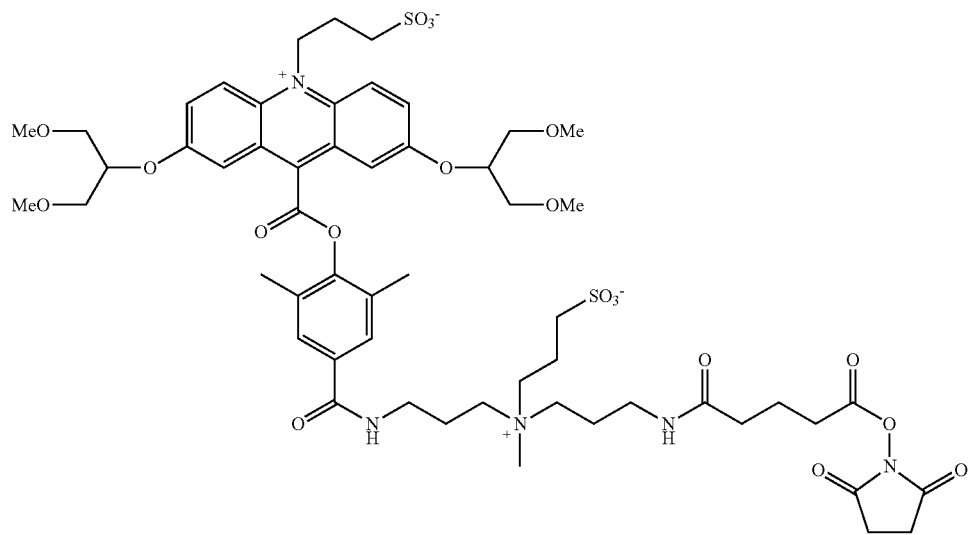

Example 13

Synthesis of NSP-DMAE-Z2-NHS, Compound 13e a) Compound 13a

A solution of 2-chloroethanesulfonyl chloride (0.126 mL, 1.2 mmoles) in anhydrous ether (5 mL) was cooled to −5° C. in an ice-salt bath under a nitrogen atmosphere and treated with 2,6-lutidine (0.14 mL, 1.2 mmoles) in one portion. The reaction was stirred at −5° C. for 30 minutes then warmed to room temperature. The reaction was then filtered through glass wool into a stirred solution of 11a (0.325 g, 0.79 mmoles) dissolved in acetic acid (5 mL). After 4-5 hours, the solvent was removed under reduced pressure. The residue was suspended in toluene (5 mL) and concentrated under reduced pressure. The crude product was partitioned between water (50 mL) and ethyl acetate (50 mL). The aqueous layer was separated and washed once with chloroform (50 mL). The aqueous layer was adjusted to pH 9 with ammonium hydroxide and extracted with ethyl acetate (3×50 mL). The aqueous layer was then concentrated under reduced pressure to afford a white solid. Yield=0.18 g, (43%); MALDI-TOF MS 522.8 observed).

HPLC analysis of a small portion of the product was performed using a Phenomenex PRODIGY, $C_{18}$ 10 mm×25 cm column and a 30 minute gradient of 10→70% B (A=water with 0.05% TFA, B=MeCN with 0.05% TFA) at a flow rate of 4.0 mL/minute and UV detection at 260 nm. Clean product was observed eluting at Rt=21 mins with no starting material.

b) Compound 13b

Compound 13a (78 mg, 0.15 mmoles) was stirred in 5 mL of 33% HBr/AcOH at room temperature for 24 hours. Ether (75 mL) was then added and a white, granular solid separated out. The product was allowed to settle and the ether was decanted. This process was repeated twice with ether (2×50 mL). Finally, the product was dried under vacuum. Yield=48 mg (77%). This material was used as such for the next reaction.

c) Compound 13c

A solution of NSP-DMAE (14 mg, 28.4 umoles, U.S. Pat. No. 6,664,043 B2) in DMF (1 mL) was treated with diisopropylethylamine (7.4 uL, 1.5 equivalents) and TSTU (10.3 mg, 1.2 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=20 minutes and was the major component. This DMF solution of the NHS ester was added drop wise to a solution of compound 13b (48 mg, 0.116 mmoles, HBr salt) dissolved in 0.25 M sodium bicarbonate (3 mL). The reaction was stirred at room temperature. After 30 minutes, HPLC analysis showed clean conversion to the product 13c, eluting at 12.4 minutes.

The product was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. The HPLC fractions containing product 13c were combined and concentrated under reduced pressure. Yield=19 mg (90%).

d) Compound 13e

A solution of compound 13c (19 mg, 26.1 umoles) in methanol (3.6 mL) and water (0.4 mL) was treated with diisopropylethylamine (22.8 uL, 5 equivalents) and glutaric anhydride (15 mg, 5 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product 13d was observed eluting at Rt=14.6 minutes and was the major component (>80%). The solvent was then removed under reduced pressure. The residue was dissolved in DMF (3.6 mL) and water (0.4 mL). This solution was treated with diisopropylethylamine (45.6 uL, 10 equivalents) and TSTU (79 mg, 10 equivalents). The reaction was stirred at room temperature. After 15 minutes, HPLC analysis showed complete conversion to the product 13e eluting at Rt=15.7 minutes. The product was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. The HPLC fractions containing product 13e were combined, frozen at −80° C. and lyophilized to dryness. Yield=15 mg (60%).

The following reactions describe the synthesis of NSP-DMAE-Z2-NHS, compound 13e.

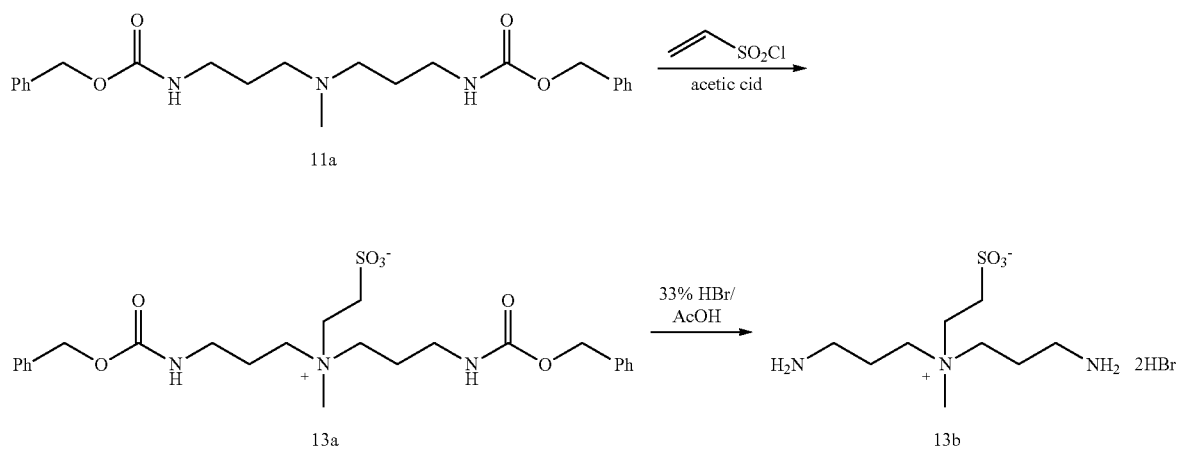

81
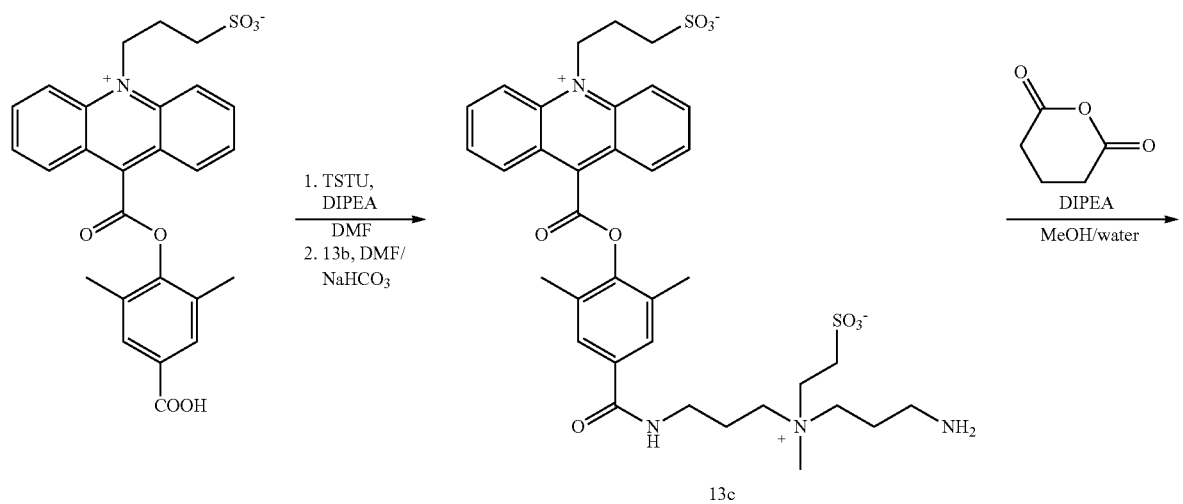
82
-continued
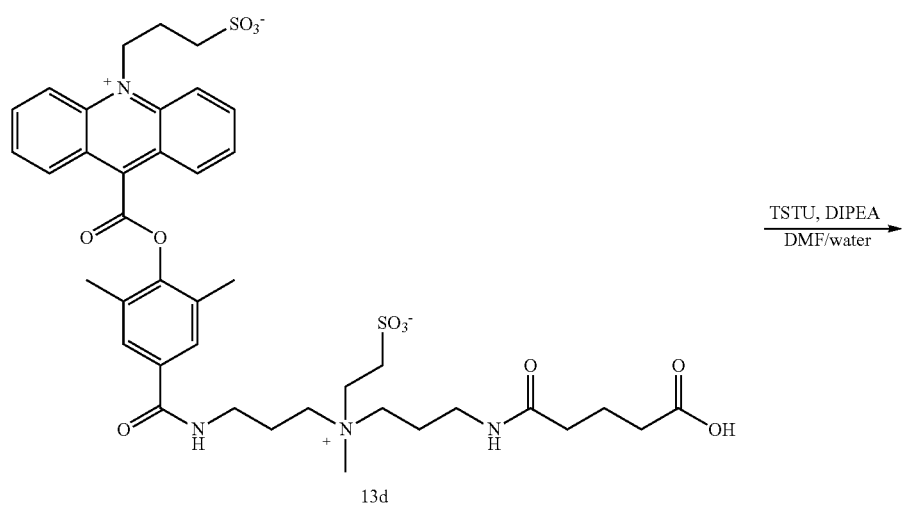
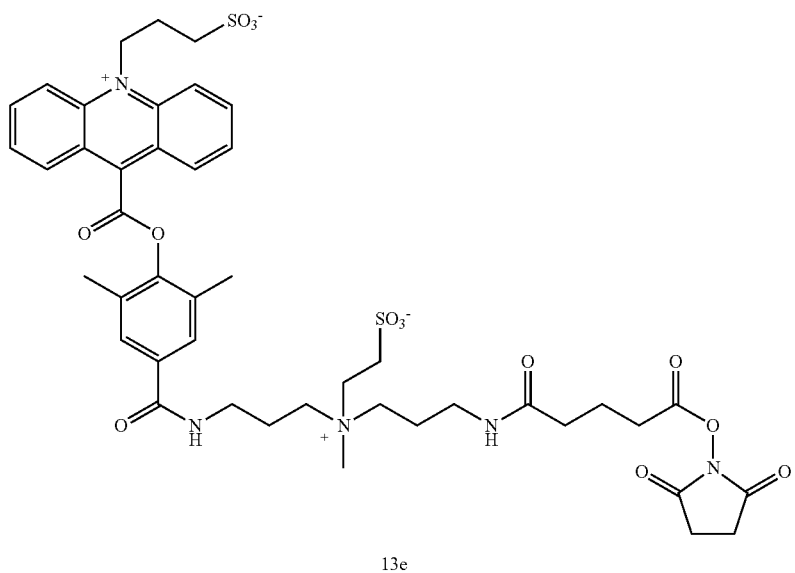

Example 14

Synthesis of NSP-DMAE-ZCB-NHS, Compound 14d a) Compound 14a

A solution of 11a (0.6 g, 1.45 mmoles) dissolved in MeCN (5 mL) was treated with acrylic acid (1 mL, 1.45 mmoles). The reaction was stirred at room temperature for 36 hours. The solvent was then removed under reduced pressure and the crude product was purified by flash chromatography on silica using 3:2, MeOH:EtOAc as eluent. The fractions containing product were combined and concentrated under reduced pressure. Yield=0.432 g, (61%); MALDI-TOF MS 486.1 observed).

b) Compound 14b

Compound 14a (0.43 g, 0.88 mmoles) was stirred in 10 mL of 33% HBr/AcOH at room temperature for 24 hours. Ether (100 mL) was then added and a white, granular solid separated out. The product was allowed to settle and the ether was decanted. This process was repeated four times with ether (4×50 mL). Finally, the product was dried under vacuum. It was then dissolved in water (5 mL), frozen and lyophilized. Yield=0.35 g (quantitative); MALDI-TOF MS 218.3 observed.

c) Compound 14c

A solution of NSP-DMAE (25 mg, 51.0 umoles, U.S. Pat. No. 6,664,043 B2) in DMF (2 mL) was treated with diisopropylethylamine (11.3 uL, 1.5 equivalents) and TSTU (18.3 mg, 1.2 equivalents). The reaction was stirred at room temperature. After 30 minutes, this DMF solution of the NHS ester was added drop wise to a solution of compound 14b (80 mg, 0.2 mmoles, HBr salt) dissolved in 0.25 M sodium bicarbonate (0.8 mL). The reaction was stirred at room temperature. After 30 minutes, HPLC analysis performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm, showed clean conversion to the product 14c, eluting at 12.0 minutes.

The product was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. The HPLC fractions containing product 14c were combined and concentrated under reduced pressure. Yield=38 mg (quantitative); MALDI-TOF MS 692.9 observed.

e) Compound 14d

A solution of compound 14c (20 mg, 29 umoles) in DMF (1.0 mL) and DMSO (2.0 mL) was treated with diisopropylthylamine (8.6 uL, 2 equivalents) was added drop wise to a stirred solution of disuccinimidyl glutarate (38 mg, 0.117 mmoles) in DMF (1 mL). The reaction was stirred at room temperature. After 60 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product 14d was observed eluting at Rt=15.0 minutes and was the major component (>70%). The product was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. The HPLC fractions containing product 14d were combined, frozen at −80° C. and lyophilized to dryness. Yield=4 mg (15%); MALDI-TOF MS 905.5 observed.

The following reactions describe the synthesis of NSP-DMAE-ZCB-NHS, compound 14d.

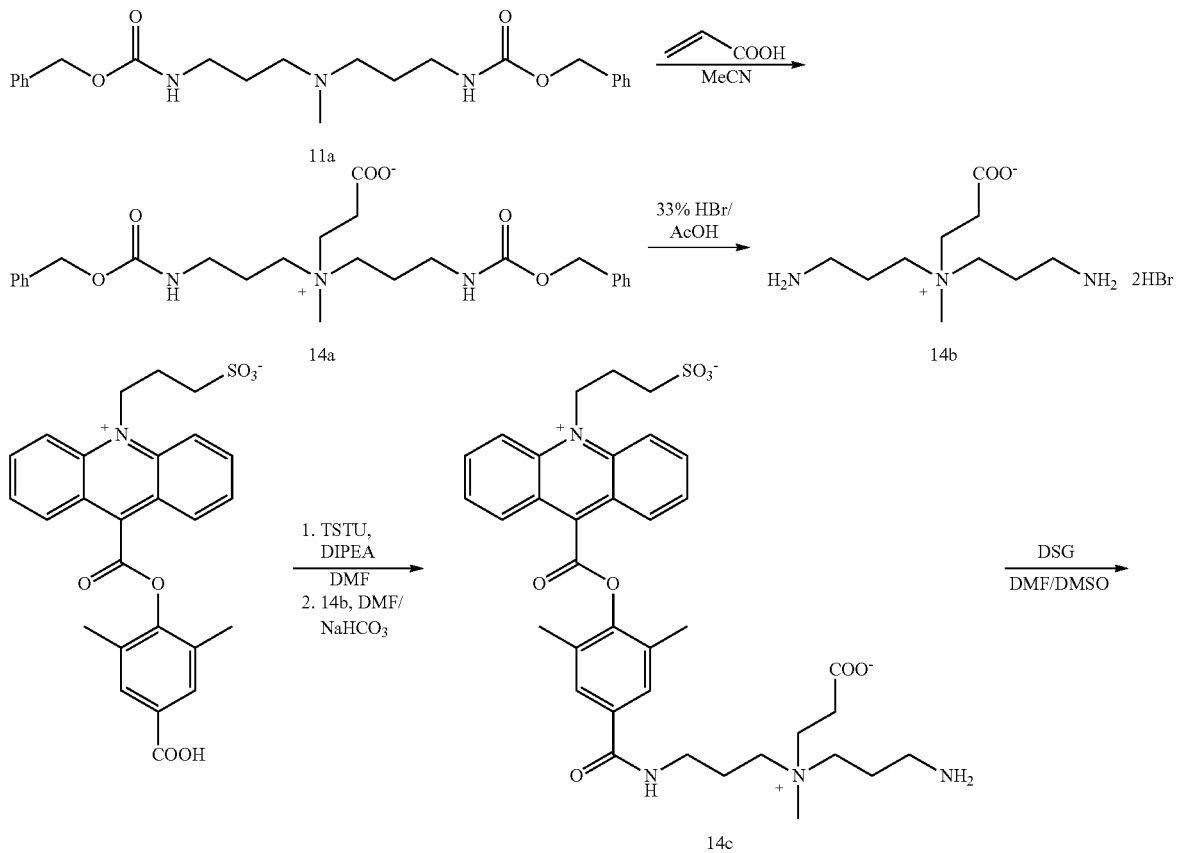

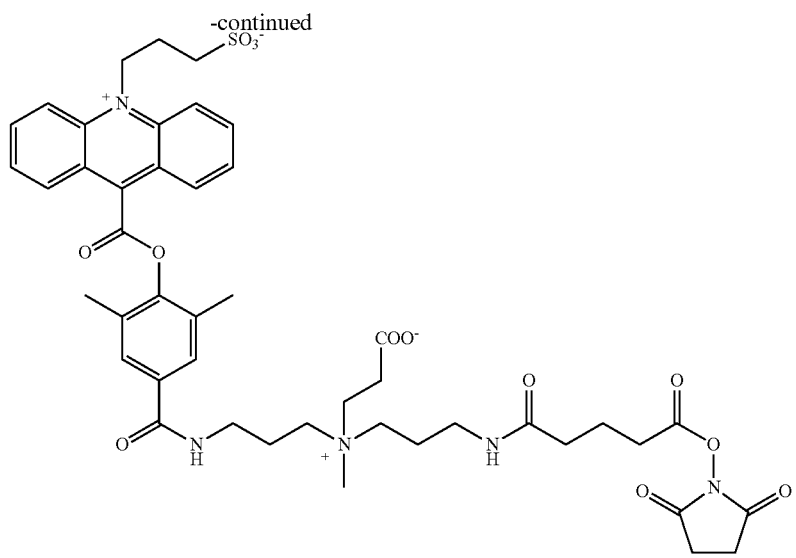

14d

Example 15

Synthesis of CN-NSP-DMAE-Z3-NHS, Compound 15f a) Compound 15a

A suspension of NSP-DMAE methyl ester (0.223 g, 0.44 mmoles) in thionyl chloride (5 mL) was heated at 80° C. under a nitrogen atmosphere with vigorous stirring. After one hour a dark solution was formed which was cooled to room temperature. Hexane (50 mL) was added and a dark brown, sticky sold separated out. The hexane was decanted and the residue was rinsed once with hexane (25 mL) and dried very briefly under vacuum. To this sticky solid was added a solution of N,N-dimethylethylenediamine (10 mL, excess) in anhydrous MeCN (10 mL). A dark brown solution was formed which was stirred at room temperature. After 15 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product 15a was observed eluting as abroad peak at Rt=19 minutes. The reaction mixture was concentrated under reduced pressure and the residue was dissolved in methanol (5 mL), diluted with toluene (15 mL) was concentrated under reduced pressure to afford a stick brown foam. Crude Yield=0.46 g. The product was purified by flash chromatography on silica using methanol as eluent. Yield=0.22 g, (87%); MALDI-TOF MS 577.9 observed.

b) Compound 15b

A mixture of compound 15a, (0.22 g, 0.38 mmoles), distilled 1,3-propane sultone (0.465 g, 10 equivalents and 2,6-di-tertbutylpyridine (0.42 mL, 5 equivalents) in [BMIM][PF6] (3 mL) was heated at 155° C. for 16 hours with vigorous stirring. It was then cooled to room temperature and ethyl acetate (100 mL) was added. The product precipitated out and was collected by filtration and rinsed with ethyl acetate (25 mL) and methanol (20 mL). The crude product was then transferred to a RB flask with 50 mL of 1:1 water/methanol. HPLC analysis of a small portion of the crude reaction mixture was performed using a Phenomenex, $C_{18}$ 4.6 mm×25 cm column and a 40 minute gradient of 10→40% B (A=water with 0.05% TFA, B=MeCN with 0.05% TFA) at a flow rate of 1.0 mL/minute and UV detection at 260 nm. Product was observed eluting at Rt=33 minutes (~90% conversion). Evaporation of the aqueous solution under reduced pressure gave 0.35 g of a brown solid. MALDI-TOF MS 699.2 observed. This material was used as such for the next reaction.

c) Compound 15c

Compound 15 b (0.35 g, crude) was suspended in 1N HCl (20 mL) and was heated under reflux under a nitrogen atmosphere for 1.5 hours. HPLC analysis as indicated in section (b) showed product eluting at Rt=27 minutes. The reaction was cooled to room temperature. The product 15c was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. HPLC fractions containing the product were combined and concentrated under reduced pressure. Yield=14 mg; MALDI-TOF MS 685.7 observed.

d) Compound 15d

A solution of compound 15c (14 mg, 20 umoles) in DMF (2 mL) was treated with diisopropylethylamine (6 uL, 2 equivalents) and TSTU (12.3 mg, 2 equivalents). The reaction was stirred at room temperature. After 10 minutes, HPLC analysis of a small portion of the crude reaction mixture was performed using a Phenomenex, $C_{18}$ 4.6 mm×25 cm column and a 40 minute gradient of 10→40% B (A=water with 0.05% TFA, B=MeCN with 0.05% TFA) at a flow rate of 1.0 mL/minute and UV detection at 260 nm. Complete conversion to the NHS ester eluting at 22 minutes was observed. This DMF solution was added drop wise to a stirred solution of compound 11c (46 mg, 5 equivalents, HBr salt) in 0.25 M sodium bicarbonate (1 mL). The resulting solution was stirred at room temperature. After 15 minutes, HPLC analysis indicated a major product eluting at Rt=14 minutes.

The product 15d was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. HPLC fractions containing the product were combined and concentrated under reduced pressure. Yield=18 mg (quantitative); MALDI-TOF MS 935.8 observed.

e) Compound 15f

A solution of compound 15d (18 mg, 19.2 umoles) in methanol (1.8 mL) and water (0.2 mL) was treated with diisopropylethylamine (26 uL, 5 equivalents) and glutaric anhydride (17 mg, 5 equivalents). The reaction was stirred at room temperature. After 15 minutes, HPLC analysis as described in section (d) showed complete conversion to the glutarate derivative 15e eluting at Rt=16.2 minutes. The reaction was diluted with toluene (5 mL) and concentrated under reduced pressure. The residue was dissolved in DMF (1.8 mL) and water (0.2 mL) and was treated with diisopropylethylamine (52 uL, 10 equivalents) and TSTU (90 mg, 10 equivalents). The reaction was stirred at room temperature. After 30 minutes, HPLC analysis complete conversion to the product eluting at Rt=19 minutes. The product 15f was purified by preparative HPLC using an YMC, $C_{18}$ 30×300 mm column and 40 minute gradient of 10→60% B (A=water with 0.05% TFA, B=MeCN with 0.05% TFA) at a solvent flow rate of 20 mL/minute and UV detection at 260 nm. HPLC fractions containing the product were combined, frozen at −80° C. and lyophilized to dryness. Yield=6.5 mg (30%); MALDI-TOF MS 1146.6 observed.

The following reactions describe the synthesis of CN-NSP-DMAE-$Z_3$-NHS, compound 15f.

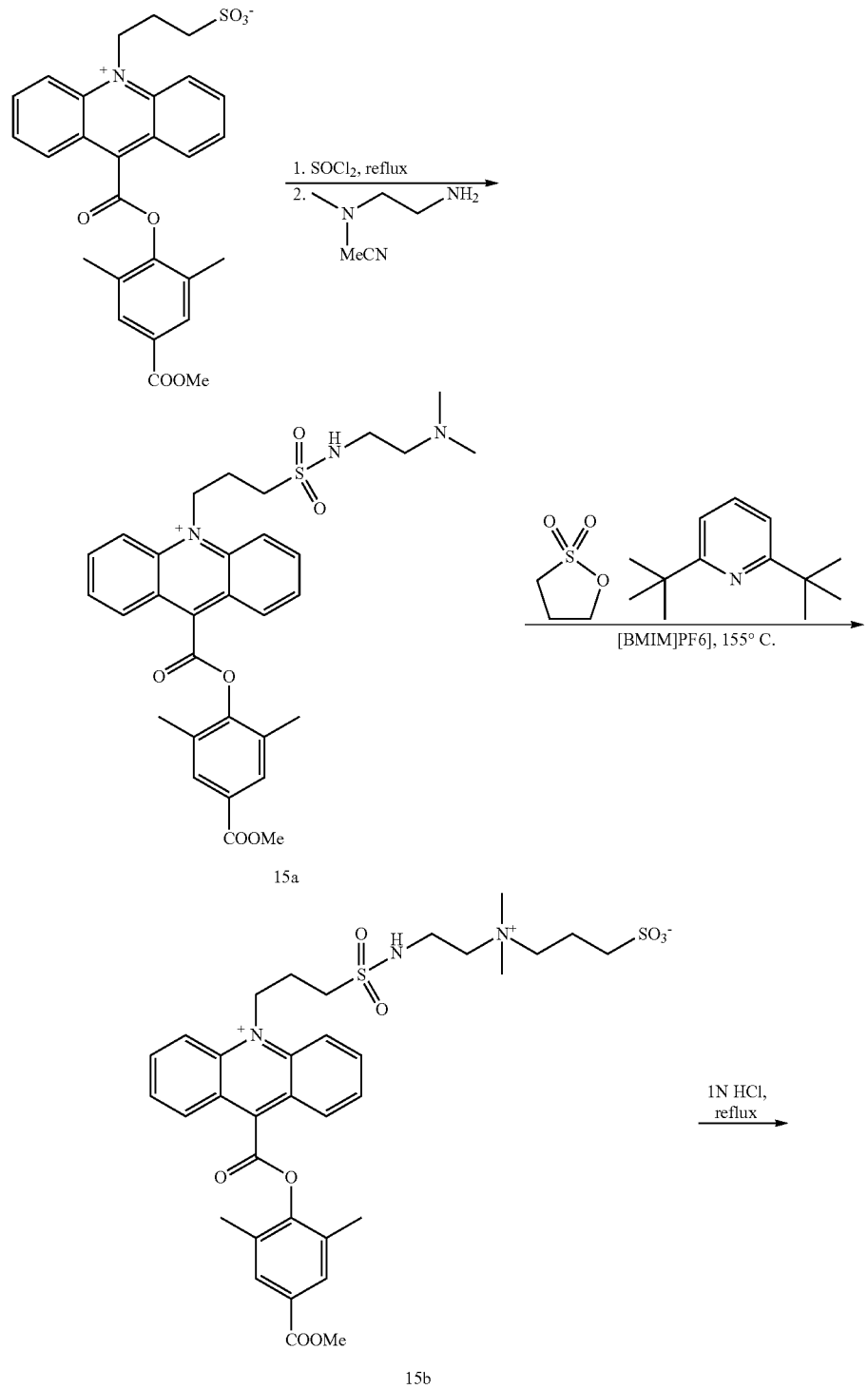

-continued
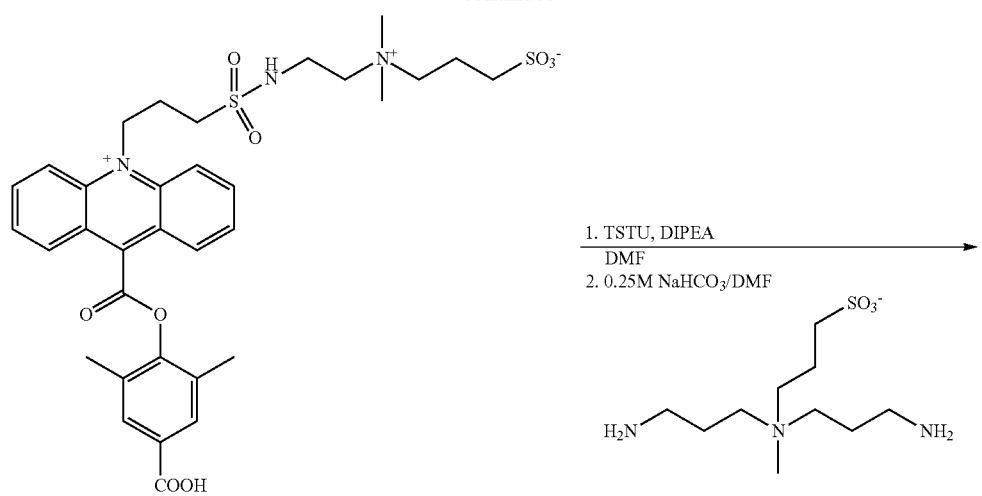
15c
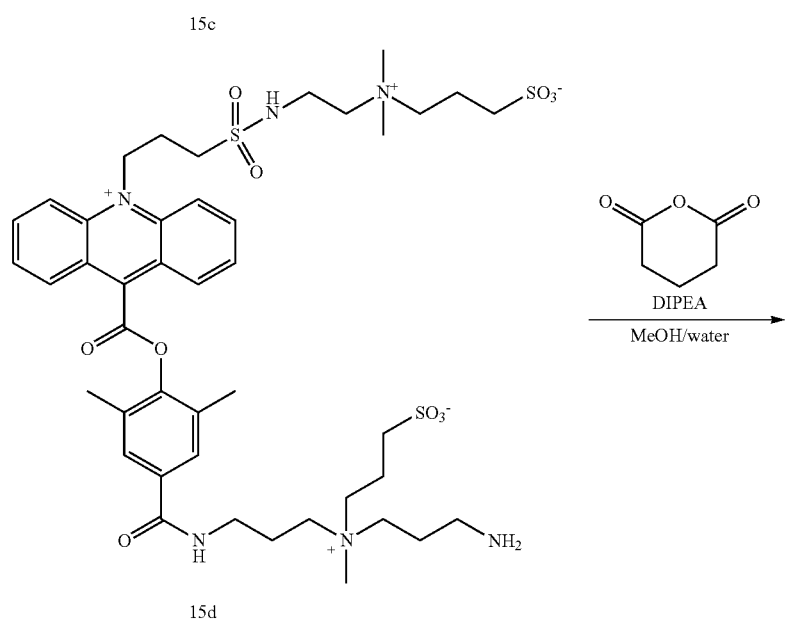
15d
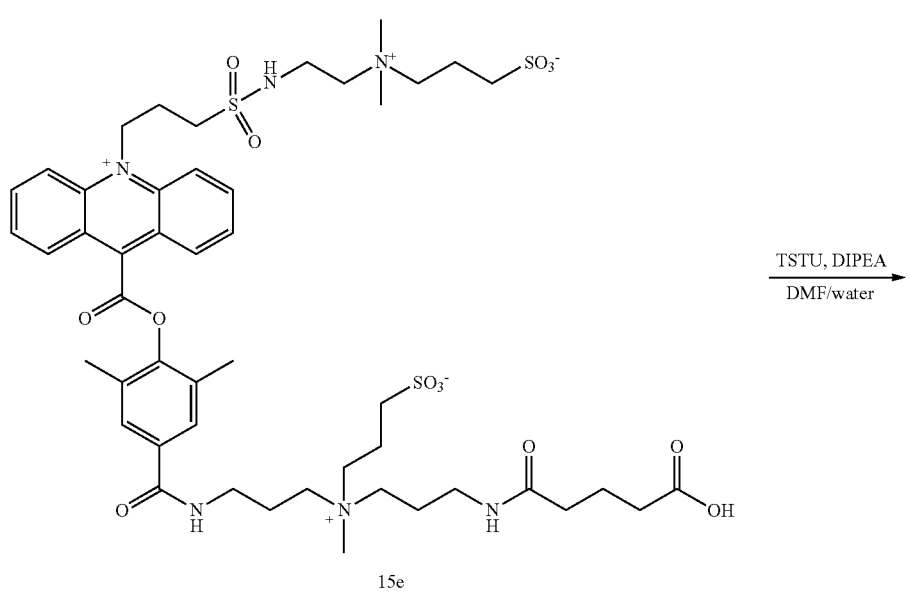
15e

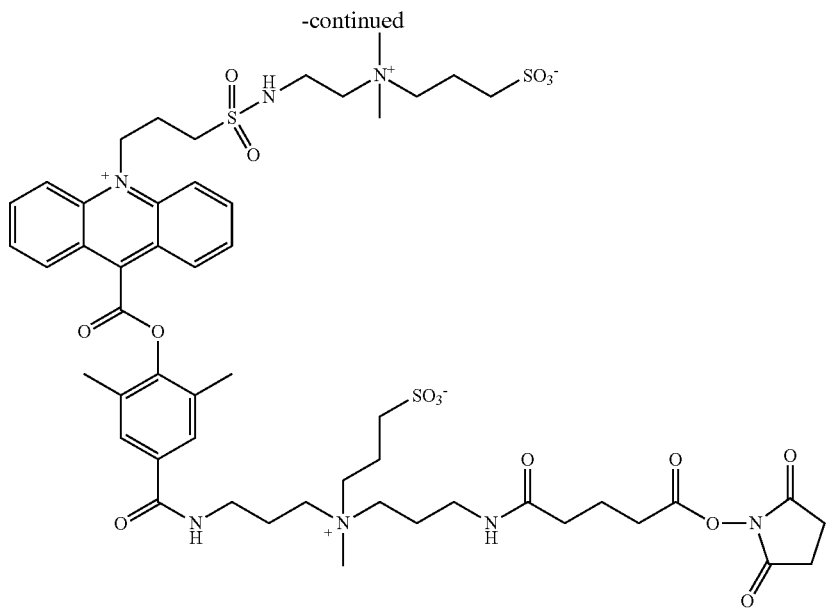

15f

Example 16

General Procedure for Labeling Anti-TSH Mab with Acridinium Ester

A stock solution of the antibody (5 mg/mL, 200 uL, 1.0 mg, 6.7 nmoles) was diluted with 0.1 M sodium carbonate pH 9 (250 uL) to give a ~2.0 mg/mL solution. To this solution was added 10 equivalents of the acridinium NHS ester as a solution in either 1:1, DMF/water solution or DMSO. For example, using NSP-DMAE-Z-NHS, 11f, this entailed the addition of 64 micrograms added as of a 5 mg/mL solution (12.8 uL) of the acridinium ester. The labeling reactions were stirred gently at 4° C. for 16 hours and were then diluted with de-ionized water to 4 mL. These diluted solutions were then transferred to 4 mL Centricon™ filters (MW 30,000 cutoff) and centrifuged at 4000G to reduce the volume to ~0.2 mL. This process was repeated three more times. The filtered conjugates were finally diluted into a total volume of 250 uL water for mass spectral analysis and RLU measurements.

Mass spectra were recorded on a Voyager DE MALDI-TOF mass spectrometer and the unlabeled antibody was used as the reference. Approximately 2 uL of the conjugate solution was mixed with 2 uL of sinnapinic acid matrix solution (HP) and the spotted on a MALDI plate. After complete drying, mass spectra were recorded. From the difference in mass values for the unlabeled antibody and the conjugates, the extent of AE incorporation could be measured. Typically, under these labeling conditions, ~5 AE labels were incorporated in the antibody.

Example 17

Chemiluminescence Measurements

Each acridinium ester labeled antibody was diluted to a concentration of 0.2 nanomolar in a buffer consisting of 0.1 M sodium phosphate, 0.15 M sodium chloride, 6 mM sodium azide and 1 g/L bovine serum albumin (BSA). The chemiluminescence kinetics for 10 microliters of each acridinium ester-antibody conjugate tested was integrated in 0.1 second intervals for 10 seconds under standard conditions on a Berthold Technolgies Autolumat LB953 luminometer with sequential addition of 300 microliters each of Reagent 1 (0.1 M nitric acid and 0.5% hydrogen peroxide) and Reagent 2 (0.25 M sodium hydroxide and 0.05% cetyltrimethylammonium chloride). The chemiluminescence kinetics of the tested acridinium compounds were compared for relative rate of light emission as well as total light output.

Example 18

Measurement of Non-Specific Binding

Zwitterionic acridinium compounds were tested as labels in an immunoassay for comparison with control acridinium compounds used separately as labels in the same immunoassay. The Siemens Healthcare Diagnostics ACS:180® TSH3 assay is one of a series of commercially marketed immunoassays manufactured by Siemens Healthcare Diagnostics for application on the ACS:180®. The TSH3 assay is a sandwich immunoassay which uses a chemiluminescent acridinium compound of an anti-TSH antibody for measurement of the analyte TSH (Thyroid Stimulating Hormone) in a sample.

The TSH3 assay has two antibodies, one of which is a mouse antibody attached to acridinium compound, the combination being called the tracer, while the other antibody is attached to paramagnetic particles (PMP), where this combination is called a solid phase. In this example assay both the zwitterionic acridinium compounds and also the control acridinium compounds were each attached to the same antibody in separate portions. In this example assay, only non-specific binding was measured where acridinium ester conjugates or tracers were tested in the absence of TSH analyte in the sample. Tracers were diluted to a concentration of 2.2 nM in a buffer containing 0.15 M N-2-hydroxyethylpiperazine-N'-2-ethanesulfonic acid (HEPES), 0.15 M sodium chloride, 7.7 mM sodium azide, 1.0 mM ethylenediaminetetraacetic acid (EDTA), 12 mM t-octylphenoxypolyethoxyethanol (Triton X-100), 5 g/L bovine serum albumin (BSA), 0.20 g/L amphotericin B, 0.48 g/L gentamicin sulfate, 1 g/L mouse IgG, 10 mg/L sheep IgG, 5.0 g/L mouse serum, 0.05 g/L antifoam B, pH 7.7. In this example assay three solid phases were tested with the acridinium compounds: Siemens Healthcare Diagnostics TSH3 Assay Solid Phase, Siemens Healthcare Diagnostics iPTH (Intact Parathyroid Hormone) Assay Solid Phase (Dynal M280-streptavidin bound biotinylated polyclonal goat anti-PTH antibody) and Siemens Healthcare Diagnostics TnI (Troponin I)-ultra Assay (Dynal M270-streptavidin bound biotinylated monoclonal mouse anti-TnI antibody).

The Siemens Healthcare Diagnostics ACS:180® is an automated robotic device designed to perform a series of immunoassays for different analytes. The automated procedure for the Siemens Healthcare Diagnostics ACS:180® TSH3 assay was initiated with the dispensing of 200 μL each of serum samples that do not contain TSH analyte into separate cuvets. A cuvet is an optically transparent or translucent container for mixing the tracer, sample and solid phase and in which chemiluminescence is measured. The samples did not contain the analyte TSH. The ACS:180® then dispensed 0.100 mL of 2.2 nM (0.22 pmol) tracer and 0.225 mL of 0.3 g/L (67 μg) solid phase into each cuvet containing the samples, such that the same amount of tracer and solid phase were used for all tested acridinium compounds. The first of the two assay reagents was solution, which contained of anti-TSH antibody conjugated with acridinium compound. Both the zwitterionic acridinium compounds and control acridinium compounds were tested separately as labels for tracers. The traces were prepared and purified using the procedure described previously using acridinium compounds and TSH-binding mouse antibody. The number of acridinium compounds per antibody in each tracer was approximately the same for all tested acridinium compounds. Therefore, any difference in non-specific binding measured for each acridinium compound could be related to the structure of the acridinium compound. The mixture of tracer, sample and solid phase in each cuvet was heated for 5.0 minutes at 37° C. Unbound tracer was removed from the solid phase with magnetic separation of the solid phase from the mixture in the cuvet, followed by removal of fluid from the cuvet and washing of the solid phase in the cuvet with water to remove everything but the solid phase and any tracer bound to it.

Chemiluminescence from acridinium compounds on the solid phase was initiated with subsequent light emission with sequential additions of 0.30 mL each of Siemens Healthcare Diagnostics ACS:180® Reagent 1 and Siemens Healthcare Diagnostics ACS:180® Reagent 2. Siemens Healthcare Diagnostics ACS:180® Reagent 1 was 0.1 M nitric acid and 0.5% hydrogen peroxide. Siemens Healthcare Diagnostics ACS:180® Reagent 2 was 0.25 M sodium hydroxide and 0.05% cetyltrimethylammonium chloride. The chemiluminescence in each cuvet was then measured as relative light units (RLUs) with each cuvet corresponding to a single assayed sample. Non-specific binding for each tested acridinium compound was measured as chemiluminescence in units of RLUs with the number of RLUs measured by the Siemens Healthcare Diagnostics ACS:180®. Fractional non-specific binding is defined as the ratio of the non-specific binding chemiluminescence to the total chemiluminescence input into each cuvet from 0.22 pmol tracer. Minimalization of fractional non-specific binding maximizes measurement of specific signal thus improving measurement of smaller quantities of analyte and enhancing immunoassay performance. In this example assay, zwitterionic acridinium compounds have lower fractional non-specific binding and would therefore be expected to enhance immunoassay performance.

Example 19

Measurement of Acridinium Conjugate Chemiluminescence Stability

Conjugates of zwitterionic acridinium compounds and control acridinium compounds NSP-DMAE-HEG and HQY-AE were diluted to a concentration of 0.1 nM in a buffer containing 0.15 M N-2-hydroxyethylpiperazine-N'-2-ethanesulfonic acid (HEPES), 0.15 M sodium chloride, 7.7 mM sodium azide, 1.0 mM ethylenediaminetetraacetic acid (EDTA), 12 mM t-octylphenoxypolyethoxyethanol (Triton X-100), 5 g/L bovine serum albumin (BSA), 0.20 g/L amphotericin B, 0.48 g/L gentamicin sulfate, 1 g/L mouse IgG, 10 mg/L sheep IgG, 5.0 g/L mouse serum, 0.05 g/L antifoam B, pH 7.7. All conjugates were then stored at either 4 or 37° C. for four weeks in sealed polyethylene bottles. 10 μLs of each tracer stored at either 4 or 37° C. was periodically removed for chemiluminescence measurement on the Bertholdt ALB953 chemiluminometer which used the same method for chemiluminescence measurement as the Siemens Healthcare Diagnostics ACS:180® using Siemens Healthcare Diagnostics ACS:180® Reagents 1 and 2. Chemiluminescence was then compared as a percentage to that determined for each tracer at the start of storage at either 4 or 37° C. Enhanced or equivalent chemiluminescence stability relative to control acridinium compounds would be a desirable property for new acridinium compounds providing longer or equivalent shelf-life of product and better or equivalent day to day reproducibility of results.

What is claimed:
1. A chemiluminescent acridinium compound having the following structure, wherein said acridinium compound exhibits reduced non-specific binding to a solid phase as compared to an otherwise identical acridinium compound not comprising said zwitterionic functional group:

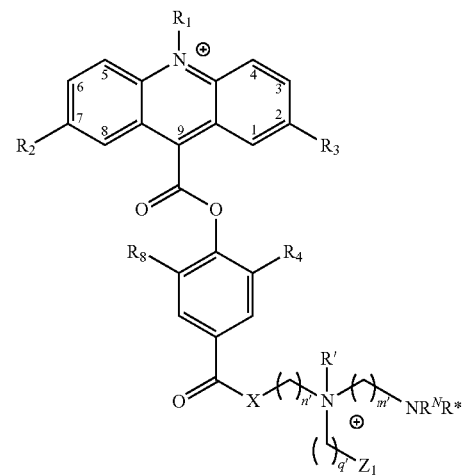

wherein:
$R_1$ is a $C_{1-35}$ alkyl, alkenyl, alkynyl or aralkyl group, each of which may contain up to 20 heteroatoms, or a sulfopropyl or sulfobutyl group, or $R_1$ is a group —$R^a$—Z;
$R_2$ and $R_3$ are independently selected from (i) hydrogen, (ii) an electron donating group, or (iii) a group —Z;
Z is a zwitterionic group of the form:

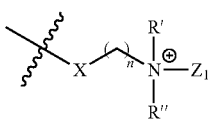

wherein:
X is independently selected at each occurrence from a bond, —$CH_2$—, oxygen, sulfur, —$NR^N$—, amide (—$NR^N(CO)$—), carbamate (—$NR^NC(O)O$—), or urea (—$NR^NC(O)NR^N$—);

R' and R" are independently selected at each occurrence from $C_{1-35}$ alkyl, alkenyl, alkynyl, aryl, or aralkyl, each optionally containing up to 20 heteroatoms;

$Z_1$ is a group —$R^a$—$Z_2$ where $Z_2$ is selected from carboxylate (—COO$^-$), sulfonate (—SO$_3^-$), sulfate (—OSO$_3^-$), phosphate (—OP(O)(OR)(O$^-$)), or oxide (—O$^-$); or, in the case where $Z_2$ is an oxide (—O$^-$), $R^a$ may be absent; and n is, independently selected at each occurrence, an integer between one and 12;

$R_4$ and $R_8$ are the same or different and are selected from hydrogen, $C_{1-35}$ alkyl, alkenyl, alkynyl, alkoxyl (—OR), alkylthiol (—SR), or substituted amino groups (—NR$_2$);

$R^a$ is a divalent radical selected from $C_{1-35}$ alkyl, alkenyl, alkynyl, aryl, or aralkyl group, each optionally containing up to 20 heteroatoms;

$R^N$ is independently selected at each occurrence from hydrogen, $C_{1-35}$ alkyl, alkenyl, alkynyl, aryl, or aralkyl groups each containing up to 20 heteroatoms;

R is independently selected at each occurrence from $C_{1-35}$ alkyl, alkenyl, alkynyl, aryl, or aralkyl groups each containing up to 20 heteroatoms;

R* is selected from hydrogen, $C_{1-35}$ alkyl, alkenyl, alkynyl, aryl, or aralkyl, each optionally containing up to 20 heteroatoms, or R* is a group —$R^a$-L, wherein L is a leaving group for forming a conjugate with an analyte, analyte analog, or binding partner for an analyte; and n', m', and q' are each independently an integer from 1-4.

2. The chemiluminescent acridinium compound according to claim 1, wherein one of $R_1$, $R_2$, $R_3$, and R*, comprises a group -L or —$R^a$-L.

3. The chemiluminescent acridinium compound according to claim 2, wherein L is selected from the group consisting of:

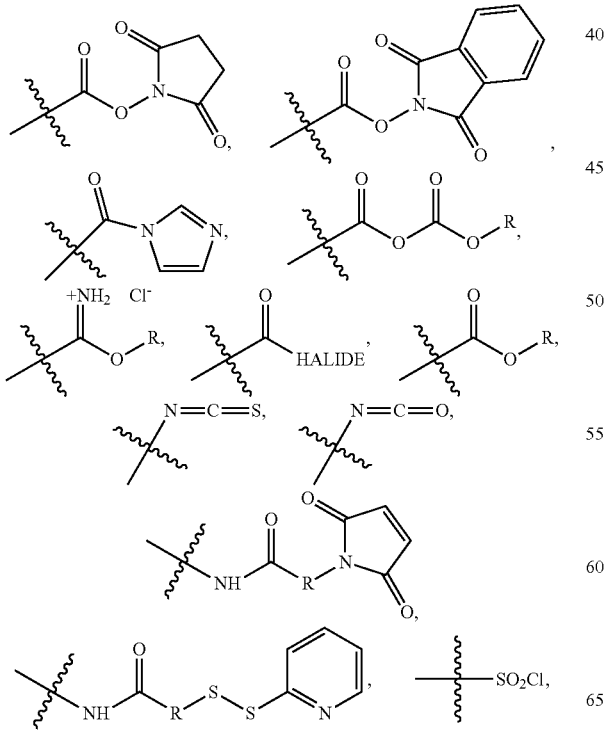

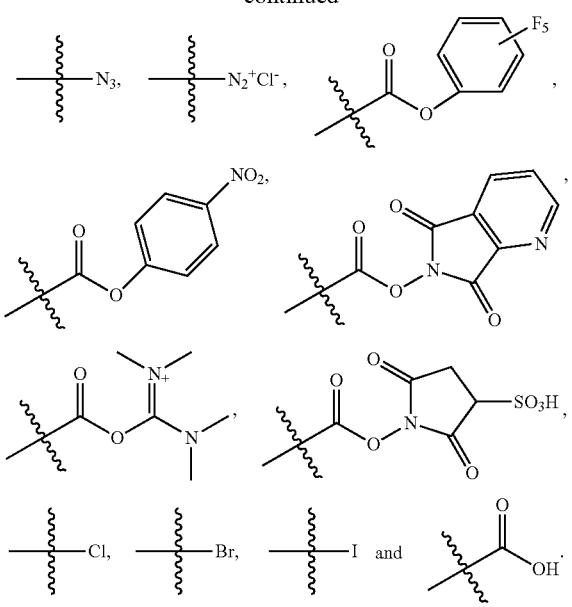

4. The chemiluminescent acridinium compound according to claim 1, wherein R' or R" comprises a group —$R^a$-L.

5. The chemiluminescent acridinium compound according to claim 4, wherein R' or R" are, at one occurrence, a group —$R^a$—C(O)—CH$_2$CH$_2$CH$_2$—C(O)—N-succinimidyl, —$R^a$—N-maleimido, —$R^a$—C(O)—CH$_2$—Br, or —$R^a$—C(O)—CH$_2$—I.

6. The chemiluminescent acridinium compound according to claim 1, wherein said electron donating groups are selected from the group consisting of (i) alkoxyl (—OR), (ii) a group —O—(CH$_2$CH$_2$—O)$_l$—CH$_3$ where l is an integer from 1 to 12, and (iii) a group —O-G, and (vi) a group —Z;

where G is a branched group independently selected at each occurrence from:

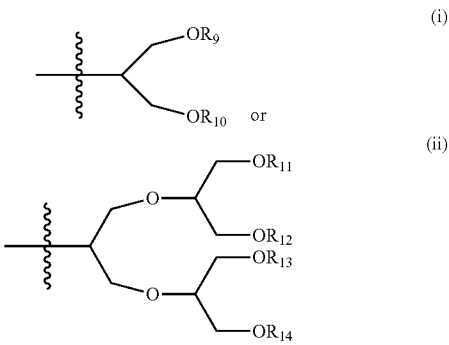

and where $R_9$, $R_{10}$, $R_{11}$ $R_{12}$, $R_{13}$ and $R_{14}$ are independently at each occurrence a methyl group or a group —(CH$_2$CH$_2$O)—CH$_3$, where m is an integer from 1 to 5.

7. The chemiluminescent acridinium compound according to claim 1, wherein R* comprises a group —$R^a$-L.

8. The chemiluminescent acridinium compound according to claim 1, having the following structure:

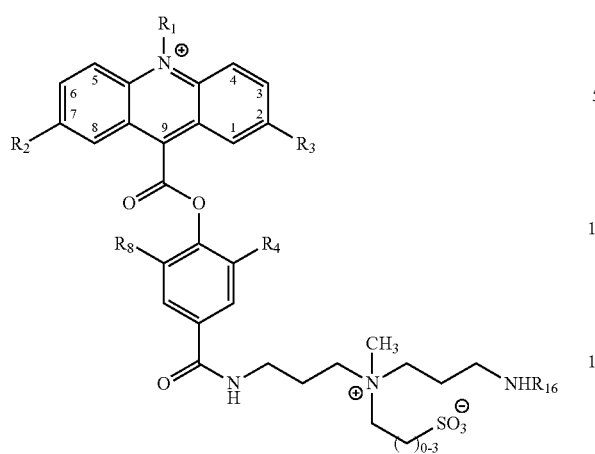

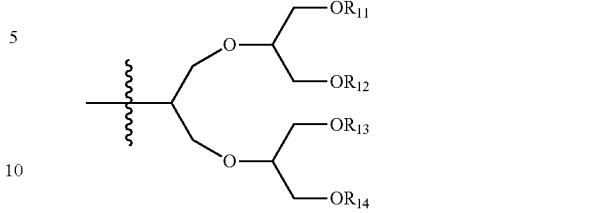

and where $R_9$, $R_{10}$, $R_{11}$ $R_{12}$, $R_{13}$ and $R_{14}$ are independently at each occurrence a methyl group or a group —$(CH_2CH_2O)_mCH_3$, where m is an integer from 1 to 5.

10. The chemiluminescent acridinium compound according to claim 1, having the following structure:

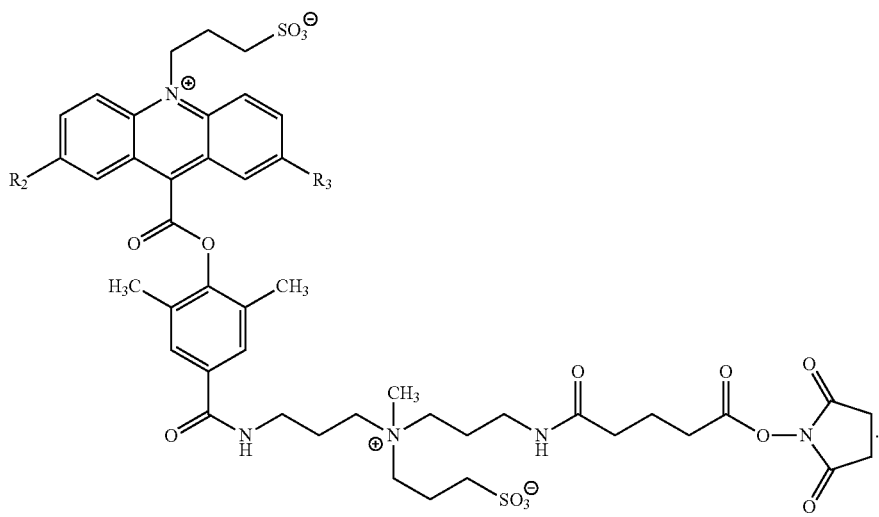

wherein
$R_{16}$ is selected from (i) hydrogen, (ii) —C(O)—$CH_2CH_2CH_2$—C(O)—N-succinimidyl, (iii) —R—N-maleimido where R is independently alkyl, alkenyl, alkynyl, or aralkyl, each of which may optionally comprise up to 20 heteroatoms, or (iv) —C(O)—$CH_2$—X where X is bromine (Br) or iodine (I).

9. The chemiluminescent acridinium compound according to claim 8, wherein:
$R_1$ is selected from methyl, sulfopropyl (—$CH_2CH_2CH_2$—$SO_3^-$), or sulfobutyl (—$CH_2CH_2$ $CH_2CH_2$—$SO_3^-$) groups; and $R_2$ and $R_3$ are selected independently from hydrogen or a group —O-G, where G is a branched group independently selected at each occurrence from:

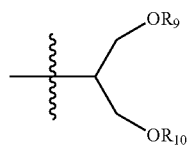

11. The chemiluminescent acridinium compound according to claim 10, wherein $R_2$ and $R_3$ are independently selected from hydrogen or a group —O-G, where G is a branched group independently selected at each occurrence from:

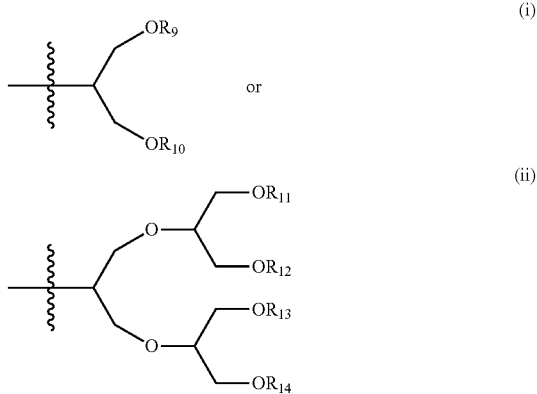

and where $R_9$, $R_{10}$, $R_{11}$ $R_{12}$, $R_{13}$ and $R_{14}$ are independently at each occurrence a methyl group or a group —(CH$_2$CH$_2$O)$_m$CH$_3$, where m is an integer from 1 to 5.

12. The chemiluminescent acridinium compound according to claim 10, wherein $R_2$ and $R_3$ are hydrogen.

13. The chemiluminescent acridinium compound according to claim 1, wherein $R_1$ is —R$^a$—Z.

14. The chemiluminescent acridinium compound according to claim 13, having the following structure:

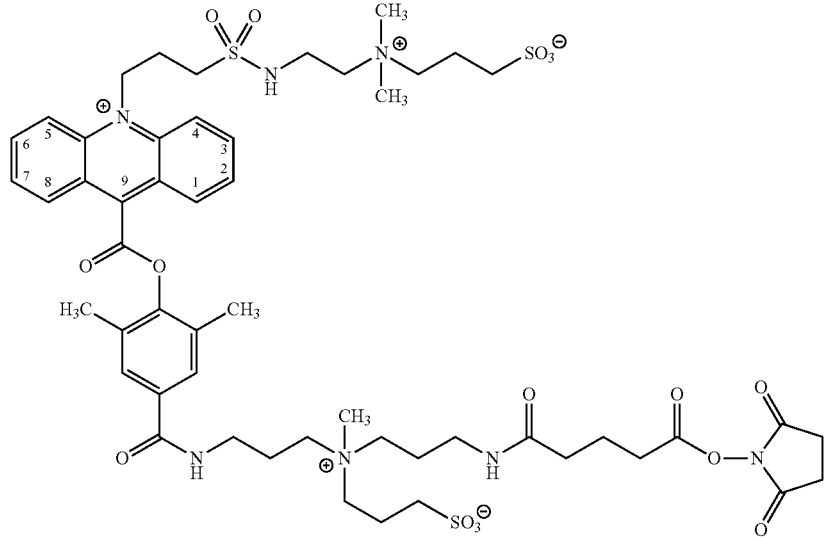

wherein the compound optionally includes a counterion A$^-$ to balance the positively charged nitrogen of the acridinium nucleus.

15. A reagent for the detection of an analyte comprising a chemiluminescent acridinium compound bound to an analyte, analyte analog, or binding partner for an analyte, the acridinium compound having the following structure, wherein said acridinium compound exhibits reduced non-specific binding to a solid phase as compared to an otherwise identical acridinium compound not comprising said zwitterionic functional group:

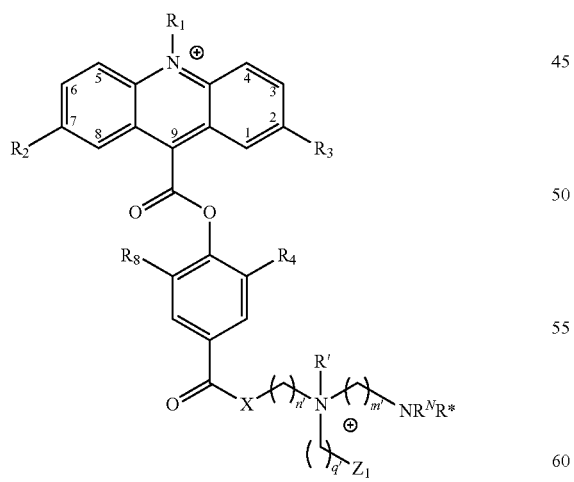

wherein:
$R_1$ is a $C_{1-35}$ alkyl, alkenyl, alkynyl or aralkyl group, each of which may contain up to 20 heteroatoms, or a sulfopropyl or sulfobutyl group, or $R_1$ is a group —R$^a$—Z;
$R_2$ and $R_3$ are independently selected from (i) hydrogen, (ii) an electron donating group, or (iii) a group —Z;

Z is a zwitterionic group of the form:

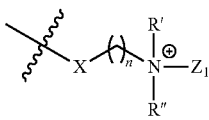

wherein:
X is independently selected at each occurrence from a bond, —CH$_2$—, oxygen, sulfur, —NR$^N$—, amide (—NR$^N$(CO)—), carbamate (—NR$^N$C(O)O—), or urea (—NR$^N$C(O)NR$^N$—);

R' and R" are independently selected at each occurrence from $C_{1-35}$ alkyl, alkenyl, alkynyl, aryl, or aralkyl, each optionally containing up to 20 heteroatoms;

$Z_1$ is a group —R$^a$—$Z_2$ where $Z_2$ is selected from carboxylate (—COO$^-$), sulfonate (—SO$_3^-$), sulfate (—OSO$_3^-$), phosphate (—OP(O)(OR)(O$^-$)), or oxide (—O$^-$); or, in the case where $Z_2$ is an oxide (—O$^-$), R$^a$ may be absent; and n is, independently selected at each occurrence, an integer between one and 12;

$R_4$ and $R_8$ are the same or different and are selected from hydrogen, $C_{1-35}$ alkyl, alkenyl, alkynyl, alkoxyl (—OR), alkylthiol (—SR), or substituted amino groups (—NR$_2$);

R$^a$ is a divalent radical selected from $C_{1-35}$ alkyl, alkenyl, alkynyl, aryl, or aralkyl group, each optionally containing up to 20 heteroatoms;

R$^N$ is independently selected at each occurrence from hydrogen, $C_{1-35}$ alkyl, alkenyl, alkynyl, aryl, or aralkyl groups each containing up to 20 heteroatoms;

R is independently selected at each occurrence from $C_{1-35}$ alkyl, alkenyl, alkynyl, aryl, or aralkyl groups each containing up to 20 heteroatoms;

R* is selected from hydrogen, $C_{1-35}$ alkyl, alkenyl, alkynyl, aryl, or aralkyl, each optionally containing up to 20 heteroatoms, or R* is a group —R$^a$-L, wherein L is a leaving group for forming a conjugate with an analyte, analyte analog, or binding partner for an analyte; and n', m', and q' are each independently an integer from 1-4.

16. An assay for the detection or quantification of a macromolecular analyte comprising:
   (a) providing a conjugate comprising a chemiluminescent acridinium compound according to claim 1 bound to a binding molecule specific for an analyte;
   (b) providing a solid support having immobilized thereon a second binding molecule specific for said analyte;
   (c) mixing the conjugate, the solid phase and a sample suspected of containing the analyte to form a binding complex;
   (d) separating the binding complex captured on the solid support;
   (e) triggering chemiluminescence of the binding complex from step (d) by adding chemiluminescence triggering reagents;
   (f) measuring the amount of light emission with a luminometer; and
   (g) detecting the presence or calculating the concentration of the analyte by comparing the amount of light emitted from the reaction mixture with a standard dose response curve which relates the amount of light emitted to a known concentration of the analyte.

17. An assay for the detection or quantification of a small molecule analyte is provided comprising the steps of:
   (a) providing a conjugate of an analyte with a chemiluminescent acridinium compound according to claim 1;
   (b) providing a solid support immobilized with a binding molecule specific for the analyte;
   (c) mixing the conjugate, solid support and a sample suspected of containing the analyte to form a binding complex;
   (d) separating the binding complex captured on the solid support;
   (e) triggering the chemiluminescence of the binding complex from step (d) by adding chemiluminescence triggering reagents;
   (f) measuring the amount of light with an luminometer; and
   (g) detecting the presence or calculating the concentration of the analyte by comparing the amount of light emitted from the reaction mixture with a standard dose response curve which relates the amount of light emitted to a known concentration of the analyte.

18. An assay for the detection of small molecule analyte comprising:
   a) providing a solid support immobilized with an analyte or an analyte analog;
   b) providing a conjugate of a binding molecule specific for the analyte with a chemiluminescent acridinium compound according to claim 1;
   c) mixing the solid phase, the conjugate and a sample suspected containing the analyte to form a binding complex;
   d) separating the binding complex captured on the solid support;
   e) triggering the chemiluminescence of the binding complex of (d) by adding chemiluminescence triggering reagents;
   f) measuring the amount of light with an luminometer; and
   g) detecting the presence or calculating the concentration of the analyte by comparing the amount of light emitted from the reaction mixture with a standard dose response curve which relates the amount of light emitted to a known concentration of the analyte.

19. The reagent according to claim 15, wherein one of $R_1$, $R_2$, $R_3$, and $R^*$, comprises a group -L or —$R^a$-L.

20. The reagent according to claim 15, wherein L is selected from the group consisting of:

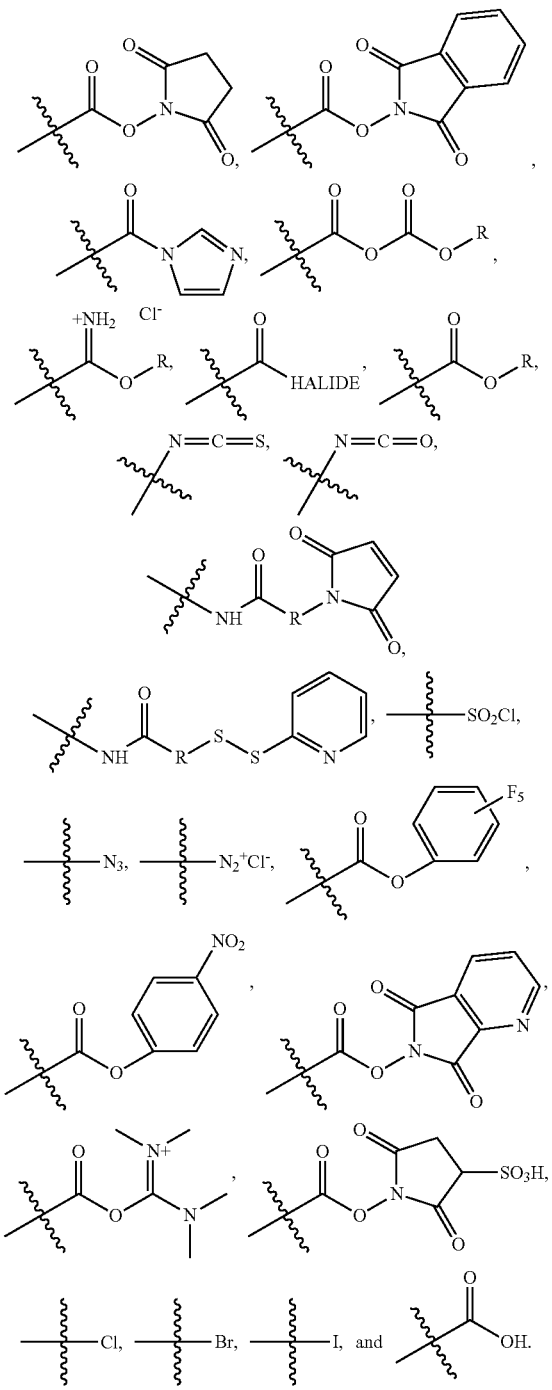

21. The reagent according to claim 15, wherein R' or R" comprises a group —$R^a$-L.

22. The reagent according to claim 21, wherein R' or R" are, at one occurrence, a group —$R^a$—C(O)—$CH_2CH_2CH_2$—C(O)—N-succinimidyl, —$R^a$—N-maleimido, —$R^a$—C(O)—$CH_2$—Br, or —$R^a$—C(O)—$CH_2$—I.

23. The reagent according to claim 15, wherein said electron donating groups are selected from the group consisting of (i) alkoxyl (—OR), (ii) a group —O—$(CH_2CH_2$—O$)_l$—$CH_3$ where l is an integer from 1 to 12, and (iii) a group —O-G, and (vi) a group —Z; where G is a branched group independently selected at each occurrence from:

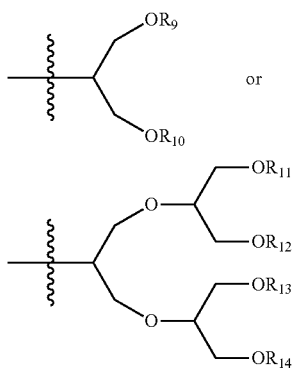

(i)

(ii)

and where $R_9$, $R_{10}$, $R_{11}$ $R_{12}$, $R_{13}$ and $R_{14}$ are independently at each occurrence a methyl group or a group —$(CH_2CH_2O)_mCH_3$, where m is an integer from 1 to 5.

24. The reagent according to claim 15, wherein R* comprises a group —$R^a$-L.

25. The reagent according to claim 15, wherein the chemiluminescent acridinium compound has the following structure:

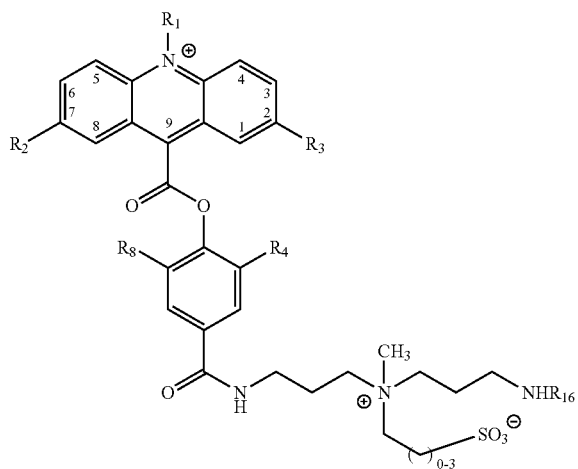

$R_{16}$ is selected from (i) hydrogen, (ii) —C(O)—$CH_2CH_2CH_2$—C(O)—N-succinimidyl, (iii) —R—N-maleimido where R is independently alkyl, alkenyl, alkynyl, or aralkyl, each of which may optionally comprise up to 20 heteroatoms, or (iv) —C(O)—$CH_2$—X where X is bromine (Br) or iodine (I).

26. The reagent according to claim 25, wherein $R_1$ is selected from methyl, sulfopropyl (—$CH_2CH_2CH_2$—$SO_3^-$), or sulfobutyl (—$CH_2CH_2CH_2CH_2$—$SO_3^-$) groups; and $R_2$ and $R_3$ are selected independently from hydrogen or a group —O-G, where G is a branched group independently selected at each occurrence from:

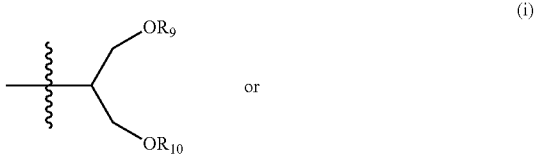

(i)

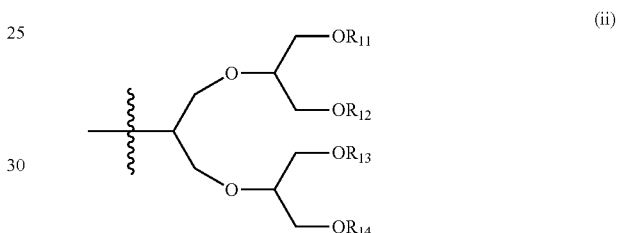

(ii)

and where $R_9$, $R_{10}$, $R_{11}$ $R_{12}$, $R_{13}$ and $R_{14}$ are independently at each occurrence a methyl group or a group —$(CH_2CH_2O)_mCH_3$, where m is an integer from 1 to 5.

27. The reagent according to claim 15, wherein the chemiluminescent acridinium compound has the following structure:

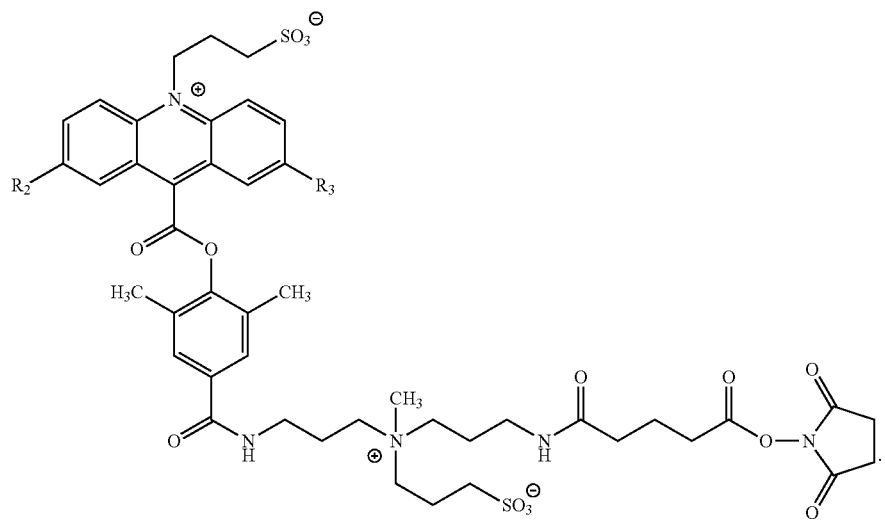

28. The reagent according to claim 27, wherein $R_2$ and $R_3$ are independently selected from hydrogen or a group —O-G, where G is a branched group independently selected at each occurrence from:

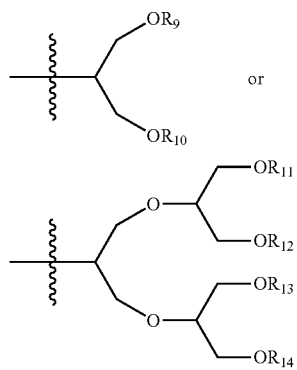

(i)

(ii)

and where $R_9$, $R_{10}$, $R_{11}$, $R_{12}$, $R_{13}$ and $R_{14}$ are independently at each occurrence a methyl group or a group —$(CH_2CH_2O)_mCH_3$, where m is an integer from 1 to 5.

29. The reagent according to claim 27, wherein $R_2$ and $R_3$ are hydrogen.

30. The reagent according to claim 15, wherein $R_1$ is —$R^a$—Z.

31. The reagent according to claim 30, wherein the chemiluminescent acridinium compound has the following structure:

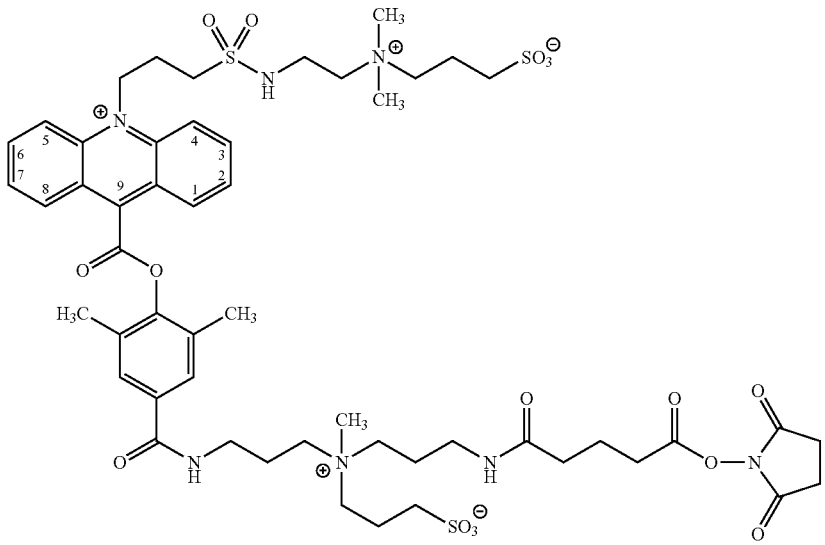

wherein the compound optionally includes a counterion $A^-$ to balance the positively charged nitrogen of the acridinium nucleus.

* * * * *